United States Patent [19]
Joyce

[11] Patent Number: 5,595,873
[45] Date of Patent: Jan. 21, 1997

[54] *T. THERMOPHILA* GROUP I INTRONS THAT CLEAVE AMIDE BONDS

[75] Inventor: Gerald F. Joyce, Encinitas, Calif.

[73] Assignee: The Scripps Research Institute, La Jolla, Calif.

[21] Appl. No.: 270,180

[22] Filed: Jul. 1, 1994

Related U.S. Application Data

[63] Continuation-in-part of Ser. No. 242,402, May 13, 1994.
[51] Int. Cl.$^6$ .............................. C12Q 1/68; C12H 15/10
[52] U.S. Cl. ................ 435/6; 435/91.31; 435/172.1; 536/23.1; 536/23.2
[58] Field of Search ................ 435/6, 91.31, 172.1; 536/23.1, 23.2, 24.5; 514/44

[56] References Cited

PUBLICATIONS

Bartel and Szostak, *Science* 261:1411–1418 (1993).
Beaudry and Joyce, *Biochemistry* 29: 6534 (1990).
Beaudry and Joyce, *Science* 257:635–641 (1992).
Burke, *Gene* 73:273–294 (1988).
Cadwell and Joyce, in *PCR Methods and Applications* 2: 28–33 (1992).
Cadwell and Joyce, in *PCR Methods and Applications* 3 *(Suppl.)*: s136–s140 (1994).
Cech, *Science* 236:1532–1539 (1987).
Herschlag and Cech, *Nature* 344: 405–409 (1990).
Herschlag & Cech, *Biochemistry* 29:10159–10171 (1990).
Inoue et al., *J. Mol. Biol.* 189: 143–165 (1986).
Joyce et al., *Nucl. Acids Res.* 15: 9825 (1987).
Joyce and Inoue, *Nucleic Acid Res.* 17: 711–722 (1989).
Joyce et al., *Nucleic Acid Res.* 17: 7879 (1989).
Joyce, *Gene* 82: 83 (1989).
Joyce, in *Molecular Biology of RNA: UCLA Symposia on Molecular and Cellular Biology*, T. R. Cech (ed.), Liss, NY, 1989, pp. 361–371.
Joyce, in *Antisense RNA and DNA*, J. A. H. Murray (ed.), Wiley–Liss, NY, 1992, pp. 353–372.
Piccirilli, et al., *Science* 256: 1420–1424 (1992).
Lehman and Joyce, *Nature* 361: 182–185 (1993).
Robertson and Joyce, *Nature* 344: 467 (1990).
Sugimoto et al., *Nucleic Acids Res.* 17:355–371 (1989).
Tsang and Joyce, *Biochemistry* 33: 5966–5973 (1994).
Wang and Cech, *Science* 256: 526–529 (1992).
Zaug et al., *Nature* 324: 429–433 (1986).
Zaug et al., *Science* 231: 470–475 (1986).

*Primary Examiner*—John L. Leguyader
*Attorney, Agent, or Firm*—April C. Logan

[57] ABSTRACT

The present invention relates to nucleic acid enzymes or enzymatic RNA molecules that are capable of cleaving a variety of bonds, including phosphodiester bonds and amide bonds, in a variety of substrates. Thus, the disclosed enzymatic RNA molecules are capable of functioning as nucleases and/or peptidases. The present invention also relates to compositions containing the disclosed enzymatic RNA molecule and to methods of making, selecting, and using such enzymes and compositions.

20 Claims, 7 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:1:

| | | | | | | |
|---|---|---|---|---|---|---|
| GGAGGGAAAA | GUUAUCAGGC | AUGCACCUGG | UAGCUAGUCU | UUAAACCAAU | AGAUUGCAUC | 60 |
| GGUUUAAAAG | GCAAGACCGU | CAAAUUGCGG | GAAAGGGGUC | AACAGCCGUU | CAGUACCAAG | 120 |
| UCUCAGGGGA | AACUUGAGA | UGGCCUUGCA | AAGGGUAUGG | UAAUAAGCUG | ACGGACAUGG | 180 |
| UCCUAACCAC | GCAGCCAAGU | CCUAAGUCAA | CAGAUCUUCU | GUUGAUAUGG | AUGCAGUUCA | 240 |
| CAGACUAAAU | GUCGGUCGGG | GAAGAUGUAU | UCUUCUCAUA | AGAUAUAGUC | GGACCUCUCC | 300 |
| UUAAUGGGAG | CUAGCGGAUG | AAGUGAUGCA | ACACUGGAGC | CGCUGGGAAC | UAAUUUGUAU | 360 |
| GCGAAAGUAU | AUUGAUUAGU | UUUGGAGUAC | UCG | | | 393 |

( 2 ) INFORMATION FOR SEQ ID NO:2:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:2:

NNNNA        5

( 2 ) INFORMATION FOR SEQ ID NO:3:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:3:

AACAA        5

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:4:

AGUUACCAGG  CAUGCACCUG  GUAGUCA        27

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:5:

GUCUUUAAAC  CAAUAGAUUG  GAUCGGUUUA  AAAGGC        36

( 2 ) INFORMATION FOR SEQ ID NO:6:

( i ) SEQUENCE CHARACTERISTICS:

( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TTTATTTATT TATTT 15

( 2 ) INFORMATION FOR SEQ ID NO:7:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CTGCAGAATT CTAATACGAC TCACTATAGG AGGGAAAAGT TATCAGGC 48

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CGAGTACTCC AAAACTAATC 20

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GTAAAACGAC GGCCAGT 17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CATGATTACG AATTCTA 17

( 2 ) INFORMATION FOR SEQ ID NO:11:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: misc_feature
    ( B ) LOCATION: 8
    ( D ) OTHER INFORMATION: /label=NH2
        / note="NH2 SIGNIFIES THAT THE T HAS BEEN MODIFIED
        AND IS 3'- AMINO'3'DEOXYTHYMIDINE-5'-TRIPHOSPHATE"

( x i ) SEQUENCE DESCRIPTION: SEQ ID NO:11:

GGCCCTCT       8

( 2 ) INFORMATION FOR SEQ ID NO:12:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GGCCCTC       7

( 2 ) INFORMATION FOR SEQ ID NO:13:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: modified_base
        ( B ) LOCATION: 8
        ( D ) OTHER INFORMATION: /mod_base=OTHER
            / label=ARG
            / note="ARG SIGNIFIES THAT THE AMINO ACID ARGININE
            IS COVALENTLY LINKED TO..."

( x i ) SEQUENCE DESCRIPTION: SEQ ID NO:13:

GGCCCTCT       8

( 2 ) INFORMATION FOR SEQ ID NO:14:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: modified_base
        ( B ) LOCATION: 8
        ( D ) OTHER INFORMATION: /mod_base=OTHER
            / label=ARGARG
            / note="ARGARG SIGNIFIES THAT THE T HAS THE AMINO
            ACID ARGININE COVALENTLY LINKED TO IT AND THAT A
            SECOND ARGININE IS COVALENTLY LINKED TO THE FIRST ( x i ) SEQUENCE DESCRIPTION: SEQ ID NO:14:

GGCCCTCT       8

( 2 ) INFORMATION FOR SEQ ID NO:15:

( i ) SEQUENCE CHARACTERISTICS:
        ( A ) LENGTH: 17 base pairs ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GGCCCTCTAT TTATTTA 17

( 2 ) INFORMATION FOR SEQ ID NO:16:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GGCCCTCT 8

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GGCCCTCTAA ATAAATAAAT AAA 23

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 6
        ( D ) OTHER INFORMATION: /label=N
            / note="N SIGNIFIES A NUCLEOTIDE ANALOG"

( x i ) SEQUENCE DESCRIPTION: SEQ ID NO:18:

CCCTCNAAAT AAATAAATAA A 21

( 2 ) INFORMATION FOR SEQ ID NO:19:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 6
        ( D ) OTHER INFORMATION: /label=N
            / note="N SIGNIFIES A NUCLEOTIDE ANALOG"

( x i ) SEQUENCE DESCRIPTION: SEQ ID NO:19:

CCCTCN 6

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:20:

GGCCCUCUAU UUAUUUA 17

*T. THERMOPHILA* GROUP I INTRONS THAT CLEAVE AMIDE BONDS

This invention was made with government support under NASA Grant No. NAGW-2881. The government has certain rights in the invention.

CROSS REFERENCE TO RELATED APPLICATION

The present application is a continuation-in-part of copending U.S. application Ser. No. 08/242,402, filed May 13, 1994.

TECHNICAL FIELD

The present invention relates to nucleic acid enzymes or enzymatic RNA molecules that are capable of cleaving a variety of bonds, including phosphodiester bonds and amide bonds, in a variety of substrates. Thus, the disclosed enzymatic RNA molecules are capable of functioning as nucleases or peptidases. The present invention also relates to compositions containing the disclosed enzymatic RNA molecules and to methods of making and using such enzymes and compositions.

BACKGROUND

The need for catalysts that operate outside of their native context or which catalyze reactions that are not represented in nature has resulted in the development of "enzyme engineering" technology. The usual route taken in enzyme engineering has been a "rational design" approach, relying upon the understanding of natural enzymes to aid in the construction of new enzymes. Unfortunately, the state of proficiency in the areas of protein structure and chemistry is insufficient to make the generation of novel biological catalysts routine.

Recently, a different approach for developing novel catalysts has been applied. This method involves the construction of a heterogeneous pool of macromolecules and the application of an in vitro selection procedure to isolate molecules from the pool that catalyze the desired reaction. Selecting catalysts from a pool of macromolecules is not dependent on a comprehensive understanding of their structural and chemical properties. Accordingly, this process has been dubbed "irrational design" (Brenner and Lerner, *PNAS USA* 89: 5381-5383 (1992)).

The process of Darwinian evolution, by which enzymes arise in nature, does not operate by generating a diverse population of variants and harvesting the most advantageous individuals. In biological systems, diversity is maintained by ongoing mutations, and the population is shaped by selection. Novel mutations augment existing variation, so that the evolutionary search is biased, in an appropriate fashion, by selection events that have already occurred (Eigen, et al., *J. Phys. Chem.* 92: 6881 (1988)). The more advantageous mutants, which are relatively abundant in the population, give rise to larger numbers of novel variants when compared to the less advantageous mutants.

Most efforts to date involving the rational design of enzymatic RNA molecules or ribozymes have not led to molecules with fundamentally new or improved catalytic function. However, the application of irrational design methods via a process we have described as "directed molecular evolution" or "in vitro evolution", which is patterned after Darwinian evolution of organisms in nature, has the potential to lead to the production of RNA molecules that have desirable functional characteristics.

This technique has been applied with varying degrees of success to RNA molecules in solution (see, e.g., Mills, et al., *PNAS USA* 58: 217 (1967); Green, et al., *Nature* 347: 406 (1990); Chowrira, et al., *Nature* 354: 320 (1991); Joyce, *Gene* 82: 83 (1989); Beaudry and Joyce, *Science* 257: 635-641 (1992); Robertson and Joyce, *Nature* 344: 467 (1990)), as well as to RNAs bound to a ligand that is attached to a solid support (Tuerk, et al., *Science* 249: 505 (1990); Ellington, et al., *Nature* 346: 818 (1990)). It has also been applied to peptides attached directly to a solid support (Lam, et al., *Nature* 354: 82 (1991)); and to peptide epitopes expressed within a viral coat protein (Scott, et al., *Science* 249: 386 (1990); Devlin, et al., *Science* 249: 249 (1990); Cwirla, et al., *PNAS USA* 87: 6378 (1990)).

Therefore, in this context, the discoveries and inventions disclosed herein are particularly significant, in that they highlight the potential of in vitro evolution as a means of designing increasingly more efficient catalytic molecules.

BRIEF SUMMARY OF THE INVENTION

We have achieved a considerable degree of success in engineering new enzymatically active oligonucleotide molecules. Not only are the within-disclosed techniques useful in the design, identification and use of enzymatically active RNA molecules with improved specificities, reaction rates, and substrate binding capabilities, to name a few examples, success has now been achieved in designing oligonucleotide molecules that cleave bonds other than, or in addition to, phosphodiester bonds generally linking adjacent nucleotides in oligonucleotide molecules.

In particular, the present invention discloses enzymatic RNA molecules having peptidase activity. Enzymatic RNA molecules of the present invention are thus capable of functioning as nucleophiles, cleaving phosphodiester bonds, amide bonds, or both.

Therefore, the present invention contemplates enzymatic RNA molecules capable of specifically cleaving amide bonds, wherein the enzymatic RNA molecules include one or more point mutations which improve the enzymatic performance of the enzymatic RNA molecules. In various embodiments, the enzymatic RNA molecule further includes one or more point mutations which affect the substrate specificity of the enzymatic RNA molecule. In one variation, the enzymatic performance comprises catalytic efficiency. It is also contemplated that enzymatic performance may comprise substrate binding affinity. In various embodiments, the substrate may comprise a polypeptide or protein.

Still other embodiments contemplate enzymatic RNA molecules wherein enzymatic performance comprises substrate specificity. In various embodiments, that specificity is changed via altering the recognition sequence. As noted above, substrates may comprise a polypeptide or protein.

The present invention contemplates enzymatic RNA molecules that cleave amide bonds. In one embodiment, the enzymatic RNA molecule is derived from a group I, II, III, or IV intron. In one variation, the group I intron is derived from a group I intron; in another variation, the group I intron is derived from the group I intron of *Tetrahymena thermophila* precursor rRNA. In another embodiment, an enzymatic RNA molecule of the present invention is derived from the molecule identified herein as SEQ ID NO 1.

In another variation, an enzymatic RNA molecule contemplated herein comprises the portions of a group I, II, III or IV intron having catalytic activity. In an alternative embodiment, an enzymatic RNA molecule comprises the portions of a Tetrahymena group I intron having catalytic activity. In yet-another embodiment, an enzymatic RNA molecule of the present invention is derived from an L-19 or L-21 RNA molecule and includes the portions of the L-19 or L-21 RNA molecule having catalytic activity.

The present invention further contemplates enzymatic RNA molecules including one or more mutations. Various embodiments of the disclosed invention contemplate that an enzymatic RNA molecule of the present invention includes one or more mutations not typically found in wild type enzymatic RNA molecules or ribozymes.

In various embodiments, enzymatic RNA molecules of the present invention include one or more of the following mutations: 44:G→A; 51/52:insert AGAA; 87:A→deleted; 94:A→U; 94:A→C; 115:A→U; 116:G→A; 138:C→A; 166:C→A; 167:U→G; 170:C→U; 188:G→A; 190:U→A; 191:G→U; 205:U→C; 215:G→A; 239:U→A; 258:U→C; 312:G→A; 313:G→U; 313:G→C; 314:A→G; 317:U→G; 317:U→C 317:U→A; 333:U→C; 350:C→U; and 364:C→U. In various alternative embodiments, an enzymatic RNA molecule of the present invention has 1–4 point mutations, 5–8 point mutations, 9–12 point mutations, or 13 or more point mutations.

Other examples of combinations of mutations which may be present in enzymatic RNA molecules of the present invention include the following: (a) 98:C→U and 313–314:GA→UG; (b) 98:C→U, 205:U→C, and 317:U→R; (c) 94:A→Y and 215:G→A; (d) 94; :A→Y, 205:U→C, and 313–314:GA→UG; (e) 94:A→Y, 98:C→U, and 333:U→C; (f) 44:C→A, 94:A→U, 115:A→U, 116:G→A, 138:C→A, 188:G→A, 190:U→A, 191:G→U, 205:U→C, 215:G→A, 312:G→A, and 317:U→G; (g) 44:G→A, 94:A→U, 115:A→U, 116:G→A, 138:C→A, 167:U→G, 188:G→A, 190:U→A, 191:G→U, 205:U→C, 215:G→A, 239:U→A, and 312:G→A; (h) 44:G→A, 51/52:insert AGAA, 87:A→del, 94:A→U, 115:A→U, 116:G→A, 166:C→A, 170:C→U, 188:G→A, 190:U→A, 191:G→U, 205:U→C, 215:G→A, 239:U→A, 312:G→A, 350:C→U, and 364:C→U; or (i) 44:G→A, 51/52:insert AGAA, 87:A→del, 94:A→U, 115:A→U, 116:G→A, 166:C→A, 170:C→U, 188:G→A, 190:U→A, 191:G→U, 205:U→C, 215:G→A, 313:G→C, and 314:A→G.

The present invention further contemplates an enzymatic RNA molecule capable of specifically cleaving amide bonds, wherein the enzymatic RNA molecule includes one or more point mutations which affect the enzymatic performance of the molecule. In other variations, an enzymatic RNA molecule of the present invention includes one or more point mutations which improve the substrate specificity of the molecule. In alternative embodiments, an enzymatic RNA molecule of the present invention includes one or more mutations which improve enzymatic performance and substrate specificity. In an alternative embodiment, an enzymatic RNA molecule capable of specifically cleaving amide bonds is disclosed, wherein the enzymatic RNA molecule includes one or more point mutations which affect the enzymatic performance or substrate specificity of the molecule.

In one variation, the enzymatic performance comprises catalytic efficiency. It is also contemplated that enzymatic performance may comprise substrate binding affinity. Still other embodiments contemplate enzymatic RNA molecules wherein enzymatic performance comprises substrate specificity. In various embodiments, that specificity is changed via altering the recognition sequence.

The present invention further contemplates a ribozyme amidase intermediate comprising a ribonucleotide polymer including a 5′ terminal nucleotide with a ribose sugar having a 2′ hydroxyl, and a peptide having one or more amino acid residues including a carboxy terminal amino acid residue, the carboxy terminal amino acid residue being covalently linked by an ester bond to the 2′ hydroxyl of the ribonucleotide polymer. In one alternative embodiment, the ester bond is chemically unstable under physiological conditions. In another, the ester bond is acid labile. The invention further contemplates embodiments whereby the ribonucleotide polymer has a catalytic activity for hydrolyzing the ester bond.

In yet another variation, the present invention contemplates a ribozyme amidase intermediate comprising a ribonucleotide polymer; a cofactor including a guanine nucleotide having a ribose sugar with a 2′ hydroxyl; and a peptide having one or more amino acid residues including a carboxy terminal amino acid residue, the carboxyl terminal amino acid residue being covalently linked by an ester bond to the 2′ hydroxyl of the guanine nucleotide.

The invention also discloses an enzymatic RNA molecule comprising a ribonucleotide polymer having a catalytic activity for hydrolyzing an amide substrate to produce an amino cleavage product and a ribozyme amidase intermediate. In one variation, the ribonucleotide polymer has a 5′ terminal nucleotide with a ribose sugar having a nucleophilic 2′ hydroxyl, and the ribozyme amidase intermediate includes an ester linkage between the nucleophilic 2′ hydroxyl and a carboxy group of the amide substrate. In another variation, the 5′ terminal nucleotide includes a guanine base.

The present invention also discloses enzymatic RNA molecules wherein the amide substrate includes a peptide having one or more amino acid residues including a carboxy terminal amino acid residue bearing the carboxy group of the amide substrate, the carboxy terminal amino acid residue being covalently linked by the ester linkage to the 2′ hydroxyl of the ribonucleotide polymer. In an alternative embodiment, the ribonucleotide polymer has an effective binding affinity for the amide substrate and lacks an effective binding affinity for the amino cleavage product. In another variation, the catalytic activity of the ribonucleotide polymer is dependent upon the presence of divalent ions. An alternative embodiment contemplates that an enzymatic RNA molecule as disclosed herein further comprises a cofactor bound to the ribonucleotide polymer, the cofactor including a guanine nucleotide having a ribose sugar with a nucleophilic 2′ hydroxyl capable of forming an acid labile ester intermediate with the carboxy cleavage product.

The present invention also contemplates various methods of making and using enzymatic RNA molecules according to the present invention. In one embodiment, a method of selecting an enzymatic RNA molecule that cleaves amide bonds, comprising the following consecutive steps: (a) obtaining a population of ribozymes; (b) admixing amide bond-containing substrate molecules with the population of ribozymes to form an admixture; (c) maintaining the admixture for a sufficient period of time and under predetermined reaction conditions to allow the ribozymes and the substrate to interact and form ribozyme-product complexes; (d) isolating any ribozyme-product complexes that form; (e) allowing the ribozyme-product complex to dissociate into separate ribozyme and product; and (f) separating the ribozymes from the product.

In other variations of the aforementioned method, the substrate is tagged with an immobilizing agent. In one embodiment, the agent comprises biotin. In another embodiment, a solid surface incorporated or tagged with avidin is utilized to assist in the process of isolating ribozyme-product complexes. For example, the isolating step may further comprise exposing the ribozyme-product complex to a solid surface having avidin linked thereto, whereby the complex becomes attached to the solid surface.

The present invention further contemplates methods of cleaving an amide bond. In one variation, the method comprises admixing an enzymatic RNA molecule with an amide bond-containing substrate, to form a reaction admixture, and maintaining the admixture under predetermined reaction conditions to allow the enzymatic RNA molecule to cleave the amide bond. In an alternative embodiment, the enzymatic RNA molecule is able to cleave an amide bond at a preselected site. Methods of cleaving amide bonds as disclosed herein may also comprise the steps of separating the products from the enzymatic RNA molecule; and adding additional substrate to the enzymatic RNA molecule to form a new reaction admixture.

Also contemplated herein are methods of engineering enzymatic RNA molecules that cleave amide bonds. In one embodiment, the method comprises the following steps: (a) obtaining a population of ribozymes; (b) introducing genetic variation into the population to produce a variant population; (c) selecting individuals from the variant population that meet predetermined selection criteria; (d) separating the selected individuals from the remainder of the variant population; and (e) amplifying the selected individuals.

In another variation, methods of catalytically hydrolyzing an amide substrate are contemplated. In one embodiment, the method comprises the following step A: contacting the amide substrate with a ribozyme comprising a ribonucleotide polymer having a catalytic activity for hydrolyzing the amide substrate and producing an amino cleavage product and a ribozyme amidase intermediate, the ribozyme amidase intermediate including a carboxyl of the amide substrate bonded by an ester bond to a 2' hydroxyl of a ribose sugar on a 5' terminal nucleotide of the ribonucleotide polymer. In another variation, the method further comprises step B as follows, to be performed after Step A: hydrolyzing the ester bond of the ribozyme amidase intermediate to produce a carboxy cleavage product.

In another embodiment, the method further comprises providing the enzymatic RNA molecule in a reaction medium at a concentration sufficient to cause cleavage of about one molecule of substrate per molecule of enzymatic RNA per minute. In yet another embodiment, the method further comprises providing the enzymatic RNA molecule in a reaction medium, wherein the enzymatic RNA molecule is present at a concentration sufficient to cause cleavage of at least 10% of a population of substrate molecules in an hour.

The invention also contemplates a method of producing an enzymatic RNA molecule having a predetermined catalytic activity, comprising the following steps: (a) subjecting a population of enzymatic RNA molecules to mutagenizing conditions to produce a diverse population of mutant RNA molecules; (b) selecting an enzymatic RNA molecule having a predetermined activity from the diverse population of mutant enzymatic RNA molecules; and (c) separating the RNA molecule from the diverse population of mutant RNA molecules. In various embodiments, the predetermined activity comprises the ability to cleave amide or peptide bonds.

In one alternative method, the mutagenizing conditions comprise conditions that introduce defined or random nucleotide substitutions within an enzymatic RNA molecule. In another variation, the mutagenizing conditions comprise chemical modification, incorporation of randomized mutagenic oligodeoxynucleotides, or inaccurate copying by a polymerase. In yet another variation, the mutagenizing conditions comprise use of site-directed mutagenesis, polymerase chain reaction (PCR), mutagenic PCR, or self-sustained sequence replication.

Another variation of the foregoing methods further comprises the step of amplifying the enzymatic RNA molecules selected from the diverse population. In one embodiment, the amplifying is performed using a polymerase chain reaction, preferably a mutagenic polymerase chain reaction. In another embodiment, the amplifying is performed using self-sustained sequence replication.

The present invention also discloses various compositions. In one embodiment, a composition including an enzymatic RNA molecule that cleaves amide bonds is disclosed. In another variation, a composition including an enzymatic RNA molecule comprising a ribonucleotide polymer having a catalytic activity for hydrolyzing an amide substrate to produce an amino cleavage product and a ribozyme amidase intermediate is disclosed. In another embodiment, a composition further comprises a cofactor bound to the ribonucleotide polymer, the cofactor including a guanine nucleotide having a ribose sugar with a nucleophilic 2' hydroxyl capable of forming an acid labile ester intermediate with the carboxy cleavage product.

Also contemplated by the within invention are compositions comprising two or more populations of enzymatic RNA molecules having characteristics as disclosed herein and in the claims. In another variation, each population of enzymatic RNA molecules in the composition is capable of recognizing a different substrate.

BRIEF DESCRIPTION OF THE DRAWINGS

In FIG. 2A, the overall procedure for RNA amplification is shown. "RT"= reverse transcriptase; "T7 pol"=T7 polymerase; "prom"= promoter, and "RNA" represents the enzymatic RNA molecule. In FIG. 2B, the procedure for selective amplification based on phosphoester transfer activity of a group I ribozyme is shown. "E" represents the enzymatic RNA molecule; "S" represents substrate; "E.S" represents enzyme/substrate complex; and "EP" represents enzyme/product complex.

DETAILED DESCRIPTION

A. Definitions

Figure 1:
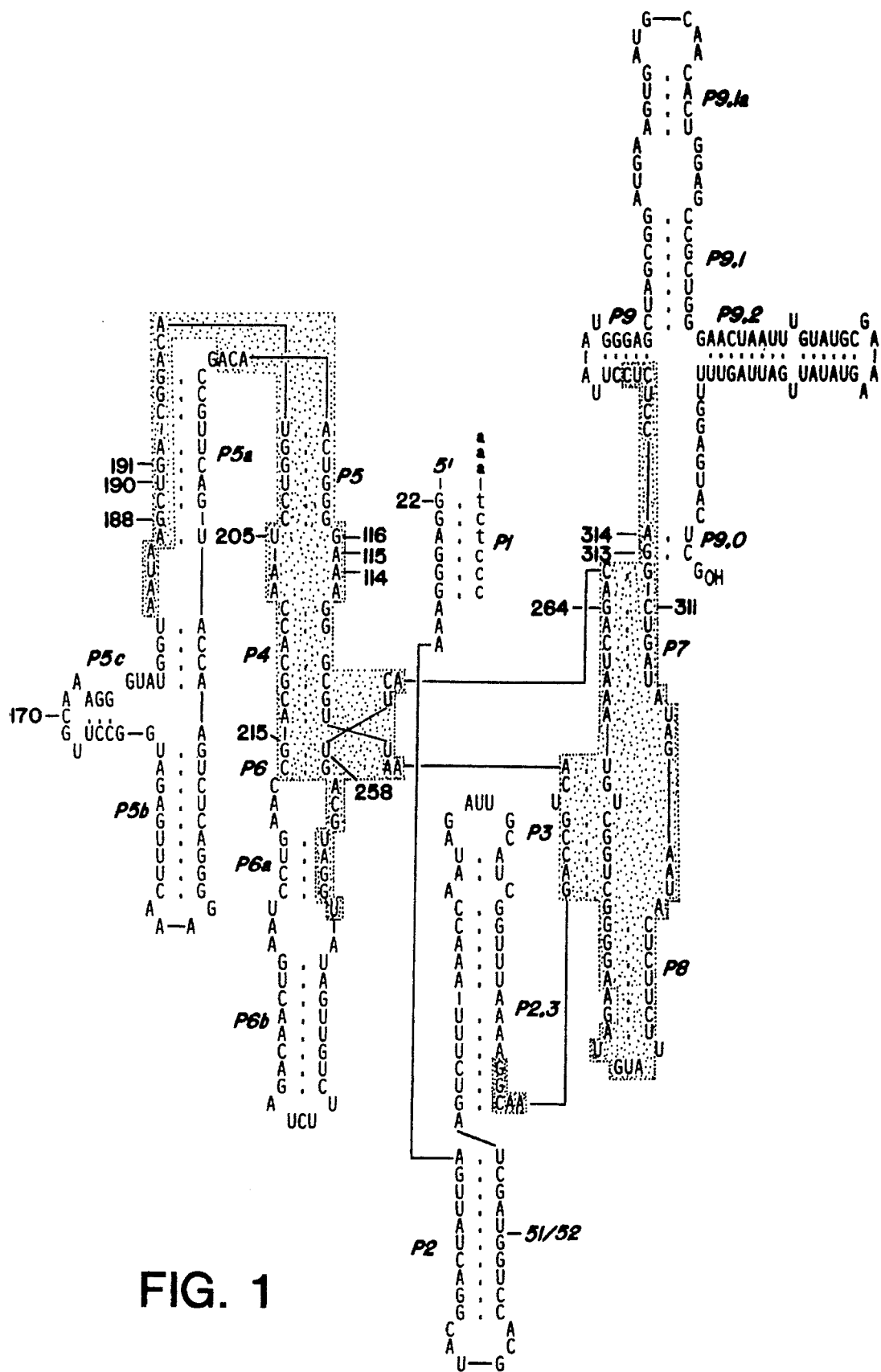
FIG. 1 illustrates the secondary structure of the wild-type Tetrahymena ribozyme (L-21 form; SEQ ID NO 1). Paired structural elements are designated by Pi. Joining regions between paired elements i and j, referred to as J i/j, are not labeled. Nucleotide positions that were partially randomized in the initial population are indicated by shaded regions. The internal guide sequence (IGS) is shown in bold, and the DNA substrate is shown in lowercase letters. Nucleotide positions discussed in the text are labeled.

As used herein, the term "amino acid residue" generally means an amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 C.F.R. §1.822 (b) (2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |

-continued

TABLE OF CORRESPONDENCE

| SYMBOL | | |
|---|---|---|
| 1-Letter | 3-Letter | AMINO ACID |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxy-terminus. In addition, the phrase "amino acid residue" is broadly defined to include the amino acids listed in the Table of Correspondence and modified and unusual amino acids, such as those listed in 37 C.F.R. §1.822 (b) (4), and incorporated herein by reference. Furthermore, it should be noted that a dash at the beginning or end of an amino acid residue sequence indicates a peptide bond to a further sequence of one or more amino acid residues or to an amino-terminal group such as NH$_2$ or to a carboxy-terminal group such as COOH.

The term "conservative substitution" as used herein is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like. The term "conservative substitution" also includes the use of a substituted amino acid in place of an unsubstituted parent amino acid provided that such a polypeptide also displays the requisite binding activity.

In some instances, the replacement of an ionic residue by an oppositely charged ionic residue such as Asp by Lys has been termed conservative in the art in that those ionic groups are thought to merely provide solubility assistance. In general, however, since the replacements discussed herein are on relatively short synthetic polypeptide antigens, as compared to a whole protein, replacement of an ionic residue by another ionic residue of opposite charge is considered herein to be a "radical replacement", as are replacements between nonionic and ionic residues, and bulky residues such as Phe, Tyr or Trp and less bulky residues such as Gly, Ile and Val.

The term "correspond" in its various grammatical forms is used herein and in the claims in relation to polypeptide sequences to mean the polypeptide sequence described plus or minus up to three amino acid residues at either or both of the amino- and carboxy-termini and containing only conservative substitutions in particular amino acid residues along the polypeptide sequence.

As used herein, "polypeptide" and "peptide" are terms used interchangeably herein to designate a series of no more than about 50 amino acid residues connected one to the other by peptide bonds between the alpha-amino and carboxy groups of adjacent residues.

As used herein, the terms "peptide bond" and "amide bond" may be used interchangeably herein, and include amide linkages such as those typically found within polypeptides or proteins. As used herein, it is not necessary that an amide bond or peptide bond link adjacent amino acid residues only; for example, peptide bonds/amide bonds as described herein may be found linking adjacent nucleotides, adjacent amino acids, or linking an amino acid to a nucleotide.

The term(s) may also be considered to encompass linkages akin to those including unactivated alkyl amides, as opposed to activated aryl amides.

"Protein" is a term generally used herein to designate a series of greater than 50 amino acid residues connected one to the other as in a polypeptide.

As used herein, the term "ribozyme" is used to describe an RNA-containing nucleic acid that is capable of functioning as an enzyme. In the present disclosure, the term "ribozyme" includes endoribonucleases and endodeoxyribonucleases, as well as amide bond-cleaving nucleic acid enzymes of the present invention. Other terms used interchangeably with ribozyme herein are "enzymatic RNA molecule" or "catalytic RNA molecule", which should be understood to include ribozymes and enzymatically active portions thereof, whether derived from Tetrahymena or from other organisms or sources.

The term "enzymatic RNA molecules" also includes RNA molecules which have complementarity in a substrate-binding region to a specified oligonucleotide target or substrate; it also has an enzymatic activity which is active to specifically cleave the oligonucleotide substrate. Stated in another fashion, the enzymatic RNA molecule is capable of cleaving the oligonucleotide substrate intermolecularly. This complementarity functions to allow sufficient hybridization of the enzymatic RNA molecule to the substrate oligonucleotide to allow the intermolecular cleavage of the substrate to occur. While one-hundred percent (100%) complementarity is preferred, complementarity in the range of 75–100% is also useful and contemplated by the present invention.

Enzymatic RNA molecules of the present invention may alternatively be described as having amide-cleaving, amide bond-cleaving, amidase, peptidase, or protease activity. These terms may be used interchangeably herein.

The term "enzymatic nucleic acid" as used herein encompasses enzymatic RNA or DNA molecules, enzymatic RNA-DNA polymers, and enzymatically active portions or derivatives thereof, although enzymatic RNA molecules are a particularly preferred class of enzymatically active molecules according to the present invention.

The term "endodeoxyribonuclease", as used herein, is an enzyme capable of cleaving a substrate comprised predominantly of DNA. The term "endoribonuclease", as used herein, is an enzyme capable of cleaving a substrate comprised predominantly of RNA.

As used herein, the term "base pair" (bp) is generally used to describe a partnership of adenine (A) with thymine (T) or uracil (U), or of cytosine (C) with guanine (G), although it should be appreciated that less-common analogs of the bases A, T, C, and G may occasionally participate in base pairings. Nucleotides that normally pair up when DNA or RNA adopts a double stranded configuration may also be referred to herein as "complementary bases".

"Complementary nucleotide sequence" generally refers to a sequence of nucleotides in a single-stranded molecule of DNA or RNA that is sufficiently complementary to that on another single oligonucleotide strand to specifically hybridize to it with consequent hydrogen bonding.

"Nucleotide" generally refers to a monomeric unit of DNA or RNA consisting of a sugar moiety (pentose), a phosphate group, and a nitrogenous heterocyclic base. The base is linked to the sugar moiety via the glycosidic carbon (1' carbon of the penrose) and that combination of base and sugar is a "nucleoside". When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus, unless otherwise specified.

"Nucleotide analog" generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different sugars, or a combination of the two. A listing of exemplary analogs wherein the base has been altered is provided in section C hereinbelow.

"Oligonucleotide or polynucleotide" generally refers to a polymer of single- or double-stranded nucleotides. As used herein, "oligonucleotide" and its grammatical equivalents will include the full range of nucleic acids. An oligonucleotide will typically refer to a nucleic acid molecule comprised of a linear strand of ribonucleotides. The exact size will depend on many factors, which in turn depends on the ultimate conditions of use, as is well known in the art.

As used herein, the term "physiologic conditions" is meant to suggest reaction conditions emulating those found in mammalian organisms, particularly humans. While variables such as temperature, availability of cations, and pH ranges may vary as described in greater detail below, "physiologic conditions" generally comprise a temperature of about 35°–40° C., with 37° C. being particularly preferred, as well as a pH of about 7.0–8.0, with 7.5 being particularly preferred, and further comprise the availability of cations, preferably divalent or monovalent cations, in a concentration of about 5–15 mM, with a concentration of about 10 mM being particularly preferred. "Physiologic conditions", as used herein, may optionally include the presence of free $G_{OH}$. As noted previously, preferred conditions are described in greater detail below.

B. Enzymatic Nucleic Acid Molecules

Some genes have their coding sequences interrupted by stretches of non-coding DNA. These non-coding sequences are generally termed introns. To produce a mature transcript from these genes, the primary RNA transcript (precursor RNA) must undergo a cleavage-ligation reaction termed RNA splicing. This RNA splicing produces the mature transcript of the polypeptide coding messenger RNA (mRNA), ribosomal RNA, or transfer RNA (tRNA). Introns are grouped into four categories (groups I, II, III, and IV) based on their structure and the type of splicing reaction they undergo.

RNA molecules capable of cleaving other RNA molecules have recently been described. Such RNA-cleaving RNA molecules, which may also be referred to as ribozymes or enzymatic RNA molecules, may be chosen from group I, II, III, or IV introns, with group I and II introns being of greatest interest. Other enzymatic RNA molecules of interest herein are those formed in ribozyme motifs known in the art as "hammerhead" and "hairpin". Enzymatic RNA molecules of interest herein also include hepatitis delta virus ribozymes and RNaseP or RNaseP-like RNA.

Of particular interest to the present invention are the group I introns. Group I introns undergo an intra-molecular RNA splicing reaction leading to cyclization that does not require protein cofactors, Cech, *Science* 236: 1532–1539 (1987). (The disclosures of all references cited within this application are incorporated by reference herein, where appropriate.)

The group I introns, including the intron isolated from the large ribosomal RNA precursor of *Tetrahymena thermophila*, catalyze a sequence-specific phosphoester transfer reaction involving RNA substrates. Zaug and Cech, *Science* 229: 1060–1064 (1985); and Kay and Inoue, *Nature* 327: 343–346 (1987). This sequence-specific phosphoester transfer reaction leads to the removal of the group I intron from the precursor RNA and to ligation of two exons in a process known as RNA splicing. The splicing reaction catalyzed by group I introns proceeds via a two-step transesterification mechanism. The details of this reaction have been reviewed by Cech, *Science* 236: 1532–1539 (1987).

The splicing reaction of group I introns is initiated by the binding of guanosine or a guanosine nucleotide to a site within the group I intron structure. Attack at the 5' splice site by the 3'-hydroxyl group of guanosine results in the covalent linkage of guanosine to the 5' end of the intervening intron sequence. This reaction generates a new 3'-hydroxyl group on the uridine at the 3' terminus of the 5' exon. The 5' exon subsequently attacks the 3' splice site, yielding spliced exons and the full-length linear form of the group I intron.

The linear group I intron usually cyclizes following splicing. Cyclization occurs via a third transesterification reaction, involving attack of the 3'-terminal guanosine at an interval site near the 5' end of the intron. The group I introns also undergo a sequence-specific hydrolysis reaction at the splice site sequences as described by Inoue et al., *J. Mol. Biol.* 189: 143–165 (1986). This activity has been used to cleave RNA substrates in a sequence-specific manner by Zaug et al., *Nature* 324: 429–433 (1986).

The structure of group I introns has been reviewed by J. Burke, *Gene* 73: 273–294 (1988). The structure is characterized by nine base paired regions, termed P1–P9. (See, e.g., Burke et al., *Nucleic Acids Res.* 15: 7217–7221 (1987).) The folded structure of the intron is clearly important for the catalytic activity of the group I introns, as evidenced by the loss of catalytic activity under conditions where the intron is denatured. In addition, mutations that disrupt essential base-paired regions of the group I introns result in a loss of catalytic activity. Burke, *Gene* 73: 273–294 (1988). Compensatory mutations or second-site mutations that restore base-pairing in these regions also restore catalytic activity. Williamson et al., *J. Biol. Chem.* 262: 14672–14682 (1987); and Burke, *Gene* 73: 273–294 (1988).

Several different deletions that remove a large nucleotide segment from the group I introns (FIG. 1) without destroying its ability to cleave RNA have been reported. Burke, *Gene* 73: 273–294 (1988). However, attempts to combine large deletions have resulted in both active and inactive introns. Joyce et al., *Nucleic Acid Res.* 17: 7879 (1989).

The Tetrahymena ribozyme is a self-splicing group I intron derived from the large ribosomal RNA (rRNA) precursor of *Tetrahymena thermophila*. Its biological function is to catalyze its own excision from precursor rRNA to produce mature rRNA. This function has been expressed in vitro (Kruger, et al., *Cell* 31: 147 (1982)) and has been generalized to include various phosphoester transfer reactions involving RNA substrates (Zaug, et al., *Science* 231: 470 (1986); Kay, et al., *Nature* 327: 343 (1987); Been, et al., *Science* 239: 1412 (1988); Woodson, et al., *Cell* 57: 335 (1989); Doudna, et al., *Nature* 339: 519 (1989)). For example, the ribozyme has been used as a sequence-specific endoribonuclease (Zaug, et al., Id. (1986); Murphy, et al., *PNAS USA* 86: 9218 (1989)), a reaction that proceeds with high catalytic efficiency ($k_{cat}/K_m = 10^8 M^{-1}$ min$^{-1}$) (Herschlag, et al., *Biochemistry* 29: 10159 (1990)).

The within-described examples utilize derivatives of the self-splicing group I intron of *Tetrahymena thermophila*, a ribozyme that is able to catalyze sequence-specific cleavage of single-stranded RNA via a phosphoester transfer mechanism (Zaug and Cech, *Science* 231: 470–475 (1986); Zaug et al., *Nature* 324: 429–433 (1986)), although it is expressly to be understood that the invention is not limited to these embodiments. The Tetrahymena ribozyme consists of 413 nucleotides and assumes a well-defined secondary and tertiary structure that is responsible for its catalytic activity (Burke, et al., *Nucleic Acids Res.* 15: 7217 (1987); Kim, et al., *PNAS USA* 84: 8788 (1987); Celander, et al., *Science* 251: 401 (1991); Michel, et al., *J. Mol. Biol.* 216: 585 (1990). (See FIG. 1 for a general diagram.) Phylogenetic analysis, supported by site-directed mutagenesis and deletion studies, points out a distinction between a conserved catalytic core (comprising about one-third of the molecule) and surrounding stem-loop elements that offer structural support but are not essential for catalytic activity. (See Davies, et al., *Nature* 300: 719 (1982); Michel, et al., *Biochimie* 64: 867 (1982); Michel, et al., *EMBO J.* 2: 33 (1983); Cech, et al., *Gene* 73: 259 (1988); Price, et al., *Nucl. Acids Res.* 13: 1871 (1985); Szostak, et al., *Nature* 322: 83 (1986); Joyce, et al., *Nucl. Acids Res.* 15: 9825 (1987); Barfod, et al., *Genes Dev.* 2: 652 (1988); Joyce, et al., *Nucleic Acids Res.* 17: 7879 (1989); Couture, et al., *J. Mol. Biol.* 215: 345 (1990); Beaudry and Joyce, *Biochemistry* 29: 6534 (1990).)

The ribozyme contains a template region, referred to as the "internal guide sequence" (IGS), which lies at the 5' end of the molecule and forms Watson-Crick base pairs with the target RNA substrate. The 3'-OH of guanosine, including a guanosine residue that lies at the 3' end of the ribozyme, is directed to attack a particular phosphoester bond within the ribozyme-bound substrate. A phosphoester transfer reaction ensues, resulting in cleavage of the substrate at a position immediately downstream from the region of base pairing, and concomitant ligation of the 3' portion of the substrate to the 3' oxygen of the attacking guanosine. The wild-type Tetrahymena ribozyme can cleave a single-stranded DNA substrate with low efficiency under conditions of high magnesium concentration (50 mM MgCl$_2$) and/or high temperature (50° C.) (Herschlag and Cech, *Nature* 344: 405–409 (1990a); Robertson and Joyce, *Nature* 344: 467–468 (1990)). Under more physiologic conditions (e.g. 37° C., 10 mM MgCl$_2$, pH 7.5), however, the DNA-cleavage reaction is almost undetectable.

The Tetrahymena ribozyme can also act as a sequence-specific endodeoxyribonuclease (Robertson and Joyce, Id. (1990)), although the efficiency of DNA cleavage is low ($k_{cat}/K_m = 200 M^{-1}$ min$^{-1}$, determined at 50° C., 10 mM MgCl$_2$) (Herschlag, et al., *Nature* 344: 405 (1990)). The efficiency of RNA-catalyzed DNA cleavage under physiologic conditions is even lower ($k_{cat}/K_m = 36 M^{-1}$ min$^{-1}$, determined at 37° C., 10 mM MgCl$_2$).

FIG. 1 illustrates the secondary structure of the *Tetrahymena thermophila* pre-rRNA intron, with the recognition sequence and the core structure that is the most conserved region among group I introns shown in bold. The nomenclature used to denote various structural features is the standard nomenclature (see, e.g., Burke et al., *Nucleic Acids Res.* 15: 7217–7221 (1987). The nine conserved pairing regions, P1–P9, and the various loops are shown. The nucleotide sequence is numbered beginning at the 5' terminus of the molecule.

As illustrated in FIG. 1, the recognition site is located at nucleotide 19 to 27, the first spacer region is located at nucleotides 27 to 28 and 94 to 95, the P3[5'] region is located at nucleotides 96 to 103, the second spacer region is located at nucleotides 104 to 106, the first stem loop is located at nucleotides 107 to 214, the second stem loop is located at nucleotides 215 to 258, the third spacer region is located at nucleotides 259 to 261 and the third stem loop is located at nucleotides 262 to 314.

To date, group I introns have been shown to cleave substrates comprising either RNA, or an RNA-DNA polymer, with cleavage in the latter occurring at the RNA-DNA "junction". Zaug et al., *Science* 231: 470–475 (1986); Sugimoto et al., *Nucleic Acids Res.* 17: 355–371 (1989); and Cech, *Science* 236: 1532–1539 (1987). A DNA segment containing 5 deoxycytosines was shown not to be a cleavage substrate for the Tetrahymena IVS, a group I intron, in Zaug et al., *Science* 231: 470–475 (1986).

Therefore, the identification, enhancement, modification and use of novel enzymatic RNA molecules as disclosed herein is a significant and useful development. The utility of molecules with peptidase or protease activity is well-appreciated. Such molecules are used in products as divergent as medical or pharmaceutical agents, food products, personal care products, and cleaning agents, and in various methods and applications—industrial, environmental, medical, and numerous others—that take advantage of a molecule's ability to cleave bonds between amino acids. Thus, the within-disclosed methods and compositions useful for cleaving amide bonds in a variety of substrates are of particular significance.

The term "enzymatic nucleic acid", as used herein, is used to describe an RNA- and/or DNA-containing nucleic acid that is capable of functioning as an enzyme.

The term "ribozyme" is used to describe an RNA-containing nucleic acid that is capable of functioning as an enzyme. As used herein, the term "ribozyme" may be used interchangeably with "enzymatic RNA molecules". The terms "ribozyme", "enzymatic RNA molecule" and "catalytic RNA molecule" should all be understood to encompass the enzymatically active molecules of the present invention, whether those molecules are described as endoribonucleases, endodeoxyribonucleases, peptidases, amide-cleaving molecules, or some other equivalent description.

An enzymatic RNA molecule of the present invention may be engineered or "evolved" from a wild-type, RNA-cleaving ribozyme via methods which tend to generate either "random" or "non-random" mutations. Examples of methods useful in generating enzymatic RNA molecules that include mutations not normally found in wild-type ribozymes include PCR (polymerase chain reaction), 3SR (self-sustained sequence replication), and site-directed mutagenesis.

Preferably, enzymatic RNA molecules produced as disclosed herein are capable of cleaving an amide bond-containing substrate. In one preferred embodiment, the substrate is a polypeptide, although enzymatic RNA molecules capable of cleaving "hybrid" oligonucleotide-oligopeptide molecules, or oligonucleotides containing one or more amide bonds, are also contemplated. In another preferred variation, an enzymatic RNA molecule of the present invention is able to cleave amide bonds under physiologic conditions. Many enzymatic RNA molecules of the present invention are also capable of cleaving a single-stranded RNA substrate, DNA substrates, or RNA-DNA hybrid substrates.

An enzymatic RNA molecule of the present invention may comprise RNA, modified RNA, RNA-DNA polymer, a modified RNA-DNA polymer, a modified DNA-RNA polymer or a modified RNA-modified DNA polymer. RNA contains nucleotides comprising a ribose sugar and adenine, guanine, uracil or cytosine as the base at the 1' position. Modified RNA contains nucleotides comprising a ribose sugar and adenine, thymine, guanine or cytosine and optionally uracil as the base. An RNA-DNA polymer contains nucleotides containing a ribose sugar and nucleotides containing deoxyribose sugar and adenine, thymine and/or uracil, guanine or cytosine as the base attached to the 1' carbon of the sugar. A modified RNA-DNA polymer is comprised of modified RNA, DNA and optionally RNA (as distinguished from modified RNA). Modified DNA contains nucleotides containing a deoxyribose or arabinose sugar and nucleotides containing adenine, uracil, guanine, cytosine and possibly thymine as the base. A modified DNA-RNA polymer contains modified DNA, RNA and optionally DNA. A modified RNA-modified DNA polymer contains modified RNA-modified DNA, and optionally RNA and DNA.

An enzymatic RNA molecule of the present invention is capable of cleaving an amide bond at a predetermined site. An enzymatic RNA molecule of this invention may also be characterized by a nucleotide sequence defining a recognition site that is contiguous or adjacent to the 5' terminus of the nucleotide sequence, a first spacer region located 3'-terminal to the recognition site, a P3[5'] region located 3'-terminal to the first spacer region, a second spacer region located 3'-terminal to the P3[5'] region, a first stem loop located 3'-terminal to the second spacer region, a second stem loop located 3'-terminal to the first stem loop, a third spacer region located 3-' terminal to the second stem loop, and a third stem loop located 3'-terminal to the third spacer region, the third stem loop comprising a 5' stem portion defining a P3[3'] region capable of hybridizing to the P3[5'] region.

It is also to be understood that an enzymatic RNA molecule of the present invention may comprise enzymatically active portions of a ribozyme or may comprise a ribozyme with one or more mutations, e.g., with one or more loops or spacers absent or modified, as long as such deletions, additions or modifications do not adversely impact the molecule's ability to perform as an enzyme.

The recognition site of an enzymatic RNA molecule of the present invention typically contains a sequence of at least 2 to about 12 bases, preferably about 4 to about 8 bases, which are capable of hybridizing to a complementary sequence of bases within a "hybrid" oligonucleotide-oligopeptide substrate or to a specific sequence of amino acids, thus giving the enzymatic RNA molecule its high sequence specificity. For example, an enzymatic RNA molecule of the present invention constructed with a recognition site base sequence of 3'-GGGAG-5' would be able to recognize the base sequence 5'-CCCTC-3' present within an oligodeoxynucleotide sequence in a hybrid substrate and to cleave the substrate molecule at a predetermined site (see, e.g., Example 2). Similarly, an enzymatic RNA molecule with a recognition sequence of 3'-UCGCC-5' will recognize the target sequence 5'-AGCGG-3' in an oligoribonucleotide sequence in a hybrid substrate.

This same recognition site also allows the enzymatic RNA molecule to cleave hybrid or polypeptide substrates with high sequence specificity. Modification or mutation of the recognition site via well-known methods allows one to alter the sequence specificity of an enzymatic nucleic acid molecule.

For example, a preferred method is described by Cadwell and Joyce, in *PCR Methods and Applications* 2: 28–33 (1992). (Also see Cadwell and Joyce, *PCR Methods and Applications* 3 (Suppl.): S136–S140 (1994).) According to this modified PCR method, random point mutations may be introduced into cloned genes. The method has been used to mutagenize the gene encoding the ribozyme with a mutation rate of 0.66% ±0.13% (95% confidence interval) per position per PCR, as determined by sequence analysis, with no strong preferences observed with respect to the type of base substitution. This allows the introduction of random mutations at any position in the molecule. Another method is available which is useful in introducing defined or random mutations (Joyce and Inoue, *Nucleic Acids Research* 17: 711–722 (1989)). The modified PCR method of Cadwell and Joyce is, nevertheless, particularly preferred for use as described herein.

Enzymatic nucleic acid molecules of the present invention include those with altered recognition sites. In various embodiments, these altered recognition sites confer unique sequence specificities on the enzymatic nucleic acid molecule including such recognition sites.

The exact bases present in the recognition site are important in determining the base sequence or amino acid residue sequence that is recognized by the enzymatic RNA molecule, as well as the site at which cleavage will take place. It should be appreciated, however, that other sequences and sites in the enzymatic RNA molecules of the present invention may participate in the recognition-and-cleavage process. Amino acid residue sequences and conformations of the substrate molecules may also affect this process.

Cleavage of the substrate preferably occurs immediately 3' of the substrate cleavage sequence, the substrate oligomer sequence that associates with the recognition site. For example, if the substrate is an oligonucleotide, this cleavage leaves a 3' hydroxyl group on the substrate cleavage sequence and a 5' phosphate on the nucleotide that was originally immediately 3' of the substrate cleavage sequence in the original substrate. If, on the other hand, the substrate is (or includes) an amino acid residue sequence, cleavage leaves a 3' amino group on the substrate cleavage sequence and a 5' carboxyl group on the amino acid that was originally immediately 3' of the substrate cleavage sequence in the original substrate. Cleavage can be redirected to a site of choice by changing the bases present in the recognition sequence/internal guide sequence (see Murphy et al., *PNAS USA* 86: 9218–9222 (1989)) and/or in other sites and sequences of the enzymatic RNA molecule.

The recognition site may also be provided as a separate nucleic acid, an external recognition site not covalently coupled to the rest of the enzymatic RNA molecule. External recognition sites may direct cleavage at a specific amino acid or base sequence (see, e.g., Doudna et al., *Nature* 339: 519–522 (1989)). If an external recognition site is used, the enzymatic RNA molecule used with it would probably not contain a recognition site but would tend to comprise a P3[5'] region, a second spacer region, a first stem loop, a second stem loop, a third spacer region and a third stem loop where the third stem loop comprises a 5' stem portion defining a P3[3'] region capable of hybridizing to said P3[5'] region.

Use of an enzymatic RNA molecule of the present invention with an external recognition site allows the target sequence to be altered by merely changing the external recognition site sequence. Use of a plurality of different external recognition sequences with an enzymatic RNA molecule of the present invention allows the substrate to be cleaved at each of the different residue sequences encoded by the external recognition sequences.

First spacer regions typically contain a sequence of nucleotides of about 3 to 7, preferably about 5, bases in length. In one variation, the nucleotides making up the first spacer have the sequence 5'-NNNNA-3' (SEQ ID NO 2), where N represents the presence of any nucleotide at that position. In another variation, the first spacer region is defined by the sequence 5'-AACAA-3' (SEQ ID NO 3).

In other embodiments, the first spacer region is comprised of a nucleotide sequence defining two spacer stem loops. In one variation, the first spacer stem loop is 25 nucleotides in length, and the second spacer stem loop is 36 bases in length. In another variation, the first spacer stem loop has the base sequence 5'-AGUUACCAGGCAUGCACCUG-GUAGUCA-3' (SEQ ID NO 4), and the second spacer stem loop has the base sequence 5'-GUCUUUAAACCAAUA-GAUUGGAUCGGUUUAAAAGGC-3' (SEQ ID NO 5).

As noted previously, the foregoing descriptions of loop and spacer regions are exemplary and are not to be construed as limiting the disclosed invention(s).

A stem loop is a secondary structure formed by a nucleotide sequence that has "folded over on itself". A stem loop comprises a 5' nucleotide sequence portion, designated a 5' paring segment (P[5']) that is capable of hybridizing to a nucleotide sequence located 3' of the P[5'] and is designated the 3' pairing segment (P[3']). In a stem loop, the P[5'] and P[3'] are connected by a nucleotide sequence called a loop. The P[5'] and P[3'] hybridize and form a nucleic acid duplex. The nucleic acid duplex formed by the P[5'] and P[3'] does not have to be a perfect duplex and may contain stretches of nucleotides that are either unpaired or paired to a sequence outside the stem loop.

In various alternative embodiments, an enzymatic RNA molecule of the present invention has an enhanced or optimized ability to cleave amino acid substrates.

As those of skill in the art will appreciate, the rate of an enzyme-catalyzed reaction varies depending upon the substrate and enzyme concentrations and, in general, levels off at high substrate or enzyme concentrations. Taking such effects into account, the kinetics of an enzyme-catalyzed reaction may be described in the following terms, which define the reaction.

The enhanced or optimized ability of an enzymatic RNA molecule of the present invention to cleave a dipeptide or polypeptide substrate may be determined in a cleavage reaction with varying amounts of labeled peptide substrate in the presence of enzymatic RNA molecule as described in Examples 1 and 2. The ability to cleave the substrate is generally defined by the catalytic rate ($k_{cat}$) divided by the Michaelis constant ($K_M$). The symbol $k_{cat}$ represents the maximal velocity of an enzyme reaction when the substrate approaches a saturation value. $K_M$ represents the substrate concentration at which the reaction rate is one-half maximal. Values for $K_M$ and $k_{cat}$ are determined in this invention by experiments in which the substrate concentration [S] is in excess over enzymatic RNA molecule concentration [E]. Initial rates of reaction ($v_o$) over a range of substrate concentrations were estimated from the initial linear phase, generally the first 5% or less of the reaction. Typically eight data points ware fit by a least squares method to a theoretical line given by the equation: $v=-K_M(v_o/[S])+V_{max}$. Thus, $k_{cat}$ and $K_M$ are determined by the initial rate of reaction, $v_o$, and the substrate concentration [S].

In one embodiment of the present invention, an enzymatic RNA molecule of the present invention exhibits amide bond-cleaving activity not normally found in wild type ribozymes. In various alternative embodiments, an enzymatic RNA molecule of the present invention has an enhanced or optimized ability to cleave amino acid substrates, preferably dipeptide or polypeptide substrates. One skilled in the art will appreciate that the enhanced or optimized ability of an enzymatic RNA molecule to cleave amino acid substrates may vary depending upon the selection constraints applied during the in vitro evolution procedure of the invention.

Enzymatic RNA molecules of the present invention may also be characterized as displaying a $K_M$ value that is improved over the wild type. As noted above, $K_M$ represents the substrate concentration at which the reaction rate is one-half maximal; thus, an improved $K_M$ indicates an improvement in substrate processing. In various embodiments, enzymatic RNA molecules of the present invention have a $K_M$ that is statistically significant when compared with the $K_M$ of wild type ribozymes, the latter of which are apparently unable to cleave amino acid substrates.

One skilled in the art will understand that the enhanced or optimized ability of an enzymatic RNA molecule to process amino acid (e.g. polypeptide) substrates may vary depending upon the selection constraints applied during the in vitro evolution procedure of the invention and may include a reduction of the peptide concentration to favor enzymatic RNA molecules with improved substrate processing ability.

In other embodiments, an enzymatic RNA molecule of the present invention has an enhanced or optimized ability to bind an amino acid substrate. The ability of an enzymatic RNA molecule to bind a polypeptide substrate is defined by the dissociation constant ($K_D$). The $K_D$ is an equilibrium constant describing the dissociation of the enzymatic RNA molecule:substrate complex into its individual components. The $K_D$ constant as understood in the context of this invention is determined by a gel shift analysis to determine the percent enzymatic RNA molecule bound to the amino acid product, as described in the Examples. A binding curve is generated by plotting the percent of product bound to enzymatic RNA molecule over a range of enzymatic RNA molecule concentration. The $K_D$ is determined by fitting the data to a theoretical binding curve using the least squares method. Typically, the enzymatic RNA molecule concentration [E] vastly exceeds the product; therefore, the theoretical binding curve can be represented by the equation: % bound= $[E]/([E]+K_D)$, where $K_D=[E]$ when half of the total product is bound to the enzymatic RNA molecule.

An enzymatic RNA molecule of the present invention preferably binds amino acid substrate with a $K_D$ which is an improvement over wild type ribozymes. For example, an enzymatic RNA molecule of the present invention preferably binds peptides with a $K_D$ having a value less than 30 µM. In preferred embodiments, enzymatic RNA molecules bind polypeptide with a $K_D$ having a value less than about 10 µM. In more preferred embodiments, the $K_D$ of an amino acid-binding enzymatic RNA molecule is less than about 1 µM. In an even more preferred embodiment, the $K_D$ of an amino acid-binding enzymatic RNA molecule is less than about 50 nM, more preferably less than about 25 nM, and even more preferably less than about 10 nM. Especially preferred enzymatic RNA molecules bind peptide substrate with a $K_D$ of 5 nM or less, e.g., with a $K_D$ of about 0.1–5 nM.

One skilled in the art will understand that the enhanced or optimized ability of an enzymatic RNA molecule to bind amino acid-containing substrates may vary depending upon the selection constraints applied during the in vitro evolution procedure of the invention and may include a reduction of the amino acid concentration to favor enzymatic RNA molecules with improved substrate binding affinity.

In another variation, an enzymatic RNA molecule of the present invention has an enhanced or optimized substrate turnover rate. The enhanced or optimized substrate turnover rate may be determined in single-turnover kinetic experiments with the enzymatic RNA molecule in excess of the substrate as described in the following Examples. Initial rates ($k_{obs}$) are obtained using no more than the first 5% of the reaction. Given that $k_{cat}/K_M=k_{obs}/[E]$, each $k_{obs}$ value, obtained at different enzymatic RNA molecule concentrations, provides an estimate of $k_{cat}/K_M$. Generally, eight or more measurements of $k_{cat}/K_M$ are obtained. The value of $k_{cat}$ in the presence of limited substrate indicates the substrate turnover number rate and is expressed in the number of catalytic cycles that are completed by the enzyme per unit of time under the assay conditions. One skilled in the art will appreciate that the enhanced or optimized substrate turnover rate of an enzymatic RNA molecule of the present invention may vary depending upon the selection constraints applied during the in vitro evolution procedure of the invention and may include a reduction of the reaction time to favor enzymatic RNA molecules with improved substrate turnover rates.

In other embodiments, an enzymatic RNA molecule of the present invention is capable of functioning efficiently over a wide range of temperatures. In yet another variation, an enzymatic RNA molecule of the present invention is capable of functioning efficiently over a wide range of pH.

In various alternative embodiments, an enzymatic RNA molecule of the present invention is capable of functioning efficiently in the presence or absence of $Mg^{2+}$. Alternatively, an enzymatic RNA molecule of the present invention is capable of functioning efficiently in the presence or absence of divalent cations other than $Mg^{2+}$. Other suitable divalent cations may be selected from the group comprised of $Mn^{2+}$, $Zn^{2+}$, or $Ca^{2+}$. It is anticipated that cation concentrations similar to those described above for $Mg^{2+}$ will be useful as disclosed herein.

Optionally, monovalent cations may also be present as "alternatives" for the use of divalent cations. For example, monovalent cations such as sodium ($Na^+$) or potassium ($K^+$) may be present, either as dissociated ions or in the form of dissociable compounds such as NaCl or KCl. In one embodiment, a monovalent cation is present in a concentration ranging from about 0–200 mM. In other embodiments, monovalent cations are present in a concentration ranging from about 2–100 mM. Alternatively, the concentration of monovalent cations ranges from about 2 mM–50 mM. In other embodiments, the concentration ranges from about 2 mM–25 mM, with a concentration of about 2 mM–15 mM being preferred.

In various embodiments, an enzymatic RNA molecule of the present invention optionally includes a 3' hydroxyl of G (i.e. guanosine, or one of its 5'-phosphorylated forms), which functions as a nucleophile—i.e., it "attacks" substrate molecules, particularly hybrid substrates, at a phosphodiester or amide bond. For example, in the L-21 ribozyme derived from the group I intron of *Tetrahymena thermophila*, the G264-C311 base pair—which is known as the "G-site"—binds the G substrate. (See, e.g., Wang and Cech, *Science* 256: 526–529 (1992).)

Alternatively, in other embodiments, wherein an enzymatic RNA molecule of the present invention lacks a 3' terminal $G_{OH}$, the $G_{OH}$ may be supplied as a free (i.e., unattached) attacking group. In such embodiments, an enzymatic RNA molecule is able to "attack" multiple substrates in sequential fashion. In either case, the term "enzymatic RNA molecules" as used in the present disclosure includes enzymatic RNA molecule including, as well as those lacking, a 3' $G_{OH}$.

In various embodiments, an enzymatic RNA molecule of the present invention may combine one or more modifications or mutations including additions, deletions, and substitutions. In alternative embodiments, such mutations or modifications may be generated using methods which produce random or specific mutations or modifications. These mutations may change the length of, or alter the nucleotide sequence of, a stem loop, the P3[5'], the P3[3'] region, a spacer region or the recognition sequence. One or more mutations within one catalytically active enzymatic RNA molecule may be combined with the mutation(s) within a second catalytically active enzymatic RNA molecule to produce a new enzymatic RNA molecule containing the mutations of both molecules.

In other preferred embodiments, an enzymatic RNA molecule of the present invention may have random mutations introduced into it using a variety of methods well known to those skilled in the art. For example, the method described by Cadwell and Joyce (*PCR Methods and Applications* 2: 28–33 (1992)) is particularly preferred for use as disclosed herein, as it efficiently introduces random mutations into populations of enzymatic RNA molecules. (Also see Cadwell and Joyce, *PCR Methods and Applications* 3 (Suppl.): S136–S140 (1994).) According to this modified PCR method, random point mutations may be introduced into cloned genes. The method has been used to mutagenize the gene encoding the ribozyme with a mutation rate of 0.66% ±0.13% (95% confidence interval) per position per PCR, as determined by sequence analysis, with no strong preferences observed with respect to the type of base substitution. This allows the introduction of random mutations at any position in the molecule.

Another method is available which is useful in introducing defined or random mutations (see Joyce and Inoue, *Nucleic Acids Research* 17: 711–722 (1989)). This latter method involves excision of a template (coding) strand of a double-stranded DNA, reconstruction of the template strand with inclusion of mutagenic oligonucleotides, and subsequent transcription of the partially-mismatched template. This allows the introduction of defined or random mutations at any position in the molecule by including polynucleotides containing known or random nucleotide sequences at selected positions.

Enzymatic RNA molecules of the present invention may be of varying lengths and folding patterns, as appropriate, depending on the type and function of the molecule. For example, enzymatic RNA molecules derived from group I introns (e.g., Tetrahymena-derived ribozymes) may be about 413 or more nucleotides in length, although a length not exceeding 413 nucleotides is preferred, to avoid limiting the therapeutic usefulness of molecules by making them too large or unwieldy. In various therapeutic applications, enzymatic RNA molecules of the present invention comprise the enzymatically active portions of ribozymes. In various embodiments, enzymatic RNA molecules of the present invention comprise fewer than 400 nucleotides, fewer than 300 nucleotides, fewer than 200 nucleotides, or fewer than 100 nucleotides.

In other therapeutic applications, enzymatic RNA molecules such as "hammerhead" ribozymes are preferably no more than about 50 nucleotides in length, with a length of 30–40 nucleotides being particularly preferred. Even more preferred are hammerhead ribozymes of about 31–36 nucleotides in length.

Moreover, if one intends to synthesize molecules for use as disclosed herein, the larger the enzymatic nucleic acid molecule is, the more difficult it is to synthesize. Those of skill in the art will certainly appreciate these design constraints.

Various preferred methods of modifying ribozymes and other enzymatic RNA molecules, ribonucleases, deoxyribonucleases, and amidases of the present invention are further described in Examples 1–3 hereinbelow.

C. Nucleotide Analogs

As noted above, the term "nucleotide analog" as used herein generally refers to a purine or pyrimidine nucleotide that differs structurally from A, T, G, C, or U, but is sufficiently similar to substitute for the normal nucleotide in a nucleic acid molecule. As used herein, the term "nucleotide analog" encompasses altered bases, different sugars, or a combination of the two. Examples of nucleotide analogs useful according to the present invention include those listed in the following Table, most of which are found in the approved listing of modified bases at 37 CFR §1.822 (which is incorporated herein by reference)

TABLE 1

| Abbreviation | Nucleotide Analogs Description |
|---|---|
| ac4c | 4-acetylcytidine |
| chm5u | 5-(carboxyhydroxylmethyl)uridine |
| cm | 2'-O-methylcytidine |
| cmnm5s2u | 5-carboxymethylaminomethyl-2-thioridine |
| d | dihydrouridine |
| fm | 2'-O-methylpseudouridine |
| galq | β, D-galactosylqueosine |
| gm | 2'-O-methylguanosine |
| i | inosine |
| i6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| manq | β, D-mannosylmethyluridine |
| mcm5s2u | 5-methoxycarbonylmethyluridine |
| mo5u | 5-methoxyuridine |
| ms2i6a | 2-methylthio-N6-isopentenyladenosine |
| ms2t6a | N-((9-β-D-ribofuranosyl-2-methylthiopurine-6-yl)carbamoyl)threonine |
| mt6a | N-((9-β-D-ribofuranosylpurine-6-yl)N-methyl-carbamoyl)threonine |
| mv | uridine-5-oxyacetic acid methylester |
| o5u | uridine-5-oxyacetic acid (v) |
| osyw | wybutoxosine |
| p | pseudouridine |
| q | queosine |
| s2c | 2-thiocytidine |

TABLE 1-continued

Nucleotide Analogs

| Abbreviation | Description |
| --- | --- |
| s2t | 5-methyl-2-thiouridine |
| s2u | 2-thiouridine |
| s4u | 4-thiouridine |
| t | 5-methyluridine |
| t6a | N-((9-β-D-ribofuranosylpurine-6-yl)carbamoyl)threonine |
| tm | 2'-O-methyl-5-methyluridine |
| um | 2'-O-methyluridine |
| yw | wybutosine |
| x | 3-(3-amino-3-carboxypropyl)uridine, (acp3)u |
| araU | β, D-arabinosyl |
| araT | β, D-arabinosyl |

Other useful analogs include those described in published international application no. WO 92/20823, or analogs made according to the methods disclosed therein. Analogs described in DeMesmaeker, et al., *Angew. Chem. Int. Ed. Engl.* 33: 226–229 (1994); DeMesmaeker, et al., *Synlett:* 733–736 (October. 1993); Nielsen, et al., *Science* 254: 1497–1500 (1991); and Idziak, et al., *Tetrahedron Letters* 34: 5417–5420 (1993) are also useful according to the within-disclosed invention and said disclosures are incorporated by reference herein.

D. Methods of Engineering Enzymatic RNA Molecules

The present invention also contemplates methods of producing nucleic acid molecules having a predetermined activity. In one preferred embodiment, the nucleic acid molecule is an enzymatic RNA molecule. In another variation, the desired activity is a catalytic activity.

In one embodiment, the present invention contemplates methods of synthesizing enzymatic RNA molecules which may then be "engineered" to catalyze a specific or predetermined reaction. Methods of preparing enzymatic RNA molecules are described herein; see, e.g., the Examples hereinbelow. In other embodiments, an enzymatic RNA molecule of the present invention may be engineered to bind small molecules or ligands, such as adenosine triphosphate (ATP). (See, e.g., Sassanfar, et al., *Nature* 364: 550–553 (1993).)

In another embodiment, the present invention contemplates that a population of enzymatic RNA molecules may be subjected to mutagenizing conditions to produce a diverse population of mutant enzymatic RNA molecules or ribozymes. Thereafter, enzymatic RNA molecules having desired characteristics are selected and/or separated from the population and are subsequently amplified.

Alternatively, mutations may be introduced in the enzymatic RNA molecule by altering the length of the recognition site (internal guide sequence) of the enzymatic RNA molecule. The recognition site of the enzymatic RNA molecule associates with a complementary sequence of bases within a substrate nucleic acid or substrate hybrid oligonucleotide-oligopeptide sequence. Methods of altering the length of the recognition site are known in the art and include PCR, for example; useful techniques are described further in the Examples below.

Alteration of the length of the recognition site of the enzymatic RNA molecule which retains the ability to recognize a sequence of bases within the nucleic acid segment of a hybrid substrate molecule or with an amino acid residue sequence recognized thereby may have a desirable effect on the binding specificity of the enzymatic RNA molecule. For example, an increase in the length of the recognition site may increase binding specificity between the enzymatic RNA molecule and the complementary base sequences of an oligonucleotide in a hybrid substrate, or may enhance recognition of amino acid residue sequences in a hybrid molecule or in a polypeptide substrate. In addition, an increase in the length of the recognition site may also increase the affinity with which it binds to substrate. In various embodiments, these altered recognition sites in the enzymatic RNA molecule confer increased binding specificity and affinity between the enzymatic RNA molecule and its substrate.

It has recently been noted that certain oligonucleotides are able to recognize and bind molecules other than oligonucleotides with complementary sequences. These oligonucleotides are often given the name "aptamers". For example, Ellington and Szostak describe RNA molecules that are able to bind a variety of organic dyes (*Nature* 346: 818–822 (1990)), while Bock, et al. describe ssDNA molecules that bind human thrombin (*Nature* 355: 564–566 (1992)). Similarly, Jellinek, et al. describe RNA ligands to basic fibroblast growth factor (*PNAS USA* 90: 11227–11231 (1993)).

Until the advent of the present invention, however, no one has described the existence of catalytically active RNA enzymes with reproducible amide-cleaving capabilities. The art has also been silent with respect to methods of engineering and selecting catalytically active oligonucleotide molecules possessing this ability, until now.

One of skill in the art may realize that the enzymatic RNA molecules of this invention can be altered at any nucleotide sequence, such as the recognition site, by various methods disclosed herein, including PCR and 3SR. Additional nucleotides can be added to the 5' end of the enzymatic RNA molecule by including the additional nucleotides in the primer used to introduce the T7 promoter binding site. The additional nucleotides would be included in the primer between the T7 promoter sequence and the nucleotide sequences which hybridize to the enzymatic RNA molecule at the 5' end.

Enzymatic RNA molecules of the present invention may also be prepared or engineered in a more non-random fashion via use of methods such as site-directed mutagenesis. For example, site-directed mutagenesis may be carried out essentially as described in Morinaga, et al., *Biotechnology* 2: 636 (1984), which is incorporated herein by reference. A useful site-directed mutagenesis technique is also described in Example 1 below.

In various embodiments, the population of group I nucleic acids is made up of at least 2 group I nucleic acids. In one variation, group I nucleic acids are nucleic acid molecules having a nucleic acid sequence defining a recognition site that is contiguous or adjacent to the 5'-terminus of the nucleotide sequence, a first spacer region located 3'-terminal to the recognition site, a P3[5'] region located 3'-terminal to the first spacer region, a second spacer region located 3'-terminal to the P3[5'] region, a first stem loop located 3'-terminal to the second spacer region, a second stem loop located 3'-terminal to the first stem loop, a third spacer region located 3'-terminal to the second stem loop, and a third stem loop located 3'-terminal to the third spacer region, the third stem loop comprising a 5' stem portion defining a P3[3'] region capable of hybridizing to the P3[5'] region. Other characteristics of enzymatic RNA molecules produced according to the presently-disclosed methods are described elsewhere herein.

In other embodiments, mutagenizing conditions include conditions that introduce either defined or random nucleotide substitutions within an enzymatic RNA molecule. Examples of typical mutagenizing conditions include conditions disclosed in other parts of this specification and the methods described by Joyce et al., *Nucl. Acids Res.* 17: 711–722 (1989); Joyce, *Gene* 82: 83–87 (1989); and Beaudry and Joyce, *Science* 257: 635–41 (1992).

In still other embodiments, a diverse population of mutant enzymatic nucleic acid molecules of the present invention is one that contains at least 2 nucleic acid molecules that do not have the exact same nucleotide sequence. In other variations, from such a diverse population, an enzymatic RNA molecule or other enzymatic nucleic acid having a predetermined activity is then selected on the basis of its ability to perform the predetermined activity. In various embodiments, the predetermined activity comprises, without limitation, enhance catalytic activity, decreased $K_M$, enhanced substrate binding ability, altered substrate specificity, and the like.

Parameters which may be considered aspects of enzyme performance include catalytic activity or capacity, substrate binding ability, enzyme turnover rate, enzyme sensitivity to feedback mechanisms, and the like. In certain aspects, substrate specificity may be considered an aspect of enzyme performance, particularly in situations in which an enzyme is able to recognize and bind two or more competing substrates, each of which affects the enzymes' performance with respect to the other substrate(s).

Substrate specificity, as used herein, may refer to the specificity of an enzymatic nucleic acid molecule as described herein for a particular substrate, such as one comprising oligonucleotides only, polypeptides only, or a composite of both. In the case of the latter type of substrate, an enzymatic nucleic acid molecule of the present invention may preferentially bind to a particular region of such a hybrid or composite substrate.

Substrate specificity may also include sequence specificity; i.e., an enzymatic nucleic acid molecule of the present invention may "recognize" and bind to a nucleic acid substrate having a particular nucleic acid sequence, or to a substrate having a particular amino acid residue sequence. For example, if the substrate recognition site of an enzymatic nucleic acid molecule of the present invention will only bind to substrate molecules having a series of one or two arginine residues in a row, then the enzymatic nucleic acid molecule will tend not to recognize or bind nucleic acid substrate molecules lacking such a sequence. In various embodiments, selecting includes any means of physically separating the mutant enzymatic nucleic acids having a predetermined activity from the diverse population of mutant enzymatic nucleic acids. Often, selecting comprises separation by size, by the presence of a catalytic activity, or by hybridizing the mutant nucleic acid to another nucleic acid or to a peptide that is either in solution or attached to a solid matrix.

In various embodiments, the predetermined activity is such that the mutant enzymatic nucleic acid having the predetermined activity becomes labelled in some fashion by virtue of the activity. For example, the predetermined activity may be an enzymatic RNA molecule activity whereby the activity of the mutant enzymatic nucleic acid upon its substrate causes the mutant enzymatic nucleic acid to become covalently linked to it. The mutant enzymatic nucleic acid is then selected by virtue of the covalent linkage.

In other embodiments, selecting a mutant enzymatic nucleic acid having a predetermined activity includes amplification of the mutant enzymatic nucleic acid (see, e.g., Joyce, *Gene* 82: 83–87 (1989); Beaudry and Joyce, *Science* 257: 635–41 (1992)).

E. Compositions

The invention also contemplates compositions containing one or more types or populations of enzymatic RNA molecules of the present invention; e.g., different types or populations may recognize and cleave different amino acid residue sequences. Compositions may further include a peptide-containing substrate. Compositions according to the present invention may further comprise magnesium ion or other divalent or monovalent cations, as discussed in section B above.

Preferably, the enzymatic RNA molecule is present at a concentration of about 0.05 µM to about 2 µM. Typically, the enzymatic RNA molecule is present at a concentration ratio of enzymatic RNA molecule to substrate of from about 1:5 to about 1:50. More preferably, the enzymatic RNA molecule is present in the composition at a concentration of about 0.1 µM to about 1 µM. Even more preferably, compositions contain the enzymatic RNA molecule at a concentration of about 0.1 µM to about 0.5 µM. Preferably, the substrate is present in the composition at a concentration of about 0.5 µM to about 1000 µM. One skilled in the art will understand that there are many sources of amide bond-containing substrates including naturally-occurring and synthetic amino acids, polypeptides, and proteins (including those in denatured form), and molecules containing same.

Magnesium ion (or another suitable monovalent or divalent cation, as described previously) may also be present in the composition, at a concentration of about 2–100 mM. More preferably, the magnesium ion is present in the composition at a concentration of about 2 mM to about 50 mM. Preferably, magnesium ion is present at a concentration of about 5 mM to about 15 mM, with a concentration of about 10 mM being particularly preferred. One skilled in the art will understand that the magnesium ion concentration is only constrained by the limits of solubility of magnesium in aqueous solution and a desire to have the enzymatic RNA molecule present in the same composition in an active conformation.

The invention also contemplates compositions containing an enzymatic RNA molecule of the present invention, hybrid oligonucleotide-oligopeptide molecules, and magnesium ion in concentrations as described hereinabove. As noted previously, other monovalent or divalent ions (e.g., $Mn^{2+}$) may be used in place of magnesium.

Also contemplated by the present invention are compositions containing an enzymatic RNA molecule of the present invention, amino acid-containing substrate, and magnesium ion at a concentration of greater than about 2 millimolar, wherein said substrate is greater in length than the recognition site present on the enzymatic RNA molecule.

F. Methods of Using Enzymatic RNA Molecules

The methods of using enzymatic RNA molecules as disclosed herein are legion. As discussed previously, molecules capable of cleaving the bonds linking neighboring amino acid molecules (e.g., peptide bonds) have numerous uses encompassing a wide variety of applications. For example, enzymatic RNA molecules having the within-disclosed capabilities, structures, and/or functions are useful in pharmaceutical and medical products (e.g., for wound debridement, clot dissolution, etc.), as well as in household items (e.g., detergents, dental hygiene products, meat tenderizers). Industrial utility of the within-disclosed compounds, compositions and methods is also contemplated and well within the scope of the present invention.

G. Vectors

The present invention also features expression vectors including a nucleic acid segment encoding an enzymatic RNA molecule of the present invention situated within the vector, preferably in a manner which allows expression of that enzymatic RNA molecule within a target cell (e.g., a plant or animal cell).

Thus, in general, a vector according to the present invention includes a bacterial, viral or eukaryotic promoter within a plasmid, cosmid, phagemid, virus, viroid, or phage vector. Other suitable vectors include double-stranded DNA (dsDNA), partially double-stranded DNA, dsRNA, partially dsRNA, or single-stranded RNA (ssRNA) or DNA (ssDNA). It should also be appreciated that useful vectors according to the present invention need not be circular.

In one aspect of the present invention, a first enzymatic RNA molecule-encoding nucleotide sequence is transcriptionally linked to a promoter sequence. In another variation, one or more additional enzymatic RNA molecule-encoding nucleotide sequences are also included in the vector; said additional enzymatic RNA molecule-encoding sequences may be located on either side, or both sides, of a nucleotide sequence encoding the first enzymatic RNA molecule. Preferably, there are intervening nucleotides or nucleotide sequences between successive enzymatic RNA molecule-encoding sequences.

In another variation, nucleotide sequences flanking each of the additional enzymatic RNA molecule-encoding sequences are preferably provided, which sequences may be recognized by the first enzymatic RNA molecule. The intervening or flanking sequences preferably comprise at least 1 nucleotide; more preferably, intervening or flanking sequences are about 2–20 nucleotides in length, with sequences of about 5–10 nucleotides in length being particularly preferred.

The addition of polyadenine (poly(A)) tails may also be useful to protect the 3' end of an enzymatic RNA molecule according to the present invention. These may be provided by including a poly(A) signal site in the expression vector, which would signal a cell to add the poly(A) tail in vivo. Preferably, the signal is aligned in such a fashion that it prevents unwanted secondary structure formation with other parts of the enzymatic RNA molecule.

Alternatively, a poly(A) tail may be provided by introducing a poly(A) sequence directly into the expression vector. Since the poly(A) sequence may decrease in size over time when expressed in vivo, the vector may need to be monitored over time. Care must be taken, however, in the addition of a poly(A) tail which binds poly(A) binding proteins, which may prevent the enzymatic RNA molecule from acting upon its target nucleotide sequence. Other vectors and methods of generating same are described in the art; see, e.g., published international application no. WO 93/23569.

Thus, in one example, a vector may comprise a promoter operatively linked for expression to a nucleotide sequence encoding a first enzymatic RNA molecule followed, in a 3'→5' direction, by: (1) a "flanking" nucleotide sequence capable of being recognized and cleaved by said first enzymatic RNA molecule; (2) a nucleotide sequence encoding a second enzymatic RNA molecule; (3) another flanking nucleotide sequence capable of being recognized and cleaved by said first enzymatic RNA molecule; (4) a nucleotide sequence encoding a third enzymatic RNA molecule; (4) yet another flanking nucleotide sequence capable of being recognized and cleaved by said first enzymatic RNA molecule; and so forth.

Preferably, a vector according to the present invention includes a plurality of nucleic acid sequences encoding the second enzymatic RNA molecule, each flanked by nucleic acid sequences recognized by the first enzymatic RNA molecule. More preferably, such a plurality includes at least 5, preferably 7, more preferably 9 or more, nucleic acid sequences. In other embodiments, a vector as disclosed herein includes a promoter which regulates expression of the nucleic acid encoding the enzymatic RNA molecules from the vector.

The invention also contemplates that a promoter sequence is linked to a first or "releasing" enzymatic RNA molecule having an appropriate restriction endonuclease site. A single-stranded oligonucleotide is then provided which encodes the two flanking regions and a second (i.e., "therapeutic") enzymatic RNA molecule. The oligonucleotides are then allowed to form partial duplexes via hybridization at the flanking regions. The single-stranded sections are then filled in using a DNA polymerase and deoxyribonucleotide triphosphates (dNTPs) to form a dsDNA molecule, which may then be ligated to the restriction endonuclease site to form the desired vector. As noted above, the vector may be chosen from the group comprising plasmids, cosmids, phagemids, virus, viroids, or phage.

Preferably, the plurality of nucleic acid sequences are identical and are arranged in sequential fashion such that each has an identical end nearest to the promoter. If desired, a poly(A) sequence adjacent to the sequence encoding the first or second enzymatic RNA molecule may be provided to increase stability of the RNA produced by the vector and/or to enhance transport to appropriate cellular compartments. Further, a restriction endonuclease site adjacent to the nucleic acid encoding the first enzymatic RNA molecule may be provided to allow insertion of nucleic acid encoding the second enzymatic RNA molecule during construction of the vector.

If delivery of a vector construct to a eucaryotic cell is desired, cellular splicing mechanisms within the target cell(s) may be utilized or integrated to cleave out the therapeutic second enzymatic RNA molecule(s) by encoding recognition sequences for the second enzymatic RNA molecules within the flanking sequences of the expressed transcript. Multiple copies of the releasing first enzymatic RNA molecule may be provided to enhance release of the second (i.e. therapeutic) enzymatic RNA molecule if the turnover rate is slower than the degradation rate of the second enzymatic RNA molecule. If the target cell is a bacterial cell, in vitro modifications and certain cell modifications may be enhanced by providing appropriate nucleotide sequences within the vector and are useful in the enhancement of the turnover rate, enzymatic stability, and cleavage activity of the within-disclosed enzymatic RNA molecules.

A method of forming an enzymatic RNA molecule expression vector includes providing a vector comprising nucleic acid encoding a first enzymatic RNA molecule, as discussed above, and providing a single-stranded DNA molecule encoding a second enzymatic RNA molecule, also as discussed above. The single-stranded DNA is then allowed to anneal to form a partial duplex DNA which can be filled in by treatment with an appropriate enzyme, such as a DNA polymerase in the presence of dNTPs, to form a duplex DNA which can then be ligated to the vector. Large vectors resulting from use of this method can then be selected to insure that a high copy number of the single-stranded DNA encoding the second enzymatic RNA molecule is incorporated into the vector.

A method for producing enzymatic RNA molecules thus involves providing a vector as described above, expressing RNA from that vector, and allowing cleavage by the first enzymatic RNA molecule to release the second (and any subsequent) enzymatic RNA molecule. Suitable restriction endonuclease sites may also be provided to ease the construction of such a vector in DNA vectors or in requisite DNA vectors of an RNA expression system.

The second (and any additional) enzymatic RNA molecule may be any desired type of enzymatic RNA molecule, such as a ribozyme, including group I and group II introns, hammerhead, hairpin, and other types of ribozymes or enzymatically active portions thereof.

The first enzymatic RNA molecule is selected to cleave the encoded cleavage (e.g., "flanking") sequence, and may also be any desired ribozyme—e.g., a ribozyme derived from Tetrahymena—which may, for example, include an embedded restriction endonuclease site in the center of a self-recognition sequence to aid in vector construction. This endonuclease site is useful for construction of, and subsequent analysis of, a vector as described herein.

A vector according to the present invention is preferably operably linked for expression to an appropriate promoter. For example, a vector according to the present invention may comprise an enzymatic RNA molecule under the control of a viral promoter, such as an Epstein-Barr Virus (EBV) promoter. A variety of viral promoters useful for this purpose are known in the art; see, e.g., those described in published PCT application no. WO 93/23569.

In another variation, a vector according to the present invention includes two or more enzymatic RNA molecules. In one embodiment, a first enzymatic RNA molecule has intramolecular cleaving activity and is able to recognize and cleave nucleotide sequences to release other enzymatic RNA sequences; i.e., it is able to function to "release" other enzymatic RNA molecules from the vector. For example, a vector is preferably constructed so that when the first enzymatic RNA molecule is expressed, that first molecule is able to cleave nucleotide sequences flanking additional nucleotide sequences encoding a second enzymatic RNA molecule, a third enzymatic RNA molecule, and so forth. Presuming said first enzymatic RNA molecule (i.e., the "releasing" molecule) is able to cleave oligonucleotide sequences intramolecularly, the additional (e.g. second, third, and so on) enzymatic RNA molecules (i.e., the "released" molecules) need not possess characteristics identical to the "releasing" molecule. Indeed, in various preferred embodiments, the "released" (i.e. second, third, etc.) enzymatic RNA molecule has amide bond-cleaving activity, while the first ("releasing") enzymatic RNA molecule has nuclease activity.

Alternatively, the first enzymatic RNA molecule may be encoded on a separate vector from the second enzymatic RNA molecule(s) and may have intermolecular cleaving activity. As noted herein, the first enzymatic RNA molecule can be a self-cleaving enzymatic RNA molecule (e.g., a ribozyme), and the second enzymatic RNA molecule may be any desired type of enzymatic RNA molecule (e.g., a ribozyme). When a vector is caused to express RNA from these nucleic acid sequences, that RNA has the ability under appropriate conditions to cleave each of the flanking regions, thereby releasing one or more copies of the second enzymatic RNA molecule. If desired, several different second enzymatic RNA molecules can be placed in the same cell or carrier to produce different ribozymes.

Methods of isolating and purifying enzymatic RNA molecules of the present invention are also contemplated. In addition to the methods described herein, various purification methods (e.g. those using HPLC) and chromatographic isolation techniques are available in the art. See, e.g., the methods described in published international application no. WO 93/23569, the disclosures of which are incorporated herein by reference.

It should also be understood that various combinations of the embodiments described herein are included within the scope of the present invention. Other features and advantages of the present invention will be apparent from the descriptions hereinabove, from the Examples to follow, and from the claims.

EXAMPLES

The following examples illustrate, but do not limit, the present invention.

Example 1

In Vitro Evolution of Enzymatic RNA Molecules

A. General Principles

In vitro selection and in vitro evolution techniques allow new catalysts to be isolated without a priori knowledge of their composition or structure. Such methods have been used to obtain RNA enzymes with novel catalytic properties. Ribozymes that undergo autolytic cleavage with lead cation have been derived from a randomized pool of $tRNA^{Phe}$ molecules (Pan and Uhlenbeck, Biochemistry 31: 3887–3895 (1992)). Group I ribozyme variants have been isolated that can cleave DNA (Beaudry and Joyce, Science 257: 635–641 (1992)) or that have altered metal dependence (Lehman and Joyce, Nature 361: 182–185 (1993)). Starting with a pool of random RNA sequences, molecules have been obtained that catalyze a polymerase-like reaction (Bartel and Szostak, Science 261: 1411–1418 (1993)). In the present example, refinement of specific catalytic properties of an evolved enzyme via alteration of the selection constraints during an in vitro evolution procedure is described.

A method of in vitro evolution has now been developed for enzyme engineering. For example, the Tetrahymena ribozyme, an RNA enzyme that typically catalyzes sequence-specific phosphoester transfer reactions that result in cleavage or ligation of RNA substrates, is useful in the within-described in vitro evolutionary process.

Figure 3:
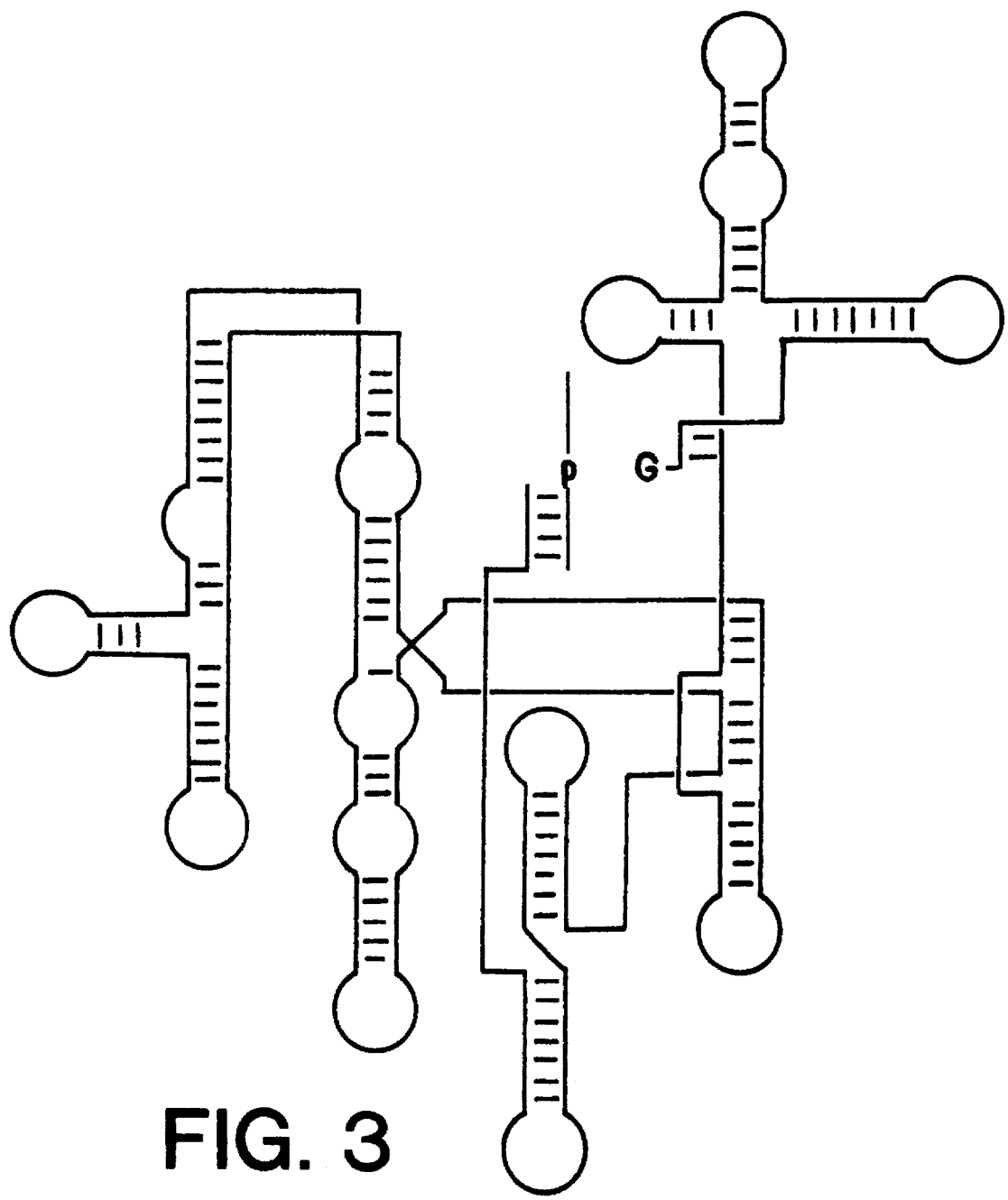
FIG. 3 illustrates the secondary structure of the Tetrahymena ribozyme (L-21 form) and also shows regions that were randomly mutagenized, as described further in Example 1 (boxed segments).

Darwinian evolution requires the repeated operation of three processes: (a) introduction of genetic variation; (b) selection of individuals on the basis of some fitness criterion; and (c) amplification of the selected individuals. Each of these processes can be realized in vitro (Joyce, Id. (1989)). A gene can be mutagenized by chemical modification, incorporation of randomized mutagenic oligodeoxynucleotides, or inaccurate copying by a polymerase. (See, e.g., Cadwell and Joyce, in PCR Methods and Applications 2: 28–33 (1992); Cadwell and Joyce, PCR Methods and Applications 3 (Suppl.): S136–S140 (1994); Chu, et al., Virology 98: 168 (1979); Shortle, et al., Meth. Enzymol. 100: 457 (1983); Myers, et al., Science 229: 242 (1985); Matteucci, et al., Nucleic Acids Res. 11: 3113 (1983); Wells, et al., Gene 34: 315 (1985); McNeil, et al., Mol. Cell. Biol. 5: 3545 (1985); Hutchison, et al., PNAS USA 83: 710 (1986); Derbyshire, et al., Gene 46: 145 (1986); Zakour, et al., Nature 295: 708 (1982); Lehtovaara, et al., Protein Eng. 2: 63 (1988); Leung, et al., Technique 1: 11 (1989); Zhou, et al., Nucl. Acids Res. 19: 6052 (1991).) FIG. 3 illustrates the secondary structure of the Tetrahymena ribozyme (L-21 form) and also shows regions that were randomly mutagenized, as described herein.

The gene product can be selected, for example, by its ability to bind a ligand or to carry out a chemical reaction. (See, e.g., Joyce, Id. (1989); Robertson and Joyce, Id. (1990); Tuerk, et al., Id. (1990).) The gene that corresponds to the selected gene product can be amplified by a reciprocal primer method, such as the polymerase chain reaction (PCR). (See, e.g., Saiki, et al., *Science* 230: 1350–54 (1985); Saiki, et al., Science 239: 487–491 (1988).)

Alternatively, nucleic acid amplification may be carried out using self-sustained sequence replication (3SR). (See, e.g., Guatelli, et al., *PNAS USA* 87: 1874 (1990), the disclosures of which are incorporated by reference herein.) According to the 3SR method, target nucleic acid sequences may be amplified (replicated) exponentially in vitro under isothermal conditions by using three enzymatic activities essential to retroviral replication: (1) reverse transcriptase, (2) RNase H, and (3) a DNA-dependent RNA polymerase. By mimicking the retroviral strategy of RNA replication by means of cDNA intermediates, this reaction accumulates cDNA and RNA copies of the original target.

In summary, a continuous series of reverse transcription and transcription reactions replicates an RNA target sequence by means of cDNA intermediates. The crucial elements of this design are (a) the oligonucleotide primers both specify the target and contain 5' extensions encoding the T7 RNA polymerase binding site, so that the resultant cDNAs are competent transcription templates; (b) cDNA synthesis can proceed to completion of both strands due to the degradation of template RNA in the intermediate RNA-DNA hybrid by RNase H; and (c) the reaction products (cDNA and RNA) can function as templates for subsequent steps, enabling exponential replication.

A major obstacle to realizing Darwinian evolution in vitro is the need to integrate mutation and amplification, both of which are genotype-related, with selection, which is phenotype-related. In the case of RNA enzymes, for which genotype and phenotype are embodied in the same molecule, the task is simplified.

B. Procedures
1. Amplification
a. Amplification Method

Using a combination of two polymerase enzymes, it is possible to amplify virtually any RNA. (See Kwoh, et al., *PNAS USA* 86: 1173 (1989); Joyce, in *Molecular Biology of RNA: UCLA Symposia on Molecular and Cellular Biology*, T. R. Cech (ed.), Liss, N. Y., 1989, pp. 361–371.) RNA is copied to a complementary DNA (cDNA) with reverse transcriptase (RT), and the resulting cDNA is transcribed to RNA with T7 RNA polymerase (T7 Pol). (See FIGS. 2A–C).

Figure 2A:
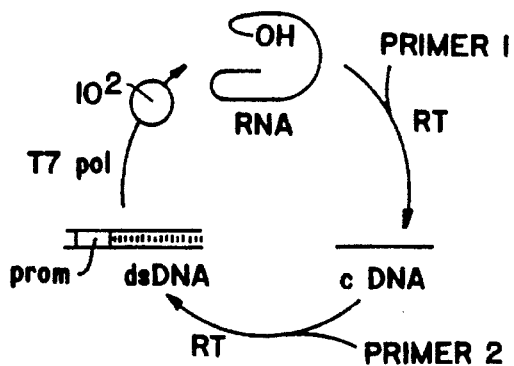
FIGS. 2A and 2B illustrate the general procedure for selective amplification of catalytic RNA.
Figure 2B:
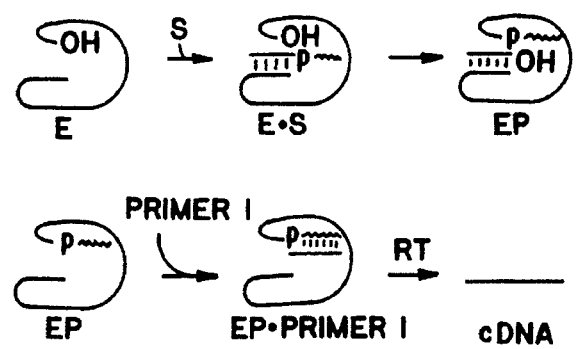

FIGS. 2A and 2B illustrate the general procedure for selective amplification of catalytic RNA (i.e., enzymatic RNA molecules of the present invention). In FIG. 2A, the overall procedure for RNA amplification is shown. "RT"= reverse transcriptase; "T7 pol"=T7 polymerase; "prom"= promoter, and "RNA" represents the enzymatic RNA molecule. In FIG. 2B, the procedure for selective amplification based on phosphoester transfer activity of a group I ribozyme is shown. "E" represents the enzymatic RNA molecule; "S" represents substrate; "E·S" represents enzyme/substrate complex; and "EP" represents enzyme/ product complex.

Figure 2C:
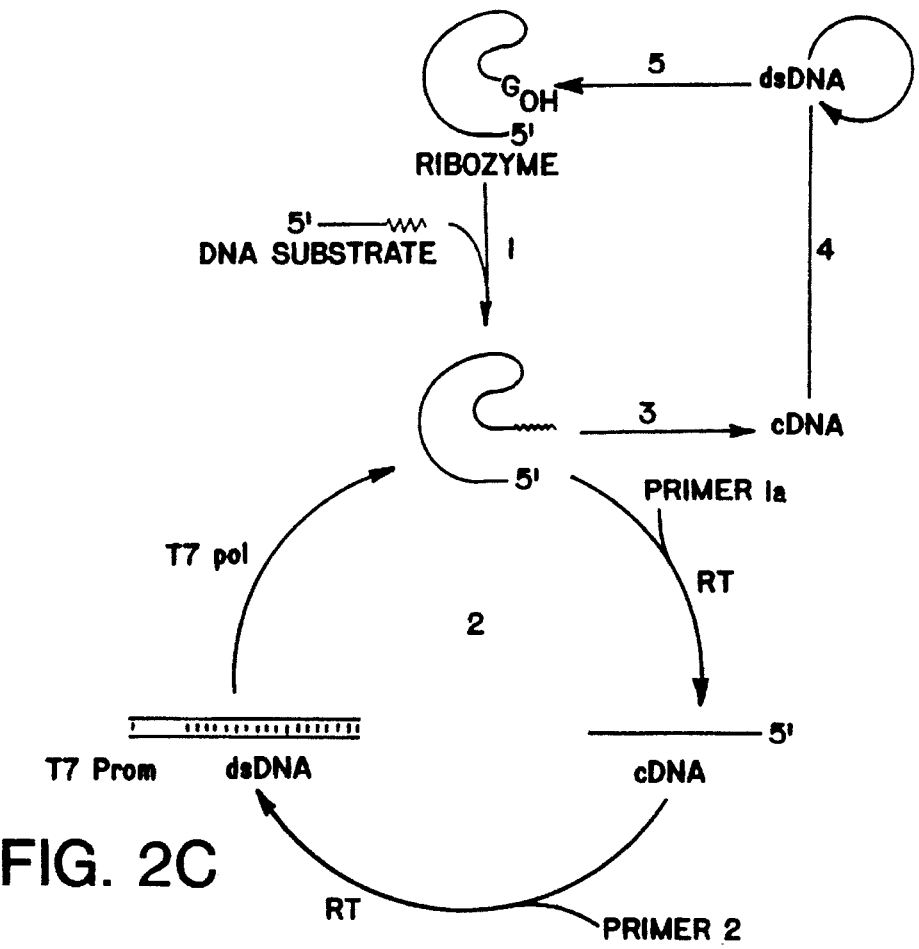
FIG. 2C illustrates the overall in vitro evolution procedure disclosed herein. 1—Cleavage of the DNA substrate via phosphoester transfer results in ligation of the 3' portion of the substrate to the 3' end of the ribozyme. 2—Selective isothermal amplification of DNA-cleaving ribozymes: first, selective Primer 1a hybridizes to the extended 3' terminus of active molecules and initiates cDNA synthesis in the presence of reverse transcriptase (RT); next, Primer 2, which contains a T7 promoter sequence, hybridizes to the cDNA and initiates second-strand DNA synthesis; finally, T7 RNA polymerase (T7 pol) produces multiple copies of the selected RNA, each of which can enter a new round of amplification. 3—Selective cDNA synthesis employing Primer 1a and reverse transcriptase. 4—PCR amplification employing nonselective Primer 1b and Primer 2, restores the original terminus of the ribozyme-encoding gene and introduces occasional mutations. 5—In vitro transcription to produce the progeny population of ribozymes.

FIG. 2C illustrates the overall in vitro evolution procedure disclosed herein, in the context of a DNA-cleaving enzyme, which is used as a convenient example. 1—Cleavage of the substrate via phosphoester transfer results in ligation of the 3' portion of the substrate to the 3' end of the ribozyme. 2—Selective isothermal amplification of DNA-cleaving ribozymes: first, selective Primer 1a hybridizes to the extended 3' terminus of active molecules and initiates cDNA synthesis in the presence of reverse transcriptase (RT); next, Primer 2, which contains a T7 promoter sequence, hybridizes to the cDNA and initiates second-strand DNA synthesis; finally, T7 RNA polymerase (T7 pol) produces multiple copies of the selected RNA, each of which can enter a new round of amplification. 3—Selective cDNA synthesis employing Primer 1a and reverse transcriptase. 4—PCR amplification employing nonselective Primer 1b and Primer 2, restores the original terminus of the ribozyme-encoding gene and introduces occasional mutations. 5—In vitro transcription to produce the progeny population of ribozymes.

The foregoing "steps" are further detailed in sections 1.b, 2 and 3 immediately below, where the processes of mutation, selection and amplification are described at length. In general, though, selective amplification of active molecules occurs during transcription (as described in step 2 above) as a consequence of the ability of T7 RNA polymerase to generate 200 to 1200 copies of RNA transcript per copy of cDNA template (Chamberlin, et al., in *The Enzymes*, Vol. 15, P. D. Boyer (ed.), Academic Press, New York, 1982, pp. 87–108).

The amplification reaction is generally performed in a single test tube at a constant temperature of 37° C., resulting in an increase of $10^3$ to $10^6$ times the original input of RNA after one hour (Guatelli, et al., *PNAS USA* 87: 1874 (1990); Joyce, in *Antisense RNA and DNA*, J. A. H. Murray (ed.), Wiley-Liss, New York, 1992, pp. 353–372). A useful procedure for RNA amplification is described in Beaudry and Joyce, Id. (1992).

b. Example

The population of DNA-cleaving ribozymes obtained after 9 generations of in vitro evolution (see Beaudry and Joyce, Id. (1992)) was used as starting material. It should be understood, however, that ribozymes generated as described in Example 3 below may also be utilized as starting material.

Ribozymes (0.1 μM) and substrate (0.2 μM) are incubated at 37° C. for 1 hr in a 100 μl volume containing 10 mM $MgCl_2$ and 30 mM EPPS (pH 7.5). After ethanol precipitation, a portion of the reaction products (10–50%) was added to a 20 μl isothermal amplification reaction mixture, containing 10 mM $MgCl_2$, 80 mM KOAc, 50 mM Tris (pH 7.5), 5 mM DTT, 2 mM each NTP, 0.2 mM each dNTP, 4 μCi [α-$^{32}$P]GTP, 12.5 U/μl MoMLV reverse transcriptase, 50 U/μl T7 RNA polymerase, and 20 pmol each of appropriate primers; the mixture was then incubated at 37° C. for 2 hours. In experiments designed to optimize DNA cleavage activity, primers 5'-TTTATTTATTTATTT-3' (Primer 1a, SEQ ID NO 6) and 5'-CTGCAGAATTCTAATACGACT-CACTATAGGAGGGAAAAGTTATCAGGC-3' (Primer 2, SEQ ID NO 7), were used. Primer 1a hybridizes to the 3' portion of the substrate that becomes attached to the 3' end of the ribozyme. (Primer 1b has the sequence 5'-CGAG-TACTCCAAAACTAATC-3' (SEQ ID NO 8); primer 1b hybridizes to the 3' portion of the ribozyme when no substrate or product remains attached. Primers 1a and 1b, when used, perform similarly.) Primer 2 hybridizes to the 3' end of the resulting cDNA and introduces the T7 promoter sequence.

2. Selection

Amplification is performed selectively in that individual RNAs in the population are required to catalyze a particular chemical reaction in order to become eligible for amplification (Joyce, Id. (1989); Robertson and Joyce, Id. (1990); Beaudry and Joyce, Id. (1992)). One exemplary selection criterion was based on the ability of group I ribozymes to catalyze a sequence-specific phosphoester transfer reaction involving an oligonucleotide (or oligodeoxynucleotide) substrate. FIG. 2B illustrates the procedure for selective amplification based on phosphoester transfer activity of a group I ribozyme. One exemplary procedure for selective amplification based on phosphoester transfer activity of a group I ribozyme is described in Beaudry and Joyce, Id. (1992). Another is essentially as follows.

Twenty-five percent of the isothermal amplification products were used to generate cDNA in a 20 µl reaction mixture containing 10 mM MgCl$_2$, 50 mM Tris (pH 7.5), 5 mM DTT, 2 mM each NTP, 0.2 mM each dNTP, 0.2 U/µl AMV reverse transcriptase and 20 pmol Primer 1a, incubated at 37° C. for 1 hr. Approximately 5–10% of the resulting cDNA was amplified by the PCR in a 100 µl reaction mixture containing 1.5 mM MgCl$_2$, 50 mM KCl, 10 mM Tris (pH 8.3), 0.1% gelatin, 0.2 mM each dNTP, 20 pmol Primer 1, 20 pmol Primer 2, and 2.5 U Taq DNA polymerase, carried out for 30 cycles of 92° C. for 1 min, 45° C. for 1 min, and 72° C. for 1 min, and 1 cycle of 72° C. for 10 min. Primer 1b is complementary to the 3' end of the ribozyme, allowing regeneration of its original, active form. PCR DNA (~250–500 ng, 5–10% of the total) then served as template in an in vitro transcription reaction, carried out in a 25–50 µl volume. Error-prone or mutagenic PCR may also be used to generate a higher percentage of variants.

Similarly, when the selection criterion is the ability to bind one or more amino acids, the foregoing procedure is modified to enable the identification and isolation of ribozymes with amino-acid-containing substrate still attached thereto. For example, one or more amino acids in the substrate—e.g., the terminal amino acids—may be "tagged" for identification purposes, via art-recognized procedures. One preferred method of "tagging" or "labeling" substrate amino acid(s) involves biotinylation, according to procedures known in the art. (See, e.g., Green, et al., *Biochem. J.* 125: 781 (1971); Lomant and Fairbanks, *J. Mol. Biol.* 104: 243–261 (1976); and Mouton, et al., *Arch. Biochem. Biophys.* 218: 101–108 (1982).) Various reagents and kits for biotinylating amino acids, polypeptides, and proteins are commercially available (see, e.g., the biotinylation kits from Pierce Chemicals, Rockford, Ill.).

Ribozymes with biotinylated amino acid—containing substrate (or product) attached thereto are then easily identified with the use of a detecting means such as a solid matrix or solid surface containing avidin bound thereto or incorporated therein. For example, a sample containing ribozymes admixed with amino acid-containing substrate, wherein said substrate is terminally labeled with biotin, may be run across avidin tips, to "pull out" ribozymes with amino acids or polypeptides attached thereto. Molecules labeled with biotin may easily be detected with indirect immunofluorescence techniques. In addition, a number of fluorochromes, as well as alkaline phosphatase and horseradish peroxidase (which produce colored precipitates) are available directly conjugated to avidin. Streptavidin-fluorochrome conjugates are also useful in the identification of molecules labeled with biotin and are readily available from various commercial sources (e.g., Pierce Chem.).

Samples collected after exposure to avidin may subsequently be subjected to further procedures to separate ribozymes with amino acid-containing product attached thereto from amino acid-containing molecules that are not linked to a ribozyme. Such separations may be done using routine methods, e.g., via size separation or via use of a variety of well-known labeling agents and methods. (See, e.g., Ausubel, et al. (eds.), *Current Protocols in Molecular Biology*, John Wiley & Sons, Inc. (1994).)

Once the selected enzymatic RNA molecules (i.e., the ribozymes with attached product) are separated out, they may be prepared for a subsequent amplification step. Preferably, before amplification is initiated, the amino acid-containing product is allowed to dissociate from the ribozyme. As previously noted, adjustment of the pH of the solution may enhance or slow down this dissociation process. Once the ribozymes are "free" of attached amino acid-containing product, amplification may be initiated, using appropriate primers, as previously described.

Alternatively, enzymatic RNA molecules capable of binding a particular amino acid (or acids) may be identified and removed from a population sample using a column containing one or more amino acids linked to a column matrix, or via other art-recognized methodologies. For example, if one is seeking to isolate arginine-binding ribozymes, one may take about 20 µg of random $^{32}$P-labeled ribozymes in water, heated at 65° C. for 5 minutes, with the salt concentration adjusted to the appropriate level. The RNA is then cooled to 4° C. over a ten-minute period before the RNA solution in a 25 µL total volume is loaded onto the affinity column. The column, which contains, e.g., an L-arginyl-L-cysteine dipeptide linked through the sulfhydryl group to a thiopropyl Sepharose 6B column matrix (Pharmacia, Piscataway, N.J.), is washed at 4° C. for approximately 8–12 column volumes, and any remaining RNA sticking to the column is eluted with 50 mM L-arginine in column buffer. cDNA is then synthesized from the arginine-eluted RNA, amplified via PCR, and transcribed into RNA for the next cycle of amplification. (See, e.g., Connell et al., *Biochemistry* 32: 5497–5502 (1993).)

It should also be noted that one may adjust the reaction parameters to diminish hydrolysis—thus increasing the persistence of the intermediate—e.g., by decreasing the pH of the admixture.

Methods of selecting individuals from the population will vary, depending upon the selection criteria applied. For example, if selection of ribozymes that are able to cleave DNA is desired, one may wish to prepare primers that will amplify ribozymes when the DNA-containing product is still attached to the ribozyme. Conversely, when the predetermined selection criterion is the identification of ribozymes with amide-cleaving ability, one may elect to prepare primers that will amplify ribozymes after the amino acid-containing product has dissociated from the ribozyme.

Therefore, if the predetermined selection criterion is the identification of amide bond-cleaving enzymatic RNA molecules, the process may be described as follows: (1) obtain a population of ribozymes and place them in an appropriate receptacle; (2) add amide bond-containing substrate molecules to the receptacle, to form an admixture of ribozyme and substrate; (3) maintain the admixture for a sufficient period of time and under predetermined reaction conditions to allow the ribozymes and substrate to interact, to form ribozyme-product complexes; (4) separate the ribozyme-product complexes from the admixture; (5) allow the ribozyme and product to dissociate from each other; and (6) purify or otherwise separate the ribozymes from the product.

As described herein, after step (1), the population may optionally be exposed to mutagenizing conditions before continuing to step (2). Also as described herein, the selection and separation steps may take advantage of known procedures, e.g., the use of biotin labeling of the product and the use of an avidin-coupled support to select out and separate ribozyme-product complexes from the remainder of the admixture. It is also contemplated that the ribozymes identified in step (6) may then be amplified, or may be run through the entire stepwise process one or more subsequent times, e.g., with different selection criteria applied each time. It should also be apparent that the foregoing is exemplary and is not intended to limit the scope of the invention.

With regard to amplification, the transcribed RNA is generally isolated by polyacrylamide gel electrophoresis, visualized by UV shadowing, cut and eluted from gel, purified on duPont NENsorb (duPont de Nemours, Wilmington, Del.), and quantified spectrophotometrically, as described herein. The entire process is generally repeated 18 times, the first 9 as described in section 1 above and the second 9 with the incubation time for the cleavage reaction reduced from 1 hr to 5 min. Occasionally, the cDNA was purified to improve the quality of the PCR amplification. To do so, cDNA was synthesized as above except in the presence of 25–50 μCi [α-$^{32}$P]dATP. Labeled cDNA was isolated by electrophoresis in a 5% polyacrylamide/8M urea gel, visualized by autoradiography, cut and eluted from gel, and purified on duPont NENsorb.

PCR products are purified by extraction with chloroform and isoamyl alcohol and by precipitation with ethanol, and are used to transcribe RNA as described in section 3 below. The product of such a reaction is a molecule that contains the 3' portion of the substrate attached to the 3' end of the ribozyme (EP; see FIGS. 2A and 2B). Selection occurs when an oligodeoxynucleotide primer is hybridized across the ligation junction and used to initiate cDNA synthesis. The primer does not bind to unreacted starting materials (<$10^{-8}$ compared to reaction products) and thus leads to selective amplification of the catalytically active RNAs.

3. Introduction of Variation

Mutations are introduced in two ways. First, at the outset, a set of mutagenic oligodeoxynucleotides that contain random substitutions at a fixed frequency of occurrence is used. These partially randomized oligodeoxynucleotides are produced on an automated DNA synthesizer with nucleoside 3'-phosphoramidite solutions that have been doped with a small percentage of each of the three incorrect monomers (McNeil, et al., Id. (1985); Hutchison, et al., Id. (1986)). Second, after each round of selective amplification, random mutations are introduced by performing the PCR under mutagenic conditions (Cadwell and Joyce, *PCR Methods and Applications* 2: 28–33 (1992); Cadwell and Joyce, *PCR Methods and Applications* 3 (Suppl.): S136–S140 (1994)).

To generate the initial population of ribozyme variants, random mutations are introduced throughout the catalytic core of the molecule. In one example, four synthetic oligodeoxynucleotides are prepared, each of which randomly mutagenizes 35 nucleotide positions at an error rate of 5% per position (not shown). The transcription conditions are essentially as follows: 2 pmol of DNA template (containing mutagenic oligodeoxynucleotides), 2 mM NTP's, 15 mM MgCl$_2$, 2 mM spermidine, 5 mM DTT, 50 mM tris-HCl (pH 7.5), 1500 U of T7 RNA polymerase are admixed to a volume of 60 μl and held at 37° C. for 2 hours. RNA is purified by electrophoresis in a 5% polyacrylamide-8M urea gel and subsequent column chromatography on Sephadex G-50.

The degenerate oligodeoxynucleotides are incorporated into a DNA template that encodes the ribozyme, and the template is transcribed directly to produce the mutant RNAs (Joyce and Inouye, *Nucl. Acids Res.* 17: 711 (1989)). Twenty pmol ($10^{13}$ molecules) of material is used at the beginning. Thus, the generation 0 population is expected to contain the wild-type ribozyme, all possible 1-, 2-, 3-, and 4-error mutants, and a sampling of the higher-error mutants (see Table 2 in Example 4 below).

In general, when using PCR procedures, each primer works in combination with a second primer to amplify a target nucleic acid sequence. The choice of PCR primer pairs for use in PCR is governed by various considerations, as discussed herein. That is, the primers have a nucleotide sequence that is complementary to a sequence conserved in the gene of choice. Useful priming sequences have been disclosed herein (e.g., primers 1, 1b, and 2). The strategy used for cloning the selected genes will depend, as is well known in the art, on the type, complexity, and purity of the nucleic acids making up the various genes. Other factors include whether or not the genes are to be amplified and/or mutagenized.

Typically, the exemplary genes are comprised of polynucleotide strands, such as mRNA, cDNA, or the sense strand of genomic DNA, although antisense strands, rRNA, or tRNA may also be used in PCR. If the polynucleotide sequence is in the form of double stranded genomic DNA, it is usually first denatured, typically by melting, into single strands. A gene sequence is subjected to a PCR reaction by treating (contacting) the sequence with a PCR primer pair, each member of the pair having a preselected nucleotide sequence. The PCR primer pair is capable of initiating primer extension reactions by hybridizing to nucleotide sequences, preferably at least about 10 nucleotides in length and more preferably at least about 20 nucleotides in length, conserved within the gene sequence. Primer extension via PCR may be carried out from either end of the molecule, through the amide or through the carboxyester, as desired.

The PCR reaction is performed by mixing the PCR primer pair, preferably a predetermined amount thereof, with the nucleic acids of the selected gene or DNA nucleotide sequence, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing a plurality of different DNA homologs.

The PCR reaction is performed using any suitable method. PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990). *Thermus aquaticus* DNA polymerase I, which is useful in PCR, is described in U.S. Pat. No. 4,889,818.

Restriction sites may also be incorporated into the 5' and 3' primers to enable the amplification products to be subcloned into sequencing or expression vectors. It may also be helpful to place a 4-base spacer sequence proximal to the restriction site to improve the efficiency of cutting amplification products with enzymes.

In the presently-described examples, PCR was performed under standard reaction conditions, resulting in an error rate of approximately 0.1% per position per generation. A mutagenic, modified PCR procedure that provides an error rate of 0.66±0.13% per position (95% confidence level) has also been developed. (See Cadwell and Joyce, *PCR Methods and Applications* 2:28–33 (1992), and Cadwell and Joyce, *PCR Methods and Applications* 3 (Suppl.): S136–S140 (1994), the disclosures of which are incorporated herein by reference.) The RNAs obtained by selective amplification are subjected to reverse transcription, the resulting cDNAs are PCR amplified, and the PCR products are transcribed to produce a progeny distribution of mutant RNAs.

Integration of the PCR with the selective RNA amplification procedure is useful in three other ways. First, it increases the overall amplification by about $10^3$ times. Second, it simplifies the process of subcloning individuals from the evolving population. Normally, only a small portion of the DNA in the RNA amplification mixture is fully double-stranded, but with the PCR, the amount of double-stranded DNA (dsDNA) is greatly increased. Third, it returns the RNA to a form that can participate in the RNA-catalyzed phosphoester transfer or amide-cleavage reaction. After phosphoester transfer or amide cleavage, the ribozyme has the 3' portion of the substrate attached to its 3' end, and after selective RNA amplification, the substrate sequence remains attached for a time (see FIGS. 2A and 2B). However, by subsequent use of PCR, followed by in vitro transcription, the original 3' end of the ribozymes is restored.

Therefore, the entire mutation, selection and amplification process—i.e., the method of engineering enzymatic RNA molecules capable of cleaving an amide bond—may conveniently be described according to the following stepwise procedure.

1. Obtain a population of ribozymes;
2. Introduce genetic variation into the population;
3. Identify individuals from the resulting "mutant" population that are able to meet predetermined selection criteria;
4. Separate the identified (or selected) individuals from the remainder of the population;
5. Prepare appropriate primers; and
6. Amplify the selected individuals.

The foregoing steps may be repeated as many times as desired to generate numerous variant populations. In various embodiments, it is contemplated that the amplified population produced in step six will be used as the "starting population" in the next "generation" beginning with step one.

As those of skill in the art will appreciate, step 5 need not be performed in the time sequence indicated. That is, primers may be prepared at any time; presumably, preparation of primers is based on understanding of the predetermined selection criteria. For example, if the predetermined selection criterion is the identification of ribozymes that are able to cleave DNA, one may wish to prepare primers that will amplify ribozymes when the DNA-containing product is still attached to the ribozyme. Conversely, when the selection criterion is the identification of ribozymes with amide-cleaving ability, one may elect to prepare primers that will amplify ribozymes after the amino acid-containing product has dissociated from the ribozyme.

4. Substrate Cleavage Activity

The entire series of events, beginning with a heterogeneous population of RNAs, proceeding with RNA catalysis in the target reaction, selective amplification of catalytically active RNAs, reverse transcription of the selective amplification products, mutagenic PCR, and in vitro transcription to produce a progeny distribution of RNAs, is referred to as one "generation". Typically, a generation is completed in one to two working days, excluding time for analytic work. The initial population of mutant RNAs is referred to as "generation 0", while subsequent populations are referred to as "generation 1", "generation 2", and so forth. In principle, there is no limit to the number of successive generations that can be obtained.

Typically, each generation begins with 20 pmol of RNA. The amount of RNA is again quantified after selective amplification and after transcription.

In practice, there is always the danger of developing a "parasite" that circumvents the selection criterion and is amplified more efficiently than the most reactive species. For example, a sequence may arise which allows false hybridization of one of the amplification primers at an internal site, generating a species with a nucleotide deletion that may be amplified more efficiently than the full-length ribozyme. Thus, it is important to monitor the populations generated and remove such "parasites", if and when they appear.

Substrate cleavage activity for the population as a whole is generally monitored via gel electrophoresis assay involving cleavage of [5'-$^{32}$P]-labeled substrate to yield a specific product. Cleavage of the substrate ("S") in the absence of enzyme, in the presence of the wild-type Tetrahymena ribozyme (L-21 form), and in the presence of the population of RNAs obtained at each generation ($G_n$, beginning with a value of 0 for n) is measured.

Reaction conditions will vary depending on various parameters, e.g., substrate recognition, affinity, cleavage, etc. In general, reaction conditions are essentially as follows: 0.5 μM ribozyme, 0.1 μM substrate (2.6 μCi/pmol), 30 mM EPPS (pH 7.5), and 10 mM $MgCl_2$ are admixed and maintained at 37° C. for about 1 hour. Reaction products are separated by electrophoresis in a 20% polyacrylamide-8M urea gel, of which autoradiograms are made.

One usually expects that any given mutation will more likely be detrimental than beneficial, although there may be a substantial number of neutral mutations. Through successive generations, however, continued improvement of phenotype is observed to occur, and in succeeding generations, the rate of improvement is expected to increase.

RNAs from each generation are usually purified by polyacrylamide gel electrophoresis and Sephadex chromatography. To provide a more formal assay of cleavage activity, [5'-$^{32}$P]-labeled substrate was prepared as follows, and formation of both the ribozyme-coupled covalent intermediate and the RNA-catalyzed site-specific cleavage product is measured. (See also Inoue, et al., *J. Mol. Biol.* 189: 143 (1986).)

Cleavage of $^{32}$P-labeled substrate is generally conducted under reaction conditions as described hereinabove prior to autoradiogram. Substrate (S), enzyme/product (EP), and product (P) are separated by electrophoresis in a 20% polyacrylamide-8M urea gel. Individual bands are cut from the gel and quantitated by Cerenkov counting. On the average, five replicate experiments are performed on three different days with two different preparations of substrate, before data points are plotted (not shown).

5. Preparation and Sequencing of Subclones

Although evolution in natural populations is an accomplished fact, evolution in vitro is a work in progress that allows the experimenter to access any time period in evolutionary history. Subclones are obtained from the evolving population at every generation and individual ribozymes are then sequenced.

a. Preparation of Subclones

One useful method of preparing subclones is described in Beaudry and Joyce, *Science* 257: 635–641 (1992). For example, DNAs used to transcribe the population of RNAs at each generation are amplified in a second PCR reaction with appropriate primers, producing a 435-bp (base pair) fragment with unique restriction sites at its ends. The fragment was digested with Eco RI and Hind III and ligated into a pUC18 vector that had been linearized with Eco RI and Hind III and purified in a 1.5% agarose gel. (See Beaudry and Joyce, Id. (1992).) The resulting plasmid DNAs were used to transform competent DH5α-F' cells (see Hanahan, in *DNA Cloning: A Practical Approach*, D. M. Glover, ed., IRL Press, Oxford, 1985, pp. 109–135), which were then grown on ampicillin-containing plates. Individual colonies were chosen at random and grown overnight in liquid media. DNA was prepared by the boiling lysis method (Holmes, et al., *Anal. Biochem.* 114: 193 (1981)) and screened for the insert by restriction digestion.

Another useful method of preparing subclones is as follows. Subclones were obtained using the Invitrogen TA Cloning Kit (Invitrogen, San Diego, Calif.). The PCR DNA at G27 was ligated into a linearized plasmid, and the resulting DNA was used to transform competent INVαF' cells, which were grown on ampicillin/X-gal plates. Individual colonies containing the insert were identified by their white color, chosen at random, and grown overnight in liquid media. Plasmid DNA was prepared by the boiling, lysis method (Holmes & Quigley, *Anal. Biochem.* 114: 193–197 (1981)) and screened for the presence of insert by restriction digestion.

b. Sequencing

As noted above, subclones may be obtained from the evolving population at every generation. Specific generations may also be chosen for detailed analysis. The nucleotide sequence of the entire ribozyme gene is determined for each of these subclones essentially as follows.

Cloned individuals are generally sequenced by the dideoxy chain-termination method (Sanger, et al., *PNAS USA* 74: 5463 (1977); Beaudry and Joyce, Id. (1992); Zagursky, et al., *Gene Anal. Tech.* 2: 89 (1985)) with reciprocal primers 5'-GTAAAACGACGGCCAGT-3' (SEQ ID NO 9) and 5'-CATGATTACGAATTCTA-3' (SEQ ID NO 10), which are compatible with the pUC plasmid. Sequencing reactions utilized modified T7 DNA polymerase (Sequenase, USB) and [$^{35}$S] (α-thiophosphate) dATP and were analyzed by electrophoresis in a 6% polyacrylamide-8M urea gel. Nucleotide sequences of individual subclones were also obtained (not shown).

Individual ribozymes were prepared as follows: the gene encoding the ribozyme was amplified by the PCR using Primer 1b and Primer 2; the resulting DNA was used as a template for in vitro transcription; the RNA products were isolated by polyacrylamide gel electrophoresis, and were purified and quantified as described above. (See also Tsang and Joyce, *Biochemistry* 33: 5966–5973 (1994).)

Analysis of the determined sequences indicates how genotype changes over the course of evolutionary history. From generation 0 to generation 3, variation introduced into the original ribozyme template by the use of mutagenic primers to produce generation 0 is discarded throughout much of the catalytic core of the ribozyme. The mean number of mutations per subclone decreased from 7.0 at generation 0 to 2.7 at generation 3. By generation 3, a small number of mutations outside of the original zone of random mutation in the catalytic core of the ribozyme have occurred because of ongoing mutation events. The consensus sequence still tends to be that of the wild type. Analysis of subsequent generations suggests that accumulation of mutations coincides with improvement in the phenotype of the population as a whole. The mean number of mutations per subclone is also observed to increase, as a larger proportion of subclones adopt the common mutations and as mutations accumulate outside of the original zone of random mutation.

The relation between genotype and phenotype in the context of an RNA-based evolving system can readily be formalized once catalytic, kinetic, and comparable data are collected and analyzed. Genotype can be represented as a matrix A, the rows corresponding to individuals in the population and the columns corresponding to functionally significant positions within the nucleotide sequence. An exemplary analysis is illustrated in Beaudry and Joyce, *Science* 257: 635–641 (1992).

The data obtained from a relatively small number of individuals may not be sufficient to provide a meaningful solution to the relation of genotype to phenotype, even for those nucleotide positions that are known to be most significant based on their high frequency of accepted mutation. One may then elect to use an appropriate weighing vector as a guide to help decide which mutations are sufficiently important to warrant individual study. (See, e.g., Beaudry and Joyce, Id. (1992).)

6. Site-Directed Mutagenesis

Individual enzymatic RNA molecules containing single or multiple point mutations may be prepared via site-directed mutagenesis for analysis of the relative significance of a particular mutation. Catalytic activity is then studied with an appropriate [5'-$^{32}$P]-labeled oligodeoxyribonucleotide substrate. Site-directed mutagenesis is carried out essentially as described in Morinaga, et al., *Biotechnology* 2: 636 (1984), which may be described as follows.

Plasmid pT7L-21 (Zaug, et al., *Biochemistry* 27: 8924 (1988)) is digested with either (i) Eco RI and Hind III to remove the ribozyme coding region, or (ii) Bsa I and Xmn I to remove the ampicillin-resistance gene. The resulting fragments are purified in a 1% agarose gel and cross-hybridized in the presence of a 5'-phosphorylated synthetic oligodeoxynucleotide that introduces the desired mutation. The annealing mixture typically contains 0.06 pmol of pT7L-21 (ΔEcoRI-HindIII), 0.06 pmol pT7L-21(ΔBsaI-XmnI), 15 pmol of mutagenic oligodeoxynucleotide, 40 mM Tris-HCl (pH 7.2), and 8 mM MgSO$_4$ in 12-μl volume, which is heated to 100° C. for three minutes, then incubated at 30° C. for 30 minutes, and 0° C. for 10 minutes.

The annealing product is made fully double-stranded with the Klenow fragment of *E. coli* DNA polymerase I (Boehringer-Mannheim, Indianapolis, Ind.) and T4 DNA ligase (U.S. Biochemical, Cleveland, Ohio) and is then used to transform competent DH5α-F' cells, which are grown on ampicillin-containing plates. Colonies are screened by the colony hybridization method with [5'-$^{32}$P]-labeled mutagenic oligodeoxynucleotide as a probe (Grunstein, et al., *PNAS USA* 72:3961 (1975)). DNA is prepared from positive colonies and sequenced throughout the ribozyme gene, as described above.

RNA is subsequently prepared from the DNA template by in vitro transcription, which is performed essentially as follows. Transcription conditions: 2 pmol of DNA template (containing mutagenic oligodeoxynucleotides), 2 mM nucleotide triphosphates (NTPs), 15 mM MgCl$_2$, 2 mM spermidine, 5 mM dithiothreitol (DTT), 50 mM tris-HCl (ph 7.5), 1500 U of T7 RNA polymerase; 60 μl volume; 37° C., 2 hours. RNA is purified by electrophoresis in a 5% polyacrylamide-8M urea gel and subsequent column chromatography on Sephadex G-50.

The foregoing procedures may be repeated as many times as desired to produce enzymatic RNA molecules having one or more point mutations at one or more preselected sites. For example, in addition to use of the within-disclosed in vitro evolution methods to design and identify ribozymes capable of binding amino acids in a polypeptide sequence and cleaving the bond linking adjacent amino acids at a predetermined site, one may use site-directed mutagenesis techniques as disclosed herein to modify the active site on an enzymatic RNA molecule to accomplish the same objective.

For example, one may use the within-disclosed techniques to modify the recognition site on a preselected ribozyme, e.g., by altering the nucleotide sequence of said site to exactly duplicate, or substantially mimic, a consensus nucleotide sequence which is able to bind one or more particular amino acids. Exemplary consensus sequences which may be incorporated into the recognition site of enzymatic RNA molecules according to the within-disclosed methods are available in the art and include those described in Connell, et al., *Science* 264: 1137–1141 (1994); Connell, et al., *Biochemistry* 32: 5497–5502 (1993); and Famulok, *J. Am. Chem. Soc.* 116: 1698–1706 (1994), to name a few examples. Other useful sequences may be identified using the methods described herein; for example, see section B.2 above.

7. Kinetic Analysis

Reduction in reaction time tends to favor selection of enzymatic RNA molecules with increased $k_{cat}$ values. Representative ribozymes may be chosen from the evolving population and analyzed at each generation to determine $k_{cat}$ and $K_M$ values for the individuals selected. It is to be appreciated that the $k_{cat}$ and $K_M$ values of the selected ribozymes are not necessarily equivalent to the average values for the entire population, however.

Cleavage reactions are generally carried out at 37° C. in 10 mM $MgCl_2$, 30 mM EPPS (pH 7.5), and 40 µg/µl BSA, using (5'-$^{32}$P)-labeled substrate. BSA is added to prevent oligonucleotides from adhering to the walls of the 500 µl Eppendorf tubes, and does not affect the course of the reaction. Ribozyme and substrate are preincubated separately for 15 min at 37° C., and then mixed to initiate the reaction. Typically, 5 aliquots of 3–10 µl each are removed from the reaction mixture at specified times and quenched by addition to 1–2 volumes of an ice-cold mixture containing 8M urea, 50–100 mM EDTA, 0.05% xylene cyanol, 0.05% bromophenol blue, 10% SDS, 9 mM Tris-borate (pH 8.3), and 20% sucrose. Substrate and product are separated by electrophoresis in a 20% polyacrylamide/8M urea gel, visualized by auto-radiography, excised from gel, and quantified by Cerenkov counting.

$K_M$ and $k_{cat}$ values are determined in experiments with substrate (S) in excess over ribozyme (E). Initial rates of reaction ($V_o$), over a range of substrate concentrations, are estimated from the initial linear phase, generally the first 5% or less of the reaction. Typically 8 data points were fit by a least squares method to a theoretical line given by the equation: $v=K_M (v_o/[S])+V_{max}$.

Single-turnover experiments are performed with ribozyme in excess of substrate (Herschlag & Cech, *Biochemistry* 29: 10159–10171 (1990b)). Initial rates ($k_{obs}$) are obtained using no more than the first 5% of the reaction. Given that $k_{cat}/K_M=k_{obs}/[E]$, each $k_{obs}$ value, obtained at different ribozyme concentrations, provided an estimate of $k_{cat}/K_M$. Generally 8 or more measurements of $k_{cat}/K_M$ are obtained.

Specific catalytic properties of an amide-cleaving ribozyme can be optimized by appropriate manipulation of the selection constraints during an in vitro evolution procedure. For example, beginning with a heterogeneous population of ribozymes, enriched for modest amide bond-cleavage activity, successive generations are produced to obtain ribozymes with amidase activity that have successively-improved catalytic rates and substrate binding affinities.

8. Determination of Binding Constants

The equilibrium dissociation constant, $K_D$, of the complex between ribozyme and product (P) is determined by gel-shift analysis in a native polyacrylamide gel (Pyle et al., *PNAS USA* 87:8187–8191 (1990)). Ribozyme at twice final concentration is preincubated at 37° C. for 15 min in 10 mM $MgCl_2$ and 30 mM EPPS (pH 7.5) before mixing with an equal volume of 0.05–1 nM (5'-$^{32}$P)-labeled DNA product in 10 mM $MgCl_2$, 30 mM EPPS (pH 7.5), 0.05% xylene cyanol, 3% glycerol, and 80 µg/µl BSA. The mixture is allowed to equilibrate at 37° C. for 15–60 min before loading on a 10% polyacrylamide gel containing 10 mM $MgCl_2$ and 30 mM EPPS (pH 7.5). The electrophoresis buffer also contains 10 mM $MgCl_2$ and 30 mM EPPS (pH 7.5). The gel is run at 6 milliamps in a 37° C. room until the sample has entered the gel (~10 min), and is then moved into a 4° C. cold room where the current is increased to 30 milliamps. This is done to prevent the temperature of the gel from rising above 37° C. The ribozyme-product complex and free product are visualized by autoradiography, cut from the gel, and quantified by Cerenkov counting.

A binding curve is generated by plotting the percentage of product bound to ribozyme (% bound) over a range of ribozyme concentrations. $K_D$ is determined by fitting the data to a theoretical binding curve using a least squares method. Where ribozyme is in vast excess over product, the theoretical binding curve may be represented by the equation: % bound=$[E]/([E]+K_D)$, where $K_D=[E]$ when half of the total product is bound to the ribozyme.

The substrate need not be a nucleotide or nucleotide analog. The only requirement is that RNAs that react with the substrate become tagged in some way so that they can be distinguished from nonreactive molecules with respect to the amplification process. For example, reactive RNAs could become joined to a portion of the substrate that is attached to a solid support, while nonreactive RNAs would be washed away, leaving the bound RNAs to be selectively amplified. These and other methodologies are further described elsewhere herein.

9. Extension of Directed Evolution to Develop Additional Evolved Species

As an in vitro model of Darwinian evolution, a population of macromolecular catalysts was directed toward the expression of novel catalytic function. In the Examples presented herein, the development of ribozymes that cleave DNA and those that demonstrate amide bond-cleaving activity with improved efficiency under physiologic conditions has now been demonstrated.

a. Evolution In Vitro

Beginning with any generation of a population of ribozymes as described herein, successive generations of in vitro evolution are carried out. Variation in the population is maintained by PCR amplification, which introduces mutations at a rate of ~0.1% per nucleotide position per generation. Because mutation is ongoing, evolution based on Darwinian principles can occur. Progeny ribozymes have the opportunity to acquire new mutations that confer favorable attributes not possessed by the parent molecules. This phenomenon is reflected by the steadily increasing frequency of accepted mutations over subsequent generations (not shown).

b. Improvement of Substrate Binding Affinity

Beginning with any generation of enzymatic RNA molecules, the concentration of substrate is lowered—e.g., from 10 µM to 0.2 µM—to impose increased selection pressure favoring individuals with enhanced substrate binding affinity. In order to assess the impact of this change, $K_D$ values for the complex between ribozyme and product are determined for the population of ribozymes at regular intervals, e.g., at every third generation.

It is anticipated that, when the within-disclosed procedures are followed, improvement in substrate binding affinity over successive generations of in vitro evolution may be observed.

The product, rather than substrate, is employed to avoid a cleavage reaction during the gel-shift analysis. The binding affinity for the product is assumed to be similar to that of the substrate, based on previous studies showing that the wild-type ribozyme binds the RNA substrate with the same affinity as it binds the product (Pyle et al., *PNAS USA* 87: 8187–8191 (1990); Herschlag & Cech, *Biochemistry* 29:10159–10171 (1990b)).

EXAMPLE 2

Enzymatic RNA Molecules With Amide-Cleaving Activity

Enzymatic RNA molecules (or ribozymes) have now been developed which are capable of cleaving amide bonds—e.g., inactive alkyl amide bonds—via a metal-dependent hydrolytic mechanism. This is comparable to the reaction carried out by protease/peptidase enzymes, which enzymes typically consist of protein themselves.

There have been reports in the literature describing artificial enzymes that promote cleavage of an activated aryl amide; for example, Janda, et al., *Science* 241: 1188–1192 (1988) describe an antibody with amidase activity. While this is not an insignificant development, it nonetheless involves a protein with enzymatic activity and the bond cleaved is not a peptide bond. There has also been a report showing that a modified Tetrahymena ribozyme has modest ability to accelerate hydrolysis of an aminoacyl ester under certain circumstances (Piccirilli, et al., *Science* 256: 1420–1424 (1992)). This reaction is easily accomplished by a common hydrolysis reaction, however, in the absence of enzyme. Conversely, it is the amide hydrolysis reaction that demands a catalyst.

In contrast, the enzymatic RNA molecules disclosed herein catalyze cleavage of an unactivated alkyl amide, which is more akin to the amide linkage within a polypeptide. Furthermore, the within-disclosed molecules, which exhibit amide-cleaving activity, are not themselves proteins.

While the present example employs substrates containing the amide linkage in the context of an oligodeoxynucleotide-polypeptide "hybrid" molecule, with 8 nucleotides upstream and one or more amino acids downstream of the target amide, it is anticipated that any amide-linkage-containing molecule recognized or recognizable by an enzymatic RNA molecule of the present invention may be cleaved as disclosed herein—including polypeptides and proteins. In addition, since the ribozyme binds the substrate via Watson-Crick pairing and tertiary contacts involving the upstream nucleotides present in hybrid molecules, thereby drawing the amide into close proximity to a bound $Mg^{2+}$ cofactor, it is expected that sequential replacement of said upstream nucleotides with amino acids within the framework of the in vitro evolutionary methods disclosed in Example 1 above will produce a ribozyme that binds tightly to polypeptide molecules.

The present invention is also uniquely useful in facilitating the engineering and selection of catalytically active RNA molecules which are able to cleave a specific amide bond at a desired location; in other words, the present invention permits the construction of a vast array of RNA molecules, each having the ability to cleave a specific peptide bond between particular, preselected amino acids. The advantages of being able to efficiently and expeditiously design enzymes of such specificity are inestimable. The present invention is also advantageous in that it obviates the need to screen a significant number of organisms or constructs in an effort to identify a suitable protease; using the methods disclosed herein, one of skill in the art may now design and construct molecules with the desired specificity and activity.

Additionally, as there are no essential contacts with the downstream nucleotides, it is likely that the downstream amino acids can be replaced with other amino acids, peptides, or polypeptides, or with other chemical substituents. Converting an enzymatic RNA molecule to a full-fledged amide bond-cleaving molecule that recognizes, binds and cleaves a polypeptide may be accomplished using the within-disclosed in vitro evolution techniques, selecting for ribozymes that retain amide-cleaving activity and bind a particular protein. (Also see Tuerk and Gold, *Science* 249: 505–510 (1990); and Jellinek, et al., *PNAS USA* 90: 11227–11231 (1993).)

The enzymatic RNA molecules with the ability to cleave target amides are preferably prepared according to in vitro evolution methods such as those described in Example 1 herein. Thus, while the ribozymes disclosed herein may alternatively be described as having the ability to cleave a particular phosphoester bond in the context of a ribonucleotide, deoxyribonucleotide, or some other nucleotide-containing substrate (e.g. an arabinonucleotide substrate), it has now been observed that when the evolved ribozymes are presented with a substrate that contains an amide in place of a phosphate, they catalyze cleavage of the amide to generate products with free amine and free carboxyl termini.

In order to stimulate the progressive evolution of enzymatic RNA molecules capable of cleaving amide bonds between neighboring amino acids, various "hybrid" molecules—e.g. molecules comprising a series of one or more nucleotides linked to a series of one or more amino acids—are first synthesized as described hereinbelow. Such molecules may then be used to identify useful enzymatic RNA molecules according to the present invention.

A. Synthesis of Ribozymes and Substrates

1. Synthesis of Oligonucleotides

The procedure for preparation of the oligonucleotide segment of a hybrid molecule, e.g., d($GGCCCTCT_{NH2}$) (SEQ ID NO 11), is described essentially as follows.

The 7-mer d(GGCCCTC) (SEQ ID NO 12) was prepared on an automated DNA synthesizer, deprotected in the usual way, and purified by polyacrylamide gel electrophoresis and subsequent affinity chromatography on duPont NENsorb (duPont, Wilmington, Del.). The $T_{NH2}$ residue was provided in the form of 3'-amino'3'deoxythymidine-5'-triphosphate (U.S. Biochemical, Cleveland, Ohio) and was coupled enzymatically to the 7-mer using terminal deoxynucleotidyl transferase (TdT; available from U.S. Biochemical, Cleveland, Ohio or BRL, Gaithersburg, Mass.), producing the desired 8-mer product.

The 8-mer was purified by polyacrylamide gel electrophoresis and subsequent affinity chromatography. The 8-mer was found to migrate appreciably slower than the unreacted 7-mer (data not shown). Finally, the purified 8-mer was [$5'$-$^{32}P$]-using [$\gamma$-$^{32}P$]ATP and T4 polynucleotide kinase, according to standard protocols. (In general, the labeling admixture comprised 2 μl 5× buffer, 1 μl 8-mer, 1 μl $\alpha$-$^{32}$P-ATP, 4 μl $H_2O$, and 2 μl T4 kinase, and was maintained at 37° C. for 1 hour.)

Figure 7:
FIG. 7 is a photograph of a gel illustrating cleavage of a hybrid oligonucleotide-oligopeptide substrate by enzymatic RNA molecules of the present invention. In lane 1, 5'-labeled 8-mer marker is shown. In lane 2, interaction of ribozyme with a 5'-labeled hybrid substrate generates an 8-mer 5' product with a terminal —NH$_2$. In lane 3, substrate alone (i.e., in the absence of ribozyme) is shown.

As shown in FIG. 7, this 8-mer d($GGCCCTCT_{NH2}$) (SEQ ID NO 11) marker and the 8-mer 5' product of the enzymatic RNA molecule-catalyzed cleavage of the amide-bond-containing substrate have the same mobility. This effectively demonstrates the amide-cleaving activity of the enzymatic RNA molecules of the present invention.

2. Preparation of Ribozymes

Enzymatic RNA molecules identified herein as clones 48 and 61 were used in the within-described cleavage experiments, although it is to be appreciated that the present invention is not limited to use of said ribozymes. Clones 48 and 61 were optimized for DNA-cleavage ability and were prepared as described in Example 1 (and in Beaudry and Joyce, *Science* 257: 635–641 (1992) and Tsang and Joyce, *Biochemistry* 33: 5966–5973 (1994)). Ribozymes from clones 48 and 61 were selected from the 27th generation.

Ribozymes 48 and 61 (G27 #48 and G27 #61) are described as follows. Ribozyme G27 #48 includes the following mutations at the sites noted: 44:G→A, 51/52:insert AGAA, 87:A→del, 94:A→U, 115:A→U, 116:G→A, 166:C→A, 170:C→U, 188:G→A, 190:U→A, 191:G→U, 205:U→C, 215:G→A, 239:U→A, 312:G→A, 350:C→U, and 364:C→U. Ribozyme G27 #61 has the following mutations: 44:G→A, 51/52:insert AGAA, 87:A→del, 94:A→U, 115:A→U, 116:G→A, 166:C→A, 170:C→U, 188:G→A, 190:U→A, 191:G→U, 205:U→C, 215:G→A, 313:G→C, and 314:A→G.

Ribozyme G27 #48 includes the following mutations, which are not present in G27#61: 239:U→A, 312:G→A, 350:C→U, and 364:C→U. Similarly, ribozyme G27 #61 includes the following mutations, which are absent in G27 #48: 313:G→C and 314:A→G.

3. Synthesis of Hybrid Molecules

As noted above, an oligonucleotide is first prepared. Next, that nucleotide sequence "head" is linked, via an amide bond, to an amino acid residue sequence "tail" to form a hybrid substrate molecule. Preferably, an entire "series" of hybrid molecules is prepared for use in a continuing in vitro evolutionary process, whereby the first molecule in an exemplary series may comprise an oligonucleotide sequence (e.g., an 8-mer) linked to a polypeptide (e.g., a monomer or dimer) by an amide bond. For an example, a first hybrid molecule in such a series may comprise an oligonucleotide 8-mer linked to a polypeptide dimer. Subsequent hybrid molecules in such a series preferably comprise one fewer nucleotide each time—e.g., the second molecule in the series comprises an oligonucleotide 7-mer linked to a polypeptide trimer; the third molecule comprises an oligonucleotide 6-mer linked to a polypeptide tetramer; and so on, until only a single nucleotide remains at the "head" of the hybrid molecule. Exemplary hybrid molecules in such a "series" may be used in a consecutive manner in conjunction with in vitro evolution methodologies as disclosed herein to identify useful enzymatic RNA molecules in successive rounds of mutation, selection, and amplification.

It is also to be understood that although peptide monomers, dimers, and so forth are described as exemplary, a hybrid molecule according to the present invention may comprise longer and more complex polypeptide sequences. That is, hybrid molecules of the present invention may include as few as one or two amino acid residues, or may include substantially longer polypeptides or proteins, provided that the length of the polypeptide "tail" does not substantially interfere with the ability of enzymatic RNA molecules of the present invention to recognize and bind hybrid molecules, or otherwise interfere with cleavage of amide bonds therein.

It should also be appreciated that the sequence of nucleotides and/or amino acids may be varied as desired. For example, the nucleotide sequence at the "head" of the hybrid may be comprised of common and/or unusual or modified nucleotides (as described in 37 CFR §§1.821 et seq.), in any order. Similarly, while certain exemplary hybrid molecules disclosed herein include pairs of identical amino acids in the "tail" sequence, it is expressly to be understood that the amino acid residue sequence of hybrid molecules according to the present invention may be varied, and may include unusual or modified amino acids, as well.

Hybrid molecules according to the present invention are typically designed and constructed so that the nucleotide and amino acid sequences are linked by an amide bond. In general, methods such as those described by Zieboll and Orgel, *J. Mol. Evol.* 38: 561–565 (1994) and Ehler, et al., *Biochim. et Biophys. Acta* 434: 233–243 (1976) the disclosures of which are incorporated by reference herein—were used and adapted as follows.

Typically, a 0.5M solution of imidazole is first prepared, into which the amino acid of choice is dissolved. In the present example, arginine (L-arginine, 98% purity; Aldrich Chem. Co., Milwaukee, Wis.) was dissolved into a 0.5M imidazole solution, until a final concentration of arginine of 0.1M was achieved. Next, 125 µl of the arginine solution was placed into an Eppendorf tube. Two microliters (2 µl) of oligonucleotide is then placed into a separate, clean Eppendorf tube, dried (e.g. via spin-vac), and cooled (e.g., placed on ice). In the present example, 2 µl of radiolabeled d(GGC-CCTCT-$_{NH2}$) (SEQ ID NO 11)—synthesized as described in section 1 above—was placed into a separate, clean Eppendorf tube, dried, and placed on ice.

Approximately 0.1 mg 1, 1'-carbonyldiimidazole ("CDI"; Aldrich, Milwaukee, Wis.) was measured and added into 0.1M arginine solution; CDI served to "activate" the amino acids. (See Ehler, et al., Id. (1976).) As soon as the CDI dissolved into the solution, the admixture was placed on ice for about 1 minute. About 20 µl of the above-noted solution was added to the tube containing the d(GGCCCTCT-$_{NH2}$) (SEQ ID NO 11), on ice (i.e., at about 0° C.). The tube containing this admixture was then transferred into a cold room and incubated. At various time points (e.g. 30 minutes, 60 minutes), 10 µl of sample was removed, quenched with 2× gel loading buffer, and placed on ice. Half of each sample (from each time point) was loaded on an 8M urea-20% polyacrylamide gel, and run according to standard protocols, as described previously.

Figure 6:
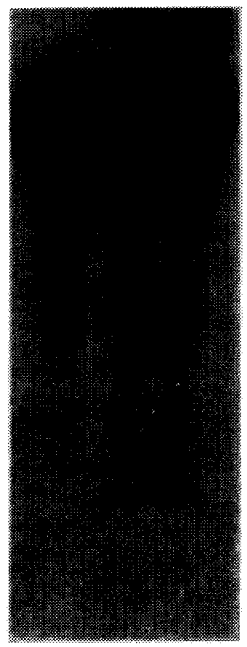
FIG. 6 illustrates the confirmation of successful synthesis of the oligonucleotide-oligopeptide "hybrid". In lane 1, 5labeled d(GGCCCTCT$_{NH2}$) is shown. In lanes 2 and 3, 5'-labeled d(GGCCCTCT)-Arg is shown, as measured at 30 and 60 minutes.

FIG. 6 illustrates the confirmation of successful synthesis of an exemplary oligonucleotide-oligopeptide "hybrid". In lane 1, 5'-labeled d(GGCCCTCT$_{NH2}$) is shown. In lanes 2 and 3, 5'-labeled d(GGCCCTCT)-Arg is shown, as measured at 30 and 60 minutes.

Two hybrid molecules synthesized as described above were isolated and used in cleavage reactions conducted essentially as described below. The first molecule, identified herein as "oligo-Arg", had the sequence d(GGCCCTCT)-Arg (SEQ ID NO 13); the second molecule, "oligo-Arg$_2$", had the sequence d(GGCCCTCT)-ArgArg (SEQ ID NO 14).

It is expressly to be understood, however, that the hybrid and polypeptide substrates cleavable by enzymatic RNA molecules of the present invention are not limited to those containing arginine residues only. Substrates lacking arginine, and/or substrates further comprising common or unusual/modified amino acids (preferably in L-form) are also contemplated by the within-disclosed invention. For example, amino acids listed in the Table of Correspondence appearing in Section A of the Detailed Description are useful in the hybrid and polypeptide substrates of the present invention, as are those described in 37 CFR §1.822.

Hybrid oligonucleotide-oligopeptide molecules useful in the in vitro evolution procedures disclosed herein may also include uncommon amino acids, variants of "common" amino acids, or amino acid analogs, e.g., β-alanine, S-adenosylmethionine, S-adenosylcysteine, S-adenosyl-homocysteine, L(+)-canavanine, hydroxyproline, methioninemethylsulfoniumchloride, and w-nitroarginine. (See also Zieboll and Orgel, *J. Mol. Evol.* 38:561–565 (1994).)

4. Amide, Polypeptide and Protein Substrates

As disclosed herein, the enzymatic RNA molecules of the present invention may be engineered to cleave a bond between adjacent amino acids, with great selectivity and specificity. Any amide, polypeptide or protein substrate, whether naturally-occurring (i.e. "native"), synthesized, derivatized, or conjugated, is an appropriate substrate for the enzymatic RNA molecules disclosed herein.

An amide substrate is a compound which includes a scissile amide bond. Preferred amide substrates include peptides and peptide conjugates having an amide linkage between a secondary amine and a terminal peptide carboxy group. 2-'Amino 3'-deoxyribose is a preferred secondary amine. When the ribozyme hydrolyzes an amide substrate, it produces an amino cleavage product and a ribozyme-acyl intermediate, i.e., a ribozyme amidase intermediate. The amino cleavage product includes the secondary amine, e.g., 2'-amino 3'-deoxyribose or a peptide fragment having a free amino terminus. A preferred ribozyme amidase intermediate includes an ester linkage between a ribozyme hydroxyl group and the terminal carboxyl group of a peptide. The peptide may include one or more amino acid residues. Additionally, the peptide may be linear or cyclic and may include non-natural amino acids and amino acids incapable of ribosomal translation. Furthermore, the amino acid residues may be either the D or L isomer.

Alternative amide substrates include amide linked glycopeptides and carbohydrates containing acetylated amino sugars, e.g., 2-acetamido-N-(L-aspart-4-oyl)-2-deoxy-β-D-glucopyranosylamine or asparaginyl-N-acetylglucosamine. Cleavage of either of these amide substrates yields an amino sugar as the amino cleavage product. Cleavage of N-acetyl amino sugars produces a ribozyme amide intermediate having an acetylated deoxynucleotide. Cleavage of glycopeptides produces a ribozyme amide intermediate having an ester linkage between a ribozyme hydroxyl group and a peptide carboxyl group. The peptide carboxyl group may be a terminal carboxyl group or an aspartic acid or glutamic acid residue. Amide linked glycans, including peptidoglycans, are yet a further class of amide substrate cleavable by amidase active ribozymes.

Although polypeptides of any length are cleavable using RNA enzymes of the present invention, one seeking to design a specific enzymatic RNA molecule according to the present invention may find it convenient to utilize shorter, rather than longer, polypeptides in the initial stages of in vitro evolution. For example, while polypeptides comprising 12 or fewer amino acids (e.g., dimers, tetramers, 8-mers, etc.) are discussed herein as exemplary, it is expressly to be understood that the invention is not so limited.

A polypeptide used as disclosed herein can be derived from an existing source (e.g. via proteolysis of a larger polypeptide or protein) or synthesized by any of the peptide synthetic techniques known to those skilled in the art. A summary of some of the techniques available can be found in J. M. Stuard and J. D. Young, "Solid Phase Peptide Synthesis", W. H. Freeman, Co., San Francisco (1969); J. Meinhofer, "Hormonal Proteins and Peptides" Vol. 2, pp. 46, Academic Press (New York) 1983; E. Schroder and K. Kubke, "The Peptides", Vol. 1, Academic Press (New York), 1965 for classical solution synthesis, and U.S. Pat. No. 4,631,211, the disclosures of which are incorporated herein by reference.

When a polypeptide desired for use according to the present invention is relatively short (i.e., less than about 25–50 amino acid residues in length) direct peptide synthetic techniques are generally favored, usually by employing a solid phase technique such as that of Merrifield (*JACS* 85: 2149 (1963)). Appropriate protective groups usable in the aforementioned syntheses are described in the above texts and in J. F. W. McOmie, *Protective Groups in Organic Chemistry*, Plenum Press, New York, 1973, which is incorporated herein by reference.

A polypeptide useful as disclosed herein can also be synthesized by recombinant DNA techniques. Such recombinant techniques are favored especially when the desired polypeptide is relatively long (greater than about 50 amino acids residues in length). When recombinant DNA techniques are employed to prepare an instant polypeptide, a DNA segment encoding the desired polypeptide is incorporated into a preselected vector that is subsequently expressed in a suitable host. The expressed polypeptide is then preferably purified by a routine method such as gel electrophoresis, immunosorbent chromatography, and the like.

Again, while initial rounds of in vitro evolution may conveniently be conducted using small polypeptides—e.g., during the selection process—it should be appreciated that enzymatic RNA molecules of the present invention may be engineered to recognize, bind and cleave polypeptides or proteins of a variety of lengths, conformations and biochemical or physical characteristics, by use of the within-disclosed techniques.

B. Cleavage of Hybrid Molecules

Six µl of hybrid molecule prepared as described, 2 µl of 5× low-$Mg^{2+}$ buffer, and 2 µl ribozyme were admixed and incubated at 37° C. for about 8 hours, or overnight. After incubation, a sample comprising approximately one-half of the admixture was labeled, loaded and run on an 8M urea-20% polyacrylamide gel, as before. A sample of 5'-labeled d(GGCCCTCT$_{NH2}$) (SEQ ID NO 11) was also run as a control.

Figure 4:
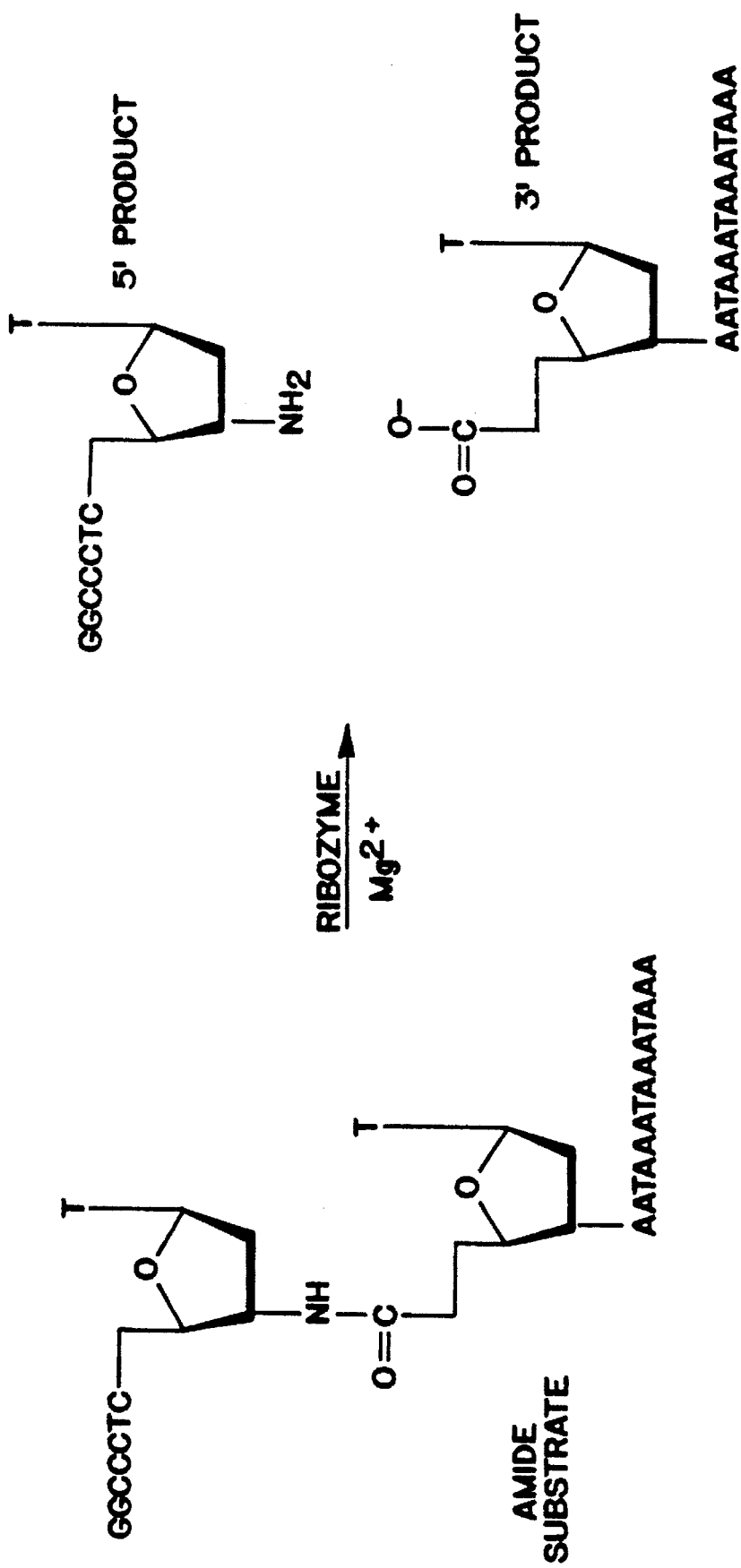
FIG. 4 illustrates the cleavage of an amide bond-containing substrate, showing that it generates a 5' product that carries a terminal amine and a 3' product that carries a terminal carboxyl.
Figure 5C:
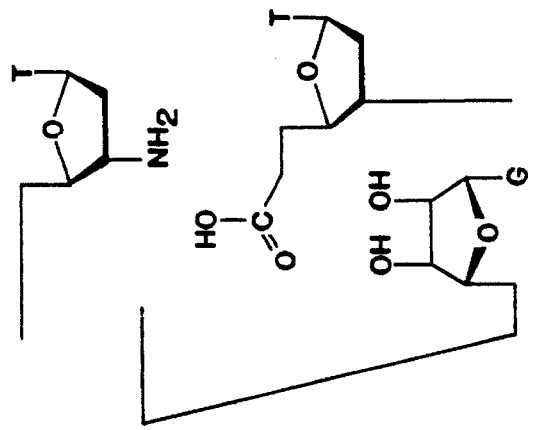
FIGS. 5A–C further illustrate the reaction shown in FIG. 4, including the production of intermediates (FIG. 5B) and products (FIG. 5C), as well as the relationship of the substrate to the ribozyme (FIG. 5A). It is also shown in FIG. 5C that the ribozyme-associated product is subsequently hydrolyzed, resulting in generation of a 5' product carrying a terminal amine and a 3' product carrying a terminal carboxyl. Subsequent to hydrolysis of the ribozyme-associated product, the enzyme is free to cycle.
Figure 5B:
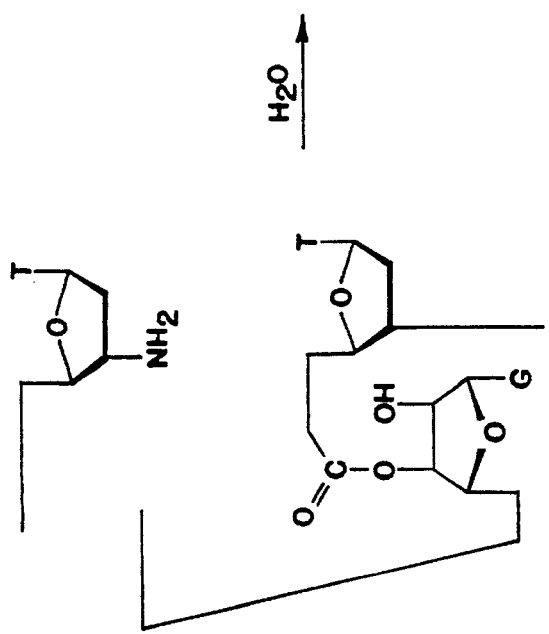
Figure 5A:
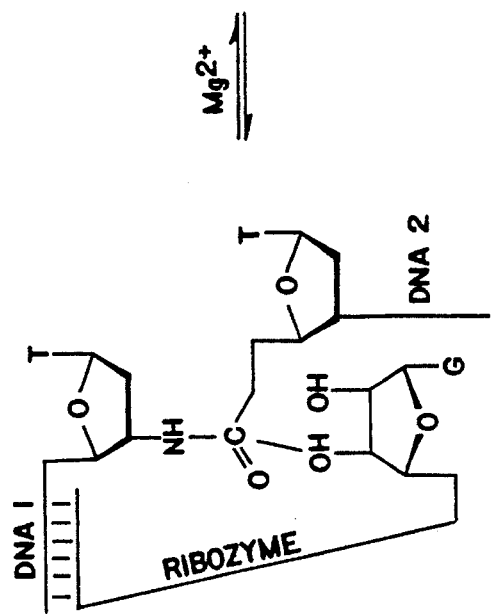

In FIGS. 4 and 5A–C, cleavage of a hybrid substrate by a ribozyme of the present invention is illustrated and shown to generate an 8-mer 5' product with a terminal -$NH_2$. For example, FIG. 4 illustrates the cleavage of an amide bond-containing substrate, showing that it generates a 5' product that carries a terminal amine and a 3' product that carries a terminal carboxyl. FIGS. 5A–C further illustrate the reaction shown in FIG. 4, including the production of intermediates (FIG. 5B) and products (FIG. 5C), as well as the relationship of the substrate to the ribozyme (FIG. 5A). It also shows that the ribozyme-associated product is subsequently hydrolyzed, resulting in generation of a 5' product carrying a terminal amine and a 3' product carrying a terminal carboxyl (FIG. 5C). Subsequent to hydrolysis of the ribozyme-associated product, the enzyme is free to cycle—i.e., it is free to cleave another amide bond. (See also Hentzen, et al., *Biochimica et Biophysica Acta* 281: 228–232 (1972).)

For purposes of illustration only, FIGS. 4 and 5 (A–C) have been drawn to show the amide bond in the context of an oligonucleotide molecule. It is expressly to be understood that one or both of the motifs identified in FIG. 5A–C as "DNA 1" and "DNA 2" may be replaced by the appropriate amino acid structural formulas and labels. For example, if the motif labeled "DNA 2" were replaced with the label "Arg" and the appropriate chemical drawing, the intermediate shown in FIG. 5B would illustrate that the arginine moiety remains temporarily attached to the ribozyme after the peptide bond is cleaved and is subsequently released via hydrolysis (FIG. 5C).

FIG. 7 illustrates the results of an exemplary ribozyme-catalyzed cleavage of a hybrid molecule. Typical reaction conditions are as follows: 1 μM ribozyme, 1 μM [5'-$^{32}$P]-labeled substrate, 10 mM $MgCl_2$, and 30 mM EPPS, at 37° C., pH 7.5, for 8 hours.

FIG. 7 is a photograph of a gel illustrating cleavage of a hybrid oligonucleotide-oligopeptide substrate by enzymatic RNA molecules of the present invention. In lane 1, 5'-labeled 8-mer marker is shown. In lane 2, interaction of ribozyme with a 5'-labeled hybrid substrate generates an 8-mer 5' product with a terminal —$NH_2$. In lane 3, substrate alone (i.e., in the absence of ribozyme) is shown.

As shown in FIG. 7, the 8-mer d($GGCCCTCT_{NH2}$) (SEQ ID NO 11) marker and the 8-mer 5' product of the enzymatic RNA molecule-catalyzed cleavage of the amide-bond-containing substrate have the same mobility. This effectively demonstrates the amide-cleaving activity of the enzymatic RNA molecules of the present invention.

The reaction appears to be dependent upon the presence of $Mg^{2+}$, although other divalent cations are also expected to be useful; for example, use of $Mn^{2+}$ instead of $Mg^{2+}$ also produced satisfactory results. In general, the reactions have been run at 37° C. for eight (8) hours or overnight, but it is expected that these parameters will continue to be adjusted as in vitro evolution techniques are applied. For example, selection of enzymatic RNA molecules that carry out the cleavage reaction during shorter time periods will likely be favored. Selection of enzymatic RNA molecules that utilize different monovalent or divalent cations may also be a useful choice.

Thus, as shown in FIG. 7, cleavage of hybrid oligonucleotide-oligopeptide substrate by enzymatic RNA molecules of the present invention has been confirmed.

It was observed that ribozyme G27 #48 cleaved the amide bond more rapidly than did G27 #61 (data not shown). It was also noted that the cleavage reaction rate decreases as the temperature is raised to 45° C. and ceases altogether at 50° C. (not shown). Unlike experiments involving oligonucleotide cleavage, it was observed that the ribozyme might occasionally cleave one position upstream of the bond "intended" to be cleaved in the hybrid molecule, but it did not cleave downstream of the amide bond. (See, e.g., Tsang and Joyce, *Biochemistry* 33: 5966–5973 (1994).) This "mis-cleavage" event is illustrated in FIG. 7, in lane 2, as evidenced by the band "beneath" the band representing the product generated when cleavage occurs at the desired (preselected) site. Such "mis-cleavage" events may be selectively eliminated from the evolving population, however; e.g., by going back the previous generation of variants and generating a different subpopulation therefrom, or by applying selection criteria designed to eliminate ribozymes that cleave at locations other than the one desired.

C. Cleavage of Polypeptide Molecules

The following general procedure is useful for confirming site-specific cleavage between preselected, adjacent amino acids. For example, to confirm that an enzymatic RNA molecule capable of site-specific cleavage of a bond between two arginine molecules has been identified, the following procedure may be used.

A small polypeptide substrate (e.g., an 8-mer) is prepared as described in section A.4 above and preferably includes a single paired Arg-Arg moiety. Six μl of the peptide substrate, 2 μl of 5× low-$Mg^{2+}$ buffer, and 2 μl ribozyme are admixed and incubated at 37° C. for about 8 hours, or overnight. Labeling of the polypeptide substrate will facilitate detection of reaction products and confirm site-specific cleavage, as described previously.

After incubation, a sample comprising approximately one-half of the admixture is loaded and run on an appropriate gel, as described above. A sample of substrate polypeptide, in the absence of enzyme, may be run as a control; a sample of expected cleavage product is also preferably run as a control. Examination of the results will confirm whether site-specific cleavage has occurred. Subsequent evaluations utilizing larger substrate polypeptides may be performed to further confirm site-specific cleavage between preselected amino acids.

EXAMPLE 3

Methods of Preparing Enzymatic RNA Molecules

A. Preparation of Wild-Type Ribozyme

The L-21 form of the Tetrahymena ribozyme was prepared by in vitro transcription of Hind III-digested pT7L-21 plasmid DNA (Zaug et al., *Biochemistry* 27: 8924–8931 (1988)). The transcription reaction mixture contained 0.1 μg/μl of cut plasmid, 15 mM $MgCl_2$, 2 mM spermidine, 50 mM Tris (pH 7.5), 5 mM DTT, 2 mM each NTP, 0.005 U/μl inorganic pyrophosphatase, and 25 U/μl T7 RNA polymerase, incubated at 37° C. for 2 hr. The 23-nucleotide 3' exon sequence was removed by RNA-catalyzed site-specific hydrolysis (Inoue et al., *J. Mol. Biol.* 189: 143–165 (1986)): RNA was incubated in the presence of 50 mM CHES (pH 9.0) and 10 mM $MgCl_2$ at 42° C. for 1 hr. The resulting RNA was isolated by electrophoresis in a 5% polyacrylamide/8M urea gel, visualized by UV shadowing, eluted from the gel overnight at room temperature in a buffer containing 200 mM NaCl, 10 mM Tris (pH 7.5), and 0.5 mM EDTA, and purified by affinity chromatography on duPont Nensorb (Wilmington, Del.). The concentration of ribozyme was determined spectrophotometrically, based on $e_{260}=3.2\times10^6$ $M^{-1}$ $cm^{-1}$ (Zaug et al., *Biochemistry* 27: 8924–8931 (1988)).

B. Alternative Methods of Preparing Ribozymes

One alternative method of preparing wild-type and mutant ribozymes may be described as follows. Wild-type and mutant ribozymes were produced by first isolating the 443 base-pair Eco RI to Hind III restriction endonuclease fragment from the plasmid PT7-21 described by Zaug et al., *Biochemistry* 27: 8924 (1988) using the standard methods described in *Current Protocols in Molecular Biology*, Ausubel et al., eds. John Wiley and Sons, New York (1987).

This 443 base-pair fragment contains the T7 promoter described by Dunn et al., *J. Mol. Biol.* 166: 477–535 (1983) and residues 22–414 of the Tetrahymena IVS and residues 1–25 of the 3' Tetrahymena exon described by Been et al., *Cell* 47: 207–216 (1986). This Eco RI and Hind III fragment was inserted into the M13 vector M13mp18 (which is similar to the vector described by Yanisch-Perron et al., *Gene* 33: 103–119 (1985)), which vector had been previously cleaved with Eco RI Hind III, according to standard subcloning procedures such as those described in *Current Protocols in Molecular Biology*, Ausubel et al, eds. John Wiley and Sons, New York (1987). The resulting M13T7L-21 DNA construct was used to transform *E. coli* host cells according to the transformation procedure described in *Molecular Cloning: A Laboratory Manual* (Maniatis et al., eds., Cold Spring Harbor Laboratories, Cold Spring Harbor, N.Y. (1989)).

Single-stranded DNA was then prepared from the M13T7L-21-transformed cells according to the procedures described in *Current Protocols in Molecular Biology* (Id., 1987). The accuracy of the above construction was confirmed by DNA sequencing using the Klenow fragment of *E.* coli DNA polymerase I (Boehringer Mannheim Biochemicals, Indianapolis, Ind.) and the dideoxynucleotide sequencing method (see Sanger et al., *PNAS USA* 74: 5463–5467 (1977)).

The wild-type and mutant ribozymes were prepared directly from the single-stranded M13T7L-21 DNA using a modification of the technique previously described by Joyce and Inoue, *Nucleic Acid Research* 17: 711–722 (1989). The technique involves construction of a template strand that optionally includes one or more mutagenic oligodeoxynucleotides. The resulting partially-mismatched double-stranded DNA is transcribed directly using T7 RNA polymerase.

Briefly, the procedure is as follows. A five-fold molar excess of a terminator polynucleotide and a mutator oligonucleotide were admixed with 5 μg of single-stranded M13T7L-21 DNA and a solution containing 20 mM tris [hydroxy-methyl]aminomethane adjusted to pH 7.5 with HCl(Tris-HCl), 50 mM NaCl and 2 mM $MgCl_2$. This solution was maintained at 70 degrees centigrade (70° C.) for 5 minutes and then steadily cooled to 30° C. over 40 minutes. Fifteen units(U) of T4 DNA ligase (U.S. Biochemicals, Cleveland, Ohio) and 7.5 U of T4 DNA polymerase (U.S. Biochemicals) were admixed into the solution, together with sufficient amounts of reagents to make a solution containing a final concentration of 20 mM Tris-HCl at pH 7.5, 50 mM NaCl, 5 mM $MgCl_2$, 2 mM dithiothreitol (DTT), 1 mM adenosine triphosphate (ATP), and 0.5 mM each of dGTP, dTTP, dATP and dCTP (dNTPs). The resulting solution was maintained at 37° C. for 60 minutes to complete the synthesis of the mutant strand. The resulting DNA was purified by ethanol precipitation and then used to direct the transcription of mutant RNA.

Transcription took place either in a 10 μl volume containing 18 g of mutant DNA, 2 μCi [$\alpha^{32}P$] GTP and 50 U of T7 RNA polymerase that was prepared as previously described by Davanloo et al., *PNAS USA* 81: 2035–2039 (1984), and the resulting product was purified according to a procedure originally developed by Butler & Chamberlain, *J. Bio. Chem.* 257: 5772–5779 (1982), or in a 400 μl volume containing 10 μg of mutant DNA, 40 μCi [$^3H$]UTP and 2,400 U of T7 RNA polymerase. In either case, the transcription mixture also contained 40 mM Tris-HCl at pH 7.5, 15 mM $MgCl_2$, 10 mM dithiothreitol, 2 mM spermidine, and 1 mM (each) NTPs, and was incubated at 37° C. for 90 minutes. The T7 RNA polymerase was extracted with phenol and the transcription products were purified by ethanol precipitation. The mutant RNA was isolated by electrophoresis in a 5% polyacrylamide/8M urea gel, eluted from the gel, and purified by ethanol precipitation and chromatography on Sephadex G-50.

The 3' exon sequence was removed by RNA-catalyzed site-specific hydrolysis as has been previously, Inoue et al., *J. Mol. Biol.* 189: 143–165 (1986). Briefly, the RNA was incubated in the presence of 50 mM CHES at pH 9.0 and 10 mM $MgCl_2$ at 42° C. for 1 hour. Wild-type and mutant RNAs were isolated by electrophoresis in a 5% polyacrylamide/8M urea gel, eluted from the gel, and purified by affinity chromatography on duPont Nensorb (duPont, Wilmington, Del.). RNAs were sequenced by primer extension analysis using AMV reverse transcriptase (Life Technologies, Inc., Gaithersburg, Md.) in the presence of dideoxynucleotides, using a modification of the methods described by Sanger et al. (*PNAS USA* 74: 5463–5467 (1977)), except for those containing the Delta P9 deletion (not shown), which were sequenced from the 3' end by partial RNase digestion, Donis-Keller et al., *Nucleic Acids Res.* 15: 8783–8798 (1987).

Other methods of preparing enzymatic RNA molecules of the present invention are based on chemical synthesis. Methods useful in the chemical synthesis of RNA are similar to those used to synthesize DNA. The additional 2'—OH group in RNA, however, requires a different protecting group strategy to deal with selective 3'-5' internucleotide bond formation, and with RNA susceptibility to degradation in the presence of bases.

The recently-developed method of RNA synthesis utilizing the t-butyldimethylsilyl group for the protection of the 2' hydroxyl seems to be the most reliable method for chemical synthesis of ribozymes. The method reproducibly yields RNA with the correct 3'-5' internucleotide linkages, with average coupling yields in excess of 99%, and requires only a two-step de-protection of the polymer.

Other useful methods are available. For example, published PCT application no. WO 93/23569 describes various methods of chemically synthesizing ribozymes.

EXAMPLE 4

Optimization of DNA Substrate Cleavage

The wild-type enzymatic RNA molecule, which can be "forced" to cleave a single-stranded DNA substrate (albeit only under conditions of high temperature (50° C.) or high $MgCl_2$ concentration (50 mM), or both), has now been "evolved" to produce variants that can cleave DNA under physiologic conditions with improved efficiency compared to the wild-type. (Robertson and Joyce, Id. (1990); Beaudry and Joyce, *Science* 257: 635–641 (1992).)

The catalytic efficiency of RNA-catalyzed DNA cleavage under physiologic conditions has recently been improved, thereby generating ribozymes that efficiently cleave DNA in vivo (Tsang and Joyce, *Biochemistry* 33: 5966–5973 (1994)). Since it is not obvious how one should change the Tetrahymena ribozyme to convert it from its "native" RNA-cleaving phenotype to a new phenotype, directed evolution was selected as a means to acquire the desired phenotype. Directed evolution is now discovered to be appropriate for use in designing and identifying enzymatic RNA molecules with DNA-cleaving ability, as well as amide-bond-cleaving and/or peptide-recognition and binding capabilities.

As described in the foregoing examples, to generate the initial population of ribozyme variants, random mutations are introduced throughout the catalytic core of the molecule. In one example, four synthetic oligodeoxynucleotides were prepared, each of which randomly mutagenizes 35 nucleotide positions at an error rate of 5% per position (not shown).

The following Table illustrates the composition of the initial population (generation 0). The probability P of having K errors in a doped oligonucleotide of length v and degeneracy d is given by: $P(k,v,d)=[v!/(v-k)!k!]d^k(1-d)^{v-k}$. A total of 140 positions were randomly mutagenized (v=140) at a degeneracy of 5% per position (d=0.05). The number of distinct k-error sequences of length v is given by: $N_k=[v!/(v-k)!k!]3^k$. The expected number of copies per sequence is based on a population size of 20 pmol ($1.2\times10^{13}$ molecules).

TABLE 2

| Errors | Probability (%) | Sequences | Copies/Sequence |
| --- | --- | --- | --- |
| 0 (wt) | 0.1 | 1 | $9 \times 10^9$ |
| 1 | 0.6 | 420 | $2 \times 10^8$ |

TABLE 2-continued

| Errors | Probability (%) | Sequences | Copies/Sequence |
|---|---|---|---|
| 2 | 2.1 | $9 \times 10^4$ | $3 \times 10^6$ |
| 3 | 5.0 | $1 \times 10^7$ | $5 \times 10^4$ |
| 4 | 9.0 | $1 \times 10^9$ | $9 \times 10^2$ |
| 5 | 12.8 | $1 \times 10^{11}$ | 15 |
| 6 | 15.2 | $7 \times 10^{12}$ | 0.3 |
| 7+ | 55.4 | | |

For example, in order to initiate the development of a population of ribozyme variants with optimized DNA-cleaving ability, the phylogenetically conserved portions of the molecule that are known to be essential for catalytic activity was first partially randomized. Superior DNA-cleaving ribozymes were distinguished from less active molecules based on the likelihood of attachment of the 3' portion of the substrate to the 3' end of the ribozyme. A DNA primer was hybridized across the ligation junction of successful reaction products, and used to initiate a selective isothermal amplification reaction. The selectively amplified molecules then served as templates for cDNA synthesis; the resulting cDNA was amplified by the polymerase chain reaction (PCR) (Saiki et al, Science 230: 1350–1354 (1985); Saiki et al, Science 239:487–491 (1988)); and the PCR products were transcribed to generate a new pool of RNAs. The entire process, beginning with the cleavage reaction and followed by selective isothermal amplification, cDNA synthesis, PCR amplification, and in vitro transcription, constitutes one "generation" of the in vitro evolution procedure.

This in vitro procedure was successfully used to generate over 40 successive generations, starting with a pool of $10^{13}$ variants of the Tetrahymena ribozyme. After the 9th generation (G9), individual ribozymes were isolated from the population and shown to catalyze the cleavage of a DNA substrate 100-fold more efficiently compared to the wild-type enzyme. This modest improvement in catalytic efficiency resulted from both an increased catalytic rate ($k_{cat}$) and a decreased value for the Michaelis constant ($K_M$).

For each generation, the evolving population was provided with 10 μM DNA substrate and allowed 1 hr to carry out the DNA-cleavage reaction. By G9, $K_M$ had improved from 6 μM for the wild-type to about 2 μM for the evolved individuals (Beaudry and Joyce, Id., (1992)). Accordingly, it appeared that the population was no longer under stringent selection pressure to drive further improvement of $K_M$. Individual cleavage rates, on the other hand, were on the order of 0.007 min$^{-1}$ by G9, still slow enough to be constrained by the 1 hr incubation period. However, if the reaction rate continued to improve, then the selection constraints would eventually become insufficient to favor further improvement of the catalytic rate. As successive generations of ribozymes were subjected to in vitro evolution, using different selection constraints, substantially greater DNA-cleavage activity was developed in members of the population in each successive generation.

In the present examples, in vitro evolution techniques have been applied each time with a higher level of sophistication and control. Because the outcome of an in vitro evolution experiment depends on the nature of the selection constraints, specific catalytic properties of a ribozyme, such as substrate binding affinity, catalytic rate, substrate specificity, and turnover, may be improved by appropriate manipulation of the reaction conditions. With this in mind, optimization of two catalytic properties of the DNA-cleaving ribozymes, namely, substrate binding affinity and catalytic rate was achieved. It was hypothesized that ribozymes with the greatest affinity for the substrate would enjoy a selective advantage when the substrate is presented at low concentrations. Under saturating conditions, ribozymes with the fastest first-order rate of reaction would be favored when the reaction time is very short.

For example, the concentration of the DNA substrate was first reduced 50-fold, to favor ribozymes with improved substrate binding affinity. Next, the reaction time was reduced 12-fold to favor ribozymes with improved catalytic rate. In both cases, the evolving population responded as expected, first improving substrate binding 25-fold, and then improving catalytic rate about 50-fold. The population of ribozymes has undergone 27 successive generations of in vitro evolution, resulting in, on average, 17 mutations relative to the wild-type that are responsible for the improved DNA-cleavage activity.

The previously-characterized G9 population of DNA-cleaving ribozymes (see Beaudry and Joyce, Id. (1992)) was "resurrected" and 27 additional generations of in vitro evolution were carried out under somewhat different reaction conditions. From generations 10 through 18, the substrate concentration was reduced 50-fold, from 10 μM to 0.2 μM. From generations 19 through 27, the lower substrate concentration was maintained and the reaction time was reduced 12-fold, from 1 hr to 5 min. On the basis of binding and kinetic studies, the population of ribozymes responded to each alteration of the selection constraints as predicted, becoming enriched with tighter substrate binders during generations 10–18, and then with faster catalysts during generations 19–27. Even more successive generations have been produced, and the in vitro evolutionary procedure continues.

A. Materials

Unlabeled nucleoside triphosphates (NTPs) and deoxynucleoside triphosphates (dNTPs) were purchased from Pharmacia (Piscataway, N.J.), and dideoxynucleoside triphosphates (ddNTPs) were from U.S. Biochemical (USB, Cleveland, Ohio). [α-$^{32}$P]GTP, [δ-$^{35}$P]ATP, and [$^3$H]UTP were from ICN Radiochemicals (Costa Mesa, Calif.). Synthetic oligodeoxynucleotides were obtained from Operon Technologies (Alameda, Calif.) and purified by polyacrylamide gel electrophoresis and subsequent chromatography on Sephadex G-25. Restriction enzymes and T4 polynucleotide kinase were from New England Biolabs (Beverly, Mass.), calf intestine phosphatase from Boehringer (Indianapolis, Ind.), AMV reverse transcriptase from Life Sciences (St. Petersburg, Fla.), MoMLV reverse transcriptase and Sequenase 2.0 (modified T7 DNA polymerase) from U.S. Biochemical, and Taq DNA polymerase from Cetus (Emeryville, Calif.). T7 RNA polymerase was prepared as previously described (Davanloo et al., PNAS USA 81: 2035–2039 (1984)) and purified according to a procedure originally developed for SP6 RNA polymerase (Butler and Chamberlain, J. Biol. Chem. 257:5772–5778 (1982)).

The L-21 form of the Tetrahymena ribozyme was prepared as described in Example 3 above.

B. In Vitro Evolution Procedure

In vitro evolution was carried out as described previously (see Example 1 above). While polymerase chain reaction (PCR) or self-sustained sequence replication (3SR) methods are both useful, the within-described methodology most closely resembles the 3SR method (see, e.g., Guatelli et al., PNAS USA 87: 1874–1878 (1990)). The mutagenic PCR method of Cadwell and Joyce (Id. (1994)) is also particularly preferred.

The population of DNA-cleaving ribozymes obtained after 9 generations of in vitro evolution in Example 1 above was used as starting material. Ribozymes (0.1 μM) and DNA substrate (0.2 μM) were incubated at 37° C. for 1 hr in a 100 μl volume containing 10 mM $MgCl_2$ and 30 mM EPPS (pH 7.5). After ethanol precipitation, a portion of the reaction products (10–50%) was added to a 20 μl isothermal amplification reaction mixture, containing 10 mM $MgCl_2$, 80 mM KOAc, 50 mM Tris (pH 7.5), 5 mM DTT, 2 mM each NTP, 0.2 mM each dNTP, 4 μCi [$\alpha$-$^{32}$P]GTP, 12.5 U/μl MoMLV reverse transcriptase, 50 U/μl T7 RNA polymerase, and 20 pmol each of 5'-TTTATTTATTTATTT-3' (Primer 1a, SEQ ID NO 21) and 5'-CTGCAGAATTCTAATACGACTCAC-TATAGGAGGGAAAAGTTATCAGGC-3' (Primer 2, SEQ ID NO 15), which was incubated at 37° C. for 2 hr. Primer 1 hybridizes to the 3' portion of the substrate that becomes attached to the 3' end of the ribozyme. (Primers 1a and 1b, when used, perform similarly.) Primer 2 hybridizes to the 3' end of the resulting cDNA and introduces the T7 promoter sequence.

Twenty-five percent of the isothermal amplification products were used to generate cDNA in a 20 μl reaction mixture containing 10 mM $MgCl_2$, 50 mM Tris (pH 7.5), 5 mM DTT, 2 mM each NTP, 0.2 mM each dNTP, 0.2 U/μl AMV reverse transcriptase and 20 pmol Primer 1a, incubated at 37° C. for 1 hr. Approximately 5–10% of the resulting cDNA was amplified by the PCR in a 100 μl reaction mixture containing 1.5 mM $MgCl_2$, 50 mM KCl, 10 mM Tris (pH 8.3), 0.1% gelatin, 0.2 mM each dNTP, 20 pmol 5'-CGAGTACTC-CAAAACTAATC-3' (Primer 1b, SEQ ID NO 9), 20 pmol Primer 2, and 2.5 U Taq DNA polymerase, carried out for 30 cycles of 92° C. for 1 min, 45° C. for 1 min, and 72° C. for 1 min, and 1 cycle of 72° C. for 10 min. Primer 1b is complementary to the 3' end of the ribozyme, allowing regeneration of its original, active form. PCR DNA (~250–500 ng, 5–10% of the total) then served as template in an in vitro transcription reaction, carried out in a 25–50 μl volume.

The transcribed RNA was isolated by polyacrylamide gel electrophoresis, visualized by UV shadowing, cut and eluted from gel, purified on duPont Nensorb (duPont de Nemours, Wilmington, Del.), and quantified spectrophotometrically, as described above. The entire process was repeated 18 times, the first 9 as described above and the second 9 with the incubation time for the cleavage reaction reduced from 1 hr to 5 min. Occasionally, the cDNA was purified to improve the quality of the PCR amplification. To do so, cDNA was synthesized as above except in the presence of 25–50 μCi [a-$^{32}$P]dATP. Labeled cDNA was isolated by electrophoresis in a 5% polyacrylamide/8M urea gel, visualized by autoradiography, cut and eluted from gel, and purified on DuPont Nensorb.

DNA substrate 5'-GGCCCTCTATTTATTTA-3' (SEQ ID NO 15) and DNA product 5'-GGCCCTCT-3' (SEQ ID NO 16) were (5'-$^{32}$P)-labeled in a 20 μl reaction mixture containing 20 pmol oligonucleotide, 10 pmol (4.5 μCi/pmol) [g-$^{32}$P]ATP, 5 mM $MgCl_2$, 25 mM CHES (pH 9.0), 3 mM DTT, and 1.25 U/μl T4 polynucleotide kinase, incubated at 37° C. for 1 hr. Labeled oligonucleotide was isolated by electrophoresis in a 20% polyacrylamide/8M urea gel, visualized by autoradiography, eluted from the gel, and purified on duPont NENsorb (duPont, Wilmington, Del.).

The RNA substrate 5'-GGCCCUCUAUUUAUUUA-3' (SEQ ID NO 20) was prepared by in vitro transcription using a partially single-stranded synthetic DNA template (Milligan et al., *Nucleic Acids Res.* 15: 8783–8798 (1987)), as described previously. The RNA transcript was dephosphorylated with calf intestine phosphatase, extracted with phenol and chloroform, and then (5'-$^{32}$P)-labeled and purified as described above.

The G18 subclones were obtained as previously described (see Example 1 above). The G27 subclones were obtained using the Invitrogen TA Cloning Kit (Invitrogen, San Diego, Calif.). The PCR DNA at G27 was ligated into a linearized plasmid, and the resulting DNA was used to transform competent INVaF' cells, which were grown on ampicillin/X-gal plates. Individual colonies containing the insert were identified by their white color, chosen at random, and grown overnight in liquid media. Plasmid DNA was prepared by the boiling, lysis method (Holmes & Quigley, *Anal. Biochem.* 114: 193–197 (1981)) and screened for the presence of insert by restriction digestion. Cloned individuals were sequenced by the dideoxy chain-termination method, as previously described (Sanger et al., *PNAS USA* 74: 5463–5467 (1977); Beaudry & Joyce, Id. (1992)). Complete sequences of individual subclones are available upon request. Individual ribozymes were prepared as follows: the gene encoding the ribozyme was amplified by the PCR using Primer 1b and Primer 2; the resulting DNA was used as a template for in vitro transcription; the RNA products were isolated by polyacrylamide gel electrophoresis, and were purified and quantified as described above.

C. Substrate Cleavage Activity

Substrate cleavage activity for the population as a whole is generally monitored via gel electrophoresis assay involving cleavage of [5'-$^{32}$P]-labeled substrate to yield a specific product. Cleavage of the substrate ("S") in the absence of enzyme, in the presence of the wild-type Tetrahymena ribozyme (L-21 form), and in the presence of the population of RNAs obtained at each generation ($G_n$, beginning with a value of 0 for n) is measured.

Reaction conditions may be described as follows: 0.5 μM ribozyme, 0.1 μM substrate (2.6 μCi/pmol), 30 mM EPPS (pH 7.5); either 10 mM $MgCl_2$, 37° C., 1 hour (low) or 50 mM $MgCl_2$, 2 mM spermidine, 50° C., 1 hour (high). Reaction products were separated by electrophoresis in a 20% polyacrylamide-8M urea gel, of which autoradiograms were made. Conditions of "high" $MgCl_2$ may be considered useful initially, before the ribozyme has "evolved", to facilitate DNA cleavage.

It is expected that any given mutation would more likely be detrimental than beneficial, although there may be a substantial number of neutral mutations. For example, in examples directed to improvement of DNA cleavage activity, the activity of the generation 0 population was observed to be less efficient than for the wild type. The generation 1 population, having been selected for DNA cleavage activity under physiologic conditions, showed improved catalytic activity compared to generation 0 and was slightly improved over the wild type. Through successive generations, there is continued improvement of phenotype. By generation 7, the population as a whole cleaved DNA more efficiently at 37° C. and 10 mM $MgCl_2$ than does the wild type at the high-temperature, high-$MgCl_2$ condition. Through successive generations, the rate of improvement has continued to increase.

RNA purification and substrate cleavage were conducted as described in Example 1.

DNA substrates may be prepared via the following procedure. For example, an exemplary [3'-$^{32}$P]-labeled DNA substrate was prepared with terminal deoxynucleotidyl transferase (TdT; available from U.S. Biochemical, Cleveland, Ohio, or BRL, Gaithersburg, Md.). Reaction conditions were as follows: 4 μM d(GGCCCTCTA$_3$(TA$_3$)$_3$) (SEQ ID NO 17), 1 μM [$\alpha$-$^{32}$P]dATP (3 μCi/pmol), 1 mM $CoCl_2$, 1 mM DTT, 50 mM potassium cacodylate (pH 7.2) and terminal transferase at 2.7 U/μl, incubated at 37° C. for 30 minutes. The product corresponding to addition of a single dA residue was purified by electrophoresis in a 20% polyacrylamide-8M urea gel and subsequent affinity chromatography on NENsorb (duPont, Wilmington, Del.). The hydrolysis product forms either by direct cleavage of the DNA substrate or by cleavage of the ribozyme-d($A_3$($TA_3$)$_3$A) covalent intermediate. Together, these reactions account for less than 5% of the cleaved substrate.

After ten generations, DNA cleavage activity for the population as a whole was 30 times higher than that of the wild type. Because selection is based on primer hybridization to the EP covalent intermediate (see FIG. 2B), there is selection pressure against the subsequent site-specific hydrolysis reaction. As a consequence, the efficiency of the hydrolysis reaction relative to the initial phosphoester transfer event drops from 4.9% for the wild type to 1.5% for the generation 10 population. There is selection pressure favoring accurate cleavage of the DNA at the target phosphodiester; inaccurate cleavage would result in partial mismatch of the primer used to initiate selective amplification. The accuracy of cleavage at first declines from 90% for the wild type to 45% for the generation 8 population, and then rises to 60% for the generation 10 population. There may be some individuals in the population that sacrifice accuracy for improved cleavage activity in order to enjoy an overall selective advantage. Of course, a preferred result is an individual having both high accuracy and high cleavage activity.

D. Preparation and Sequencing of Subclones

Although evolution in natural populations is an accomplished fact, evolution in vitro is a work in progress that allows the experimenter to access any time period in evolutionary history. Subclones were obtained from the evolving population at every generation and individual ribozymes were then sequence.

Subclones were prepared and sequenced as described in Example 1., part B, section 5. As noted therein, subclones may be obtained from the evolving population at every generation; alternatively, specific generations may also be chosen for detailed analysis.

Analysis of the determined sequences indicates how genotype changes over the course of evolutionary history. From generation 0 to generation 3, variation is discarded throughout much of the catalytic core of the ribozyme. The mean number of mutations per subclone decreased from 7.0 at generation 0 to 2.7 at generation 3. By generation 3, a small number of mutations outside of the original zone of random mutation have occurred because of ongoing mutation events. The consensus sequence still tends to be that of the wild type. Analysis of subsequent generations suggests that accumulation of mutations coincides with improvement in the phenotype of the population as a whole. The mean number of mutations per subclone is also observed to increase, as a larger proportion of subclones adopt the common mutations and as mutations accumulate outside of the original zone of random mutation.

The relation between genotype and phenotype in the context of an RNA-based evolving system can readily be formalized once catalytic, kinetic, and comparable data are collected and analyzed. Genotype can be represented as a matrix A, the rows corresponding to individuals in the population and the columns corresponding to functionally significant positions within the nucleotide sequence. An exemplary analysis is illustrated in Beaudry and Joyce, *Science* 257: 635–641 (1992).

The data obtained from a relatively small number of individuals may not be sufficient to provide a meaningful solution to the relation of genotype to phenotype, even for those nucleotide positions that are known to be most significant based on their high frequency of accepted mutation. The weighing vector x may thus be used as a guide to help decide which mutations are sufficiently important to warrant individual study. (See, e.g., Beaudry and Joyce, Id. (1992).)

E. Site-Directed Mutagenesis

Individual enzymatic RNA molecules containing single mutations may be prepared by site-directed mutagenesis for analysis of the relative significance of a particular mutation, as described in Example 1.B.6. Catalytic activity is then studied with an appropriate [5'-$^{32}$P]-labeled oligodeoxyribonucleotide substrate.

F. Kinetic Analysis

All cleavage reactions were carried out according to the procedures described in Example 1.B.7. $K_M$ and $k_{cat}$ values were determined in experiments with substrate (S) in excess over ribozyme (E). Initial rates of reaction ($v_o$), over a range of substrate concentrations, were estimated from the initial linear phase, generally the first 5% or less of the reaction. Typically 8 data points were fit by a least squares method to a theoretical line given by the equation: $v = -K_M (v_o/[S]) + V_{max}$.

Single-turnover experiments were performed with ribozyme in excess of substrate (Herschlag & Cech, *Biochemistry* 29:10159–10171 (1990b)). Initial rates ($k_{obs}$) were obtained using no more than the first 5% of the reaction. Given that $k_{cat}/K_M = k_{obs}/[E]$, each $k_{obs}$ value, obtained at different ribozyme concentrations, provided an estimate of $k_{cat}/K_M$. Generally 8 or more measurements of $k_{cat}/K_M$ were obtained.

Specific catalytic properties of a DNA-cleaving ribozyme can be optimized by appropriate manipulation of the selection constraints during an in evolution procedure. For example, beginning with a heterogeneous population of ribozymes, enriched for modest DNA-cleavage activity, 27 generations were produced to obtain DNA-cleaving ribozymes that have a catalytic rate of 0.7 min$^{-1}$ and a substrate binding affinity of 10$^{-9}$ M. These catalytic parameters are improved 10$^3$-fold and 10$^4$-fold, respectively, compared to the wild-type. The greatest improvement in $K_D$ and $K_M$ occurred between G9 and G18 in response to alteration of the selection constraints to favor ribozymes with enhanced affinity for the DNA substrate (not shown). Likewise, based on $k_{cat}$ values for representative individuals, the greatest improvement in $k_{cat}$ occurred between G18 and G27, following alteration of the selection constraints to favor a faster rate of catalysis.

It is important to note that some mutations may confer no selective advantage with respect to catalysis, but instead enhance the ability of the polymerase enzymes (i.e., reverse transcriptase, T7 RNA polymerase, and Taq polymerase) to operate efficiently during the amplification procedure. Future studies, relying on site-directed mutagenesis analysis, will enable us to assess the contribution made by various mutations, in either the conserved core or the peripheral regions, to substrate binding, first-order reaction rates, and ribozyme folding.

Beginning with generation 19, the reaction time was reduced from 1 hr to 5 min to favor selection of ribozymes with increased $k_{cat}$ values. To study the effect of this change, two individuals isolated from the population at G9, G18 and G27 were chosen for formal kinetic analysis (Table 3). These ribozymes are representative of the population from which they were isolated because they contain most of the prominent mutations that occur in their respective populations. In addition, the total number of mutations in each of the studied individuals coincides with the mean number of mutations per subclone in the corresponding population. It is emphasized that the $k_{cat}$ and $K_M$ values of the studied individuals are not equivalent to the average $k_{cat}$ and $K_M$ values for the entire population. It is likely that the catalytic efficiencies of the studied ribozymes are somewhat higher than the average because these ribozymes possess a greater fraction of the dominant mutations than a typical individual in the population. Nevertheless, the relative differences in $k_{cat}$ and $K_M$ values between representative pairs of individuals should be comparable. As expected, the improvement in $k_{cat}$ is greatest between the G18 and G27 ribozymes (Table 3), while the improvement in $K_M$ is greatest between the G9 and G18 ribozymes.

Table 3, illustrating the catalytic parameters of DNA-cleaving enzymatic RNA molecules, is reproduced hereinbelow.

TABLE 3

Catalytic Parameters of DNA-Cleaving Ribozymes

| Ribozyme | Mutations | $k_{cat}^{b}$ (min$^{-1}$) | $K_M^{b}$ (µM) | $k_{cat}/K_M$ (M$^{-1}$ min$^{-1}$) |
|---|---|---|---|---|
| wt[a] | 0 | 2.4 (±0.2) × 10$^{-4}$ | 6.0 ± 1.7 | 4.0 × 10$^1$ |
| G9 #23[a] | 7 | 5.1 (±0.2) × 10$^{-3}$ | 1.8 ± 0.3 | 2.8 × 10$^3$ |
| G9 #29[a] | 6 | 7.1 (±0.3) × 10$^{-3}$ | 1.9 ± 0.3 | 3.8 × 10$^3$ |
| G18 #13[c] | 12[f] | 1.7 (±0.1) × 10$^{-2}$ | 0.24 ± 0.04 | 7.1 × 10$^4$ |
| G18 #66[c] | 13[g] | 1.1 (±0.1) × 10$^{-2}$ | 0.32 ± 0.08 | 3.5 × 10$^4$ |
| G27 #48[d] | 17[h] | 7.0 (±0.6) × 10$^{-1}$ | 0.31 ± 0.05 | 2.3 × 10$^6$ |
| G27 #61[e] | 15[i] | 3.3 (±0.7) × 10$^{-1}$ | 0.11 ± 0.06 | 2.9 × 10$^6$ |

[a]Data obtained previously (see Example 1 above), modified slightly as a result of subsequent statistical analysis.
[b]Measurements were carried out as described in Materials and Methods with:
[c]0.025 µM ribozyme and 0.125, 0.25, 0.5, and 1.0 µM DNA substrate;
[d]0.02 µM ribozyme and 0.1, 0.2, 0.4, and 0.8 µM DNA substrate; or
[e]0.02 µM ribozyme and 0.05, 0.1, 0.2, and 0.4 µM DNA substrate.
[f]44:G→A, 94:A→U, 115:A→U, 116:G→A, 138:C→A, 188:G→A, 190:U→A, 191:G→U, 205:U→C, 215:G→A, 312:G→A, and 317:U→G.
[g]44:G→A, 94:A→U, 115:A→U, 166:G→A, 138:C→A, 167:U→G, 188:G→A, 190:U→A, 191:G→U, 205:U→C, 215:G→A, 239:U→A, and 312:G→A.
[h]44:G→A, 51/52:insert AGAA, 87:A→del, 94:A→U, 115:A→U, 116:G→A, 166:C→A, 170:C→U, 188:G→A, 190:U→A, 191:G→U, 205:U→C, 215:G→A, 239:U→A, 312:G→A, 350:C→U, and 364:C→U.
[i]44:G→A, 51/52:insert AGAA, 87:A→del, 94:A→U, 115:A→U, 116:G→A, 166:C→A, 170:C→U, 188:G→A, 190:U→A, 191:G→U, 205:U→C, 215:G→A, 313:G→C, and 314:A→G.

G. Determination of Binding Constants

The equilibrium dissociation constant, $K_D$, of the complex between ribozyme and DNA product (P) was determined by gel-shift analysis in a native polyacrylamide gel (Pyle et al., PNAS USA 87: 8187–8191 (1990)). The procedure used is described in Example 1 above, in part B.8.

A binding curve was generated by plotting the percentage of product bound to ribozyme (% bound) over a range of ribozyme concentrations. $K_D$ was determined by fitting the data to a theoretical binding curve using a least squares method. Because ribozyme was in vast excess over product, the theoretical binding curve could be represented by the equation: % bound=[E]/([E]+$K_D$), where $K_D$=[E] when half of the total product is bound to the ribozyme.

The present successful phylogeny was continued beyond the tenth generation, after decreasing the concentration of DNA substrate in the target reaction, as further described herein. Through the first ten generations the substrate concentration was 10 µM, roughly matching the $K_m$ for the wild type. Now that the evolved individuals have attained a $K_m$ of about 2 µM, the substrate concentration has been reduced to subsaturating levels to promote further improvement in substrate binding. In addition, catalytic turnover in the DNA cleavage reaction is being improved by selecting for both phosphoester transfer activity, which generates the EP covalent intermediate, and subsequent RNA-catalyzed site-specific hydrolysis activity, which frees the ribozyme to act on another substrate molecule.

The selection scheme used herein may be applied to various substrates of the form: d(CCCTCNA$_3$(TA$_3$)$_3$) (SEQ ID NO 18), where N refers to a nucleotide analog and the ribozyme is selected for its ability to cleave the phosphodiester bond following the sequence CCCTCN (SEQ ID NO 19). Examples of nucleotide analogs useful according to the present invention include those listed in the Table, appearing in section C of the Detailed Description.

The substrate need not be a nucleotide or nucleotide analog. The only requirement is that RNAs that react with the substrate become tagged in some way so that they can be distinguished from nonreactive molecules with respect to the amplification process. For example, reactive RNAs could become joined to a portion of the substrate that is attached to a solid support, while nonreactive RNAs would be washed away, leaving the bound RNAs to be selectively amplified. These and other methodologies are further described below.

H. Extension of Directed Evolution to Develop Other Evolved Species

As an in vitro model of Darwinian evolution, a population of macromolecular catalysts was directed toward the expression of novel catalytic function. In the present Example, the development of ribozymes that cleave DNA with improved efficiency under physiologic conditions has been demonstrated.

I. Evolution In Vitro

Beginning with the 9th generation (G9) population of ribozymes obtained in a previous study (Beaudry & Joyce, Id. (1992)), 18 additional generations of in vitro evolution were carried out. Variation in the population was maintained by PCR amplification, which introduces mutations at a rate of ~0.1% per nucleotide position per generation. Because mutation is ongoing, evolution based on Darwinian principles can occur. Progeny ribozymes have the opportunity to acquire new mutations that confer favorable attributes not possessed by the parent molecules. This phenomenon is reflected by the steadily increasing frequency of accepted mutations over the 27 generations.

Sequence data was obtained from 50 randomly-chosen subclones, isolated from the evolving population at G9, G18, and G27, and illustrates sites at which mutations occurred over the course of evolution. The mean number of mutations per subclone rose from 5.9 at G9, to 12.7 at G18, and to 16.5 at G27. Most of the mutations occurred within the phylogenetically conserved portions of the ribozyme that were randomized in the initial population (not shown). However, 26% of the total mutations at G18, and 38% at G27, occurred in peripheral regions as a result of ongoing mutagenesis. Most of the commonly-occurring mutations (>30% frequency) that occur in the G18 subclones were not observed at G9 (not shown), suggesting that these mutations arose in response to the increased selection pressure designed to enhance substrate binding affinity. Between G18 and G27, nearly all of the most commonly-occurring mutations continued to increase in frequency (not shown). However, two significant mutations, the NGAA insertion between positions 51 and 52 and the C→U change at position 170, first appeared during this interval, suggesting that these mutations arose in response to the increased selection pressure designed to enhance the catalytic rate.

The changes at nucleotide positions 188, 190, and 191 in the P5a region (see FIGS. 1 and 3) co-occur in 90% of subclones, while mutations in the J4/5 and J5/4 internal loop at positions 115, 116, and 205 co-occur in 68% of the subclones at G18. Interestingly, the J4/5 and J5/4 mutations co-occur only if the set of P5a mutations is also present ($c^2$=110, p <0.001), suggesting an interaction between these two regions.

The 313:G→Y and 314:A→G mutations nearly always occur together. These mutations co-occur in 16 of 50 subclones at G9, 11 of 50 subclones at G18, and 44 of 50 subclones at G27. Only two G27 subclones contain the mutation at position 313 but lack the mutation at position 314. At G9 and G18, the 313 mutation always occurs as a G→U change. At G27, however, the 313 mutation occurs primarily as a G→C change, with the G→U change occurring only once. The GA sequence normally present at positions 313–314 is thought to form a short duplex structure (P9.0) that brings the 3'-terminal guanosine residue of the ribozyme into the catalytic core (Michel et al., *Nature* 342:391–395 (1989); Michel et al., *Genes Dev.* 4: 777–788 (1990); Michel, et al., *J. Mol. Biol.* 216: 585–610 (1990)). The 3'—OH of this guanosine serves as the nucleophile in the RNA-catalyzed phosphoester reaction. Although the 313–314 mutation would prevent the P9.0 duplex from forming, the 313–314:GA→UG change confers selective advantage with respect to the DNA-cleavage reaction, as demonstrated by site-directed mutagenesis studies (Beaudry & Joyce, Id. (1992)). The appearance of the 313–314:GA→ CG change, between G18 and G27, suggests that this altered form of the 313–314 mutation may contribute to the improved catalytic rate of the DNA-cleavage reaction.

The 312:G→A mutation occurs only if the 313–314:GA→YG mutations are not present. The 312:G→A change is present in 4 of 25 subclones at G3, 8 of 25 subclones at G6, and 5 of 50 subclones at G9 (Beaudry & Joyce, Id. (1992)). There is a dramatic rise in the frequency of the 312:G→A mutation between G9 and G18, followed by an equally dramatic drop between G18 and G27 (not shown). As the frequency of the 312:G→A mutation declines, the 313–314:GA→YG mutations become more abundant.

The 215:G→A mutation, present at high frequency in all of the studied populations, putatively allows a Watson-Crick base pair to form with the U at position 258 (see FIG. 1). This change is present in nearly all of the subclones at G18 and G27. Of the 12 individuals that lack this mutation, 11 carry a U→C change at position 258, which would allow a Watson-Crick pair to form with the wild-type G at position 215. Thus, in 99 of 100 subclones from G18 and G27, a Watson-Crick base pair is expected to form between positions 215 and 258.

J. Improvement of DNA Binding Affinity

Beginning with G10, the concentration of DNA substrate employed during the RNA-catalyzed reaction was lowered from 10 µM to 0.2 µM to impose increased selection pressure favoring individuals with enhanced substrate binding affinity. In order to assess the impact of this change, $K_D$ values for the complex between ribozyme and DNA product (GGCCTCT) were determined for the population of ribozymes at every third generation over the 27 generations (not shown).

A binding curve showing data obtained for the G27 population of ribozymes and illustrating the improvement in substrate binding affinity over 27 successive generations of in vitro evolution was prepared (not shown). Data was fit by a least squares method to a theoretical binding curve (indicated by solid line), given by the equation: $y=[E]/([E]+K_D)$, where y is the fraction of product (P) bound to ribozyme (E). In this case, $K_D$=51 (±2) nM. The $K_D$ for the population of ribozymes at every third generation was also calculated; standard errors averaged 11% (not shown).

The DNA product rather than substrate was employed to avoid a cleavage reaction during the gel-shift analysis. The binding affinity for the product is assumed to be similar to that of the substrate, based on previous studies showing that the wild-type ribozyme binds the RNA substrate with the same affinity as it binds the product (Pyle et al., *PNAS USA* 87:8187–8191 (1990); Herschlag & Cech, *Biochemistry* 29: 10159–10171 (1990b)).

Binding data for each studied population was fit to a theoretical binding curve. As expected, the greatest improvement in binding affinity occurred between G9 and G18, subsequent to tightening of the selection constraints (not shown). After G18, the population became saturated with ribozymes having a $K_D$ of less than 0.2 µM, accounting for the slow but continued improvement between G18 and G27.

The foregoing specification, including the specific embodiments and examples, is intended to be illustrative of the present invention and is not to be taken as limiting. Numerous other variations and modifications can be effected without departing from the true spirit and scope of the present invention.

I claim:

1. An enzymatic RNA molecule comprising a ribonucleotide polymer having a nucleotide sequence from the group I intron of *T. thermophila*, wherein said polymer catalyzes the hydrolysis of amide bonds in a substrate, and wherein said substrate comprises an oligonucleotide containing an amide, bond.

2. The enzymatic RNA molecule of claim 1, wherein said polymer has a catalytic activity for hydrolyzing said substrate to produce an amino cleavage product and a ribozyme amidase intermediate.

3. The enzymatic RNA molecule of claim 2, wherein:
    a. said ribonucleotide polymer has a 5' terminal nucleotide with a ribose sugar having a nucleophilic 2' hydroxyl; and
    b. said ribozyme amidase intermediate includes an ester linkage between said nucleophilic 2' hydroxyl and a carboxy group of said substrate.

4. The enzymatic RNA molecule of claim 3, wherein said 5' terminal nucleotide includes a guanine base.

5. The enzymatic RNA molecule of claim 3, wherein said substrate includes a peptide having two or more amino acid residues including a carboxy terminal amino acid residue bearing the carboxy group of said substrate, said carboxy terminal amino acid residue being covalently linked by the ester linkage to the 2' hydroxyl of said ribonucleotide polymer.

6. The enzymatic RNA molecule of claim 2, wherein said ribonucleotide polymer has an effective binding affinity for said substrate and lacks an effective binding affinity for said amino cleavage product.

7. The enzymatic RNA molecule of claim 1, further comprising a cofactor bound to said ribonucleotide polymer, said cofactor including a guanine nucleotide having a ribose sugar with a nucleophilic 2' hydroxyl capable of forming an acid labile ester intermediate with the carboxy cleavage product.

8. The enzymatic RNA molecule of claim 1, wherein said nucleotide sequence comprises SEQ ID NO 1 and further includes one or more of the following mutations:

| | |
|---|---|
| 44:G→A; | 51/52:insert AGAA; |
| 87:A→deleted; | 94:A→U; |
| 94:A→C; | 115:A→U; |
| 116:G→A; | 138:C→A; |
| 166:C→A; | 167:U→G; |
| 170:C→U; | 188:G→A; |
| 190:U→A; | 191:G→U; |
| 205:U→C; | 215:G→A; |
| 239:U→A; | 258:U→C; |
| 312:G→A; | 313:G→U; |
| 313:G→C; | 314:A→G; |
| 317:U→G; | 317:U→C; |
| 317:U→A; | 333:U→C; |
| 350:C→U; and | |
| 364:C→U. | |

9. A ribozyme amidase intermediate comprising:
    a. a ribonucleotide polymer having a nucleotide sequence from the group I intron of *T. thermophila* and further including a 5' terminal nucleotide with a ribose sugar having a 2' hydroxyl; and
    b. a substrate molecule comprising an oligonucleotide containing an amide bond and having one or more amino acid residues including a carboxy terminal amino acid residue, said carboxy terminal amino acid residue being covalently linked by an ester bond to the 2' hydroxyl of said ribonucleotide polymer.

10. The ribozyme amidase intermediate of claim 9, wherein said ribonucleotide polymer comprises SEQ ID NO 1 and further includes one or more of the following mutations:

| | |
|---|---|
| 44:G→A; | 51/52:insert AGAA; |
| 87:A→deleted; | 94:A→U; |
| 94:A→C; | 115:A→U; |
| 116:G→A; | 138:C→A; |
| 166:C→A; | 167:U→G; |
| 170:C→U; | 188:G→A; |
| 190:U→A; | 191:G→U; |
| 205:U→C; | 215:G→A; |
| 239:U→A; | 258:U→C; |
| 312:G→A; | 313:G→U; |
| 313:G→C; | 314:A→G; |
| 317:U→G; | 317:U→C; |
| 317:U→A; | 333:U→C; |
| 350:C→U; and | |
| 364:C→U. | |

11. A ribozyme amidase intermediate comprising:
    a. a ribonucleotide polymer having a nucleotide sequence from the group I intron of *T. thermophila*;
    b. a cofactor including a guanine nucleotide having a ribose sugar with a 2' hydroxyl; and
    c. a substrate molecule comprising an oligonucleotide containing an amide bond and having one or more amino acid residues including a carboxy terminal amino acid residue, said carboxyl terminal amino acid residue being covalently linked by an ester bond to the 2' hydroxyl of said guanine nucleotide.

12. The ribozyme amidase intermediate of claim 11, wherein said ribonucleotide polymer comprises SEQ ID NO 1 and further includes one or more of the following mutations:

| | |
|---|---|
| 44:G→A; | 51/52:insert AGAA; |
| 87:A→deleted; | 94:A→U; |
| 94:A→C; | 115:A→U; |
| 116:G→A; | 138:C→A; |
| 166:C→A; | 167:U→G; |
| 170:C→U; | 188:G→A; |
| 190:U→A; | 191:G→U; |
| 205:U→C; | 215:G→A; |
| 239:U→A; | 258:U→C; |
| 312:G→A; | 313:G→U; |
| 313:G→C; | 314:A→G; |
| 317:U→G; | 317:U→C; |
| 317:U→A; | 333:U→C; |
| 350:C→U; and | |
| 364:C→U. | |

13. A method for catalytically hydrolyzing a substrate comprising an oligonucleotide containing an amide bond, the method comprising the following step A:

contacting said substrate with a ribozyme comprising a ribonucleotide polymer having a nucleotide sequence from the group I intron of *T. thermophila* and having a catalytic activity for hydrolyzing said substrate and producing an amino cleavage product and a ribozyme amidase intermediate, said ribozyme amidase intermediate including a carboxyl of said substrate bonded by an ester bond to a 2'0 hydroxyl of a ribose sugar on a 5' terminal nucleotide of the ribonucleotide polymer.

14. A method for catalytically hydrolyzing a substrate as described in claim 13, the method further comprising step B as follows, to be performed after said Step A:

hydrolyzing the ester bond of said ribozyme amidase intermediate to produce a carboxy cleavage product.

15. A method of cleaving an amide bond, comprising:

a. admixing an enzymatic RNA molecule according to claim 1 with a substrate comprising an oligonucleotide containing an amide bond, to form a reaction admixture; and b. maintaining said admixture under predetermined reaction conditions to allow said enzymatic RNA molecule to cleave said amide bond.

16. The method of claim 15, wherein said enzymatic RNA molecule is able to cleave an amide bond at a preselected site.

17. The method of claim 15, further comprising the steps of:

a. separating said products from said enzymatic RNA molecule; and b. adding additional substrate to said enzymatic RNA molecule to form a new reaction admixture.

18. A method of selecting an enzymatic RNA molecule that cleaves amide bonds, comprising the following consecutive steps:

a. admixing amide bond-containing oligonucleotide substrate molecules with a population of *T. thermophila* group I introns (ribozymes) to form an admixture;

b. maintaining said admixture for a sufficient period of time and under predetermined reaction conditions to allow said ribozymes and said substrate to interact and form ribozyme-product complexes;

c. isolating any ribozyme-product complexes that form;

d. allowing said ribozyme-product complex to dissociate into separate ribozyme and product; and e. separating said ribozymes from said product.

19. The method of claim 18, wherein said substrate is tagged with an immobilizing agent.

20. A method of engineering enzymatic RNA molecules that cleave amide bonds, comprising the following steps:

a. introducing genetic variation into a population of *T. thermophila* group I introns (ribozymes) to produce a variant population;

b. selecting individuals from said variant population that meet predetermined selection criteria;

c. separating said selected individuals from the remainder of said variant population; and d. amplifying said selected individuals.

* * * * *